United States Patent
Scott et al.

(10) Patent No.: US 11,867,619 B1
(45) Date of Patent: Jan. 9, 2024

(54) AIR QUALITY MONITORING SYSTEM AND METHOD

(71) Applicant: Project Canary, PBC, Denver, CO (US)

(72) Inventors: Anna Ailene Scott, Austin, TX (US); Nasr E. Alkadi, Edmond, OK (US); Yan Azdoud, Austin, TX (US); Nathan C. Eichenlaub, Denver, CO (US); William J. Foiles, Denver, CO (US); Christopher Daniel Kelley, Austin, TX (US); Shyla Kupis, Atlanta, GA (US)

(73) Assignee: PROJECT CANARY, PBC, Denver, CO (US)

( * ) Notice: Subject to any disclaimer, the term of this patent is extended or adjusted under 35 U.S.C. 154(b) by 0 days.

(21) Appl. No.: 18/241,776

(22) Filed: Sep. 1, 2023

Related U.S. Application Data

(63) Continuation of application No. 18/205,445, filed on Jun. 2, 2023, now Pat. No. 11,781,979, which is a
(Continued)

(51) Int. Cl.
*G01N 21/35* (2014.01)
*G01N 21/3504* (2014.01)
(Continued)

(52) U.S. Cl.
CPC ..... *G01N 21/3504* (2013.01); *G01N 33/0036* (2013.01); *G01P 13/045* (2013.01)

(58) Field of Classification Search
CPC ............ G01N 21/3504; G01N 33/0036; G01P 13/045
See application file for complete search history.

(56) References Cited

U.S. PATENT DOCUMENTS

| | | | |
|---|---|---|---|
| 3,206,982 A | 9/1965 | Blondfield | |
| 3,662,171 A | 5/1972 | Brengman et al. | |

(Continued)

FOREIGN PATENT DOCUMENTS

| | | |
|---|---|---|
| CH | 703014 A2 | 10/2011 |
| CN | 107782374 A | 3/2018 |

(Continued)

OTHER PUBLICATIONS

U.S. Appl. No. 17/813,602, filed Jul. 19, 2022, Nathan C. Eichenlaub.
(Continued)

*Primary Examiner* — Jamil Ahmed
(74) *Attorney, Agent, or Firm* — Stephen B. Katsaros; Patent Engineering, LLC

(57) ABSTRACT

In one illustrative configuration, an air quality monitoring system may enable wide-scale deployment of multiple air quality monitors with high-confidence and actionable data is provided. Further, the air quality monitoring system may enable identifying a target emission from a plurality of potential sources at a site based on simulating plume models. The simulation of plume models may take into consideration various simulation parameters including wind speed and direction. Further, methods of determining a plume flux of a plume of emissions at a site, and methods of transmitting data from an air quality monitor are disclosed.

14 Claims, 41 Drawing Sheets

Related U.S. Application Data continuation of application No. 18/098,430, filed on Jan. 18, 2023, now Pat. No. 11,754,495, which is a continuation of application No. 17/843,613, filed on Jun. 17, 2022, now Pat. No. 11,592,390, which is a continuation of application No. 17/843,554, filed on Jun. 17, 2022, now Pat. No. 11,585,752, which is a continuation of application No. 17/541,693, filed on Dec. 3, 2021, now Pat. No. 11,366,057, which is a continuation of application No. PCT/US2021/049702, filed on Sep. 9, 2021.

(60) Provisional application No. 63/233,694, filed on Aug. 16, 2021, provisional application No. 63/076,829, filed on Sep. 10, 2020.

(51) Int. Cl.
  *G01N 33/00* (2006.01)
  *G01P 13/04* (2006.01)

(56) References Cited

U.S. PATENT DOCUMENTS

| | | | |
|---|---|---|---|
| 3,780,566 A | 12/1973 | Smith et al. | |
| 3,817,108 A | 6/1974 | Principe et al. | |
| 4,135,092 A | 1/1979 | Milly | |
| 4,551,719 A | 11/1985 | Carlin et al. | |
| 5,132,968 A | 7/1992 | Cephus | |
| 5,281,816 A | 1/1994 | Jacobson et al. | |
| 5,406,265 A | 4/1995 | Trozzo et al. | |
| 5,479,359 A | 12/1995 | Rogero et al. | |
| 5,568,121 A | 10/1996 | Lamensdorf | |
| 5,604,298 A | 2/1997 | Dosoretz et al. | |
| 6,061,141 A | 5/2000 | Goldenberg et al. | |
| 6,114,964 A | 9/2000 | Fasano | |
| 6,167,766 B1 | 1/2001 | Dunn et al. | |
| 6,169,488 B1 | 1/2001 | Ketler | |
| 6,252,510 B1 | 6/2001 | Dungan | |
| 6,259,956 B1 | 7/2001 | Myers et al. | |
| 6,317,029 B1 | 11/2001 | Fleeter | |
| 6,415,646 B1 | 7/2002 | Kessel et al. | |
| 6,490,530 B1 | 12/2002 | Wyatt | |
| 6,794,991 B2 | 9/2004 | Dungan | |
| 6,865,926 B2 | 3/2005 | O'Brien et al. | |
| 7,075,653 B1 | 7/2006 | Rutherford | |
| 7,080,544 B2 | 7/2006 | Stepanik et al. | |
| 7,647,136 B2 | 1/2010 | McDowell | |
| 7,805,271 B2 | 9/2010 | Nojima et al. | |
| 7,949,615 B2 | 5/2011 | Ehlers et al. | |
| 8,197,752 B2 | 6/2012 | Nojima et al. | |
| 8,275,719 B1 | 9/2012 | Agnew et al. | |
| 8,341,106 B1 | 12/2012 | Scolnicov et al. | |
| 8,346,635 B1 | 1/2013 | Olim | |
| 8,485,019 B2 | 7/2013 | Groves | |
| 8,510,059 B2 | 8/2013 | Prince | |
| 8,600,568 B2 | 12/2013 | Smaidris | |
| 8,712,335 B2 | 4/2014 | Mathur et al. | |
| 8,714,035 B2 | 5/2014 | Mihaylav et al. | |
| 8,949,037 B2 | 2/2015 | Prince et al. | |
| 9,018,963 B2 | 4/2015 | Sim et al. | |
| 9,075,016 B2 | 7/2015 | Groves | |
| 9,188,503 B2 | 11/2015 | Kloepper et al. | |
| 9,202,198 B2 | 12/2015 | Margonis et al. | |
| 9,210,541 B2 | 12/2015 | Root et al. | |
| 9,298,925 B1 | 3/2016 | Crittall et al. | |
| 9,430,644 B2 | 8/2016 | Gonzalez et al. | |
| 9,754,472 B2 | 9/2017 | Johnson et al. | |
| 9,878,656 B2 | 1/2018 | Gergets et al. | |
| 9,915,399 B1 | 3/2018 | Latshaw et al. | |
| 9,978,251 B2 | 5/2018 | Gonia et al. | |
| 10,021,466 B2 | 7/2018 | Guglielmo et al. | |
| 10,031,040 B1 | 7/2018 | Smith et al. | |
| 10,089,849 B2 | 10/2018 | Liu et al. | |
| 10,119,890 B2 | 11/2018 | Massengale et al. | |
| 10,190,976 B2 | 1/2019 | Waxman et al. | |
| 10,210,738 B2 | 2/2019 | Johnson, Jr. et al. | |
| D842,134 S | 3/2019 | Doi et al. | |
| 10,371,682 B2 | 8/2019 | Berndt et al. | |
| 10,634,558 B1 | 4/2020 | Scott et al. | |
| 10,671,772 B2 | 6/2020 | Luquist et al. | |
| 10,697,947 B1 | 6/2020 | Armitage | |
| 63,076,829 | 9/2020 | Scott | |
| 10,814,028 B2 | 10/2020 | Becker et al. | |
| 10,876,890 B2 | 12/2020 | Scott et al. | |
| 11,132,752 B2 | 9/2021 | Finkel et al. | |
| 11,193,822 B2 | 12/2021 | Scott et al. | |
| 11,215,593 B2 | 1/2022 | Armitage | |
| 11,366,057 B2 | 6/2022 | Scott et al. | |
| 17,813,585 | 7/2022 | Eichenlaub | |
| 11,408,870 B2 | 8/2022 | Armitage | |
| 11,573,157 B2 | 2/2023 | Cyrus et al. | |
| 2001/0040509 A1 | 11/2001 | Dungan | |
| 2002/0070321 A1 | 6/2002 | Womack | |
| 2002/0153134 A1 | 10/2002 | Newman | |
| 2004/0056771 A1 | 3/2004 | Dungan | |
| 2006/0155486 A1 | 7/2006 | Walsh et al. | |
| 2007/0289635 A1 | 12/2007 | Ghazarian et al. | |
| 2008/0048853 A1 | 2/2008 | Leach et al. | |
| 2008/0082215 A1 | 4/2008 | McDowell | |
| 2008/0177678 A1 | 7/2008 | Martini et al. | |
| 2008/0231857 A1 | 9/2008 | Depeursinge et al. | |
| 2008/0278708 A1 | 11/2008 | Vaidya et al. | |
| 2008/0281528 A1 | 11/2008 | Relle, Jr. | |
| 2009/0089075 A1 | 4/2009 | Noujima et al. | |
| 2009/0319058 A1 | 12/2009 | Rovaglio et al. | |
| 2010/0094565 A1 | 4/2010 | Prince et al. | |
| 2010/0268480 A1 | 10/2010 | Prince | |
| 2010/0295673 A1 | 11/2010 | Ahmad | |
| 2011/0219891 A1 | 9/2011 | Mihaylov et al. | |
| 2012/0012066 A1 | 1/2012 | Beery et al. | |
| 2012/0109583 A1 | 5/2012 | Bartlett et al. | |
| 2012/0212347 A1 | 8/2012 | Boone | |
| 2012/0227983 A1 | 9/2012 | Lymberopoulos et al. | |
| 2012/0270205 A1 | 10/2012 | Patel et al. | |
| 2014/0058775 A1 | 2/2014 | Siig et al. | |
| 2014/0196788 A1 | 7/2014 | Taft | |
| 2014/0368354 A1 | 12/2014 | Skourlis | |
| 2015/0048232 A1 | 2/2015 | Hallauer et al. | |
| 2015/0185194 A1 | 7/2015 | Prince et al. | |
| 2015/0369013 A1 | 12/2015 | Weatherhead et al. | |
| 2016/0212508 A1 | 7/2016 | Guglielmo et al. | |
| 2016/0232612 A1 | 8/2016 | Spalenka et al. | |
| 2017/0130480 A1 | 5/2017 | Perkins | |
| 2017/0154509 A1 | 6/2017 | Prabhakar et al. | |
| 2017/0277829 A1 | 9/2017 | Weggler et al. | |
| 2017/0336281 A1 | 11/2017 | Waxman et al. | |
| 2018/0266933 A1 | 9/2018 | Tamraz et al. | |
| 2018/0266944 A1 | 9/2018 | Waxman et al. | |
| 2018/0283169 A1 | 10/2018 | Oguche et al. | |
| 2018/0284735 A1 | 10/2018 | Cella et al. | |
| 2019/0110444 A1 | 4/2019 | Boehm | |
| 2019/0166413 A1 | 5/2019 | Klinger et al. | |
| 2019/0206068 A1 | 7/2019 | Stark et al. | |
| 2019/0324435 A1 | 10/2019 | Cella et al. | |
| 2019/0360311 A1 | 11/2019 | Cardenas et al. | |
| 2019/0360924 A1 | 11/2019 | Macrelli et al. | |
| 2020/0005236 A1 | 1/2020 | Borgerson et al. | |
| 2020/0333307 A1 | 10/2020 | Armitage | |
| 2020/0355580 A1 | 11/2020 | Asher | |
| 2021/0072080 A1 | 3/2021 | Scott et al. | |
| 2021/0123768 A1 | 4/2021 | Rezvani et al. | |
| 2021/0397312 A1 | 12/2021 | Haupt et al. | |
| 2022/0034762 A1 | 2/2022 | Cyrus et al. | |
| 2022/0091026 A1 | 3/2022 | Scott et al. | |
| 2022/0107189 A1 | 4/2022 | Leen et al. | |
| 2022/0164877 A1 | 5/2022 | Kamkar et al. | |
| 2022/0244226 A1* | 8/2022 | Ctistis | G01N 30/74 |

(56) References Cited

U.S. PATENT DOCUMENTS

| | | |
|---|---|---|
| 2022/0277261 A1 | 9/2022 | Stollman et al. |
| 2023/0176023 A1 | 6/2023 | Wang et al. |

FOREIGN PATENT DOCUMENTS

| | | |
|---|---|---|
| CN | 207351764 U | 5/2018 |
| CN | 109521162 A | 3/2019 |
| CN | 110726431 A | 1/2020 |
| CN | 209979311 U | 1/2020 |
| CN | 112084231 A | 12/2020 |
| CN | 212159251 U | 12/2020 |
| CN | 113283630 A | 8/2021 |
| CN | 214667980 U | 11/2021 |
| CN | 214749208 U | 11/2021 |
| CN | 113919448 A | 1/2022 |
| CN | 111859800 B | 10/2022 |
| DE | 10226305 C1 | 10/2003 |
| DE | 102006034731 A1 | 1/2008 |
| EP | 1882917 A1 | 1/2008 |
| EP | 2687844 A2 | 1/2014 |
| EP | 3001115 A2 | 3/2016 |
| JP | 2001042052 A | 2/2001 |
| OA | 17633 A | 5/2017 |
| WO | 2011013803 A1 | 2/2011 |
| WO | 2022023226 A1 | 2/2022 |
| WO | 2022056152 A1 | 3/2022 |

OTHER PUBLICATIONS

U.S. Appl. No. 63/233,694, filed Aug. 16, 2021, Anna Ailene Scott.
U.S. Appl. No. 63/323,703, filed Mar. 25, 2022, Nathan C. Eichenlaub.
"Operational risk management in the energy industry," 2014, Management Solutions, 10 pages (Year: 2014).
Aber, James S. et al. Small-format aerial photography: Principles, techniques and geoscience applications Elsevier, 2010.
Center for Chemical Process Safety, "Guidelines for Chemical Process Quantitative Risk Analysis, Second Edition," "Chapter 1, Chemical Process Quantitative Risk Analysis," 2010, American Institute of Chemical Engineers, pp. 1-55 (Year: 2010).
Center for Chemical Process Safety, "Guidelines for Chemical Process Quantitative Risk Analysis, Second Edition," "Chapter 3, Event Probability and Failure Frequency Analysis," 2010, American Institute of Chemical Engineers, pp. 297-393 (Year: 2010).
Collier-Oxandale, et al., "Understanding the ability of low-cost MOx sensors to quantify ambient VOCs", Atmospheric Measurement Techniques, Mar. 5, 2019, pp. 1441-1460, vol. 12, Copernicus Publications on behalf of the European Geosciences Union, 20 pages.
Control Effectiveness, May 2014, Broadleaf Capital International Pty Ltd, 7 pages (Year: 2014).
Ebermann et al., "Design, Operation and Performance of a Fabry-Perot-Based MWIR Microspectrometer," access date: Nov. 9, 2018, pp. 1-6.
F. I. Khan et al., "Safety weighted hazard index (swehi) a new, user-friendly tool for swift yet comprehensive hazard identification and safety evaluation in chemical process industries," 2001, Transactions of the Institution of Chemical Engineers, vol. 79 Part B, 16 pages (Year: 2001).
Faisal I. Khan et al., "Multivariate hazard identification and ranking system," 1998, Process Safety Progress, vol. 17, No. 3, 14 pages (Year: 1998).
FAQ, Meet Clair Site, access date: Nov. 9, 2018, pp. 1-8.
International Search Report and Written Opinion for International Application No. PCT/US2021/049702, dated Feb. 7, 2022, 4 pages.
International Search Report and Written Opinion from the US International Search Authority for International Application No. PCT/US2020/012247 dated Mar. 10, 2020, 13 pages.
ISA/US, International Search Report and Written Opinion for PCT/US21/49702, 36 pages.
Jim Joy et al., "National minerals industry safety and health risk assessment guideline" 2007, http://www.nost.edu.au/cms_docs/286339_National_Minerals_Industry_Safety_and_Health_Risk_Assessment_Guideline_-_J im_Joy.pdf, 164 pages (Year: 2007).
JJS Technical Services, "BW Technologies Rig Rat III Gas Detector (Non-Wireless Version)", , retrieved from the Internet Jul. 19, 2019, 3 pages.
Maureen Hassall, "What is a control?," Aug. 31, 2015, 2015 NSW Mining-Health, Safety, Environment and Community Conference, 33 pages (Year: 2015).
Mohammad Javad Jafari et al., "The credit of fire and explosion index for risk assessment of iso-max unit in an oil refinery," 2012, International Journal of Occupational Hygiene, vol. 4, No. 1, pp. 10-16 (Year: 2012).
Restek Pure Chromatography "TO-Can Canister With Rave Valve cat.# 27416, 27417, 27418, 27419, 27420, 27421, 27422, 27423" Catalog #500-10-002 Date Oct. 2020.
S.M. Miri Lavasani et al., "Fuzzy risk assessment of oil and gas offshore wells," 2011, Process Safety and Environmental Protection , vol. 89, pp. 277-294 (Year: 2011).
Sam Mannan, "Lee's loss prevention in the process industries," 2012, Butterworth-Heinemann, 8 pages (Year: 2012).
Scott et al., "An Air Quality Sensor Network for Greater Baltimore," access date: Nov. 9, 2018, pp. 1-8.
Scott, Meet Clair Site, What causes trouble breathing indoors? blog, access date: Nov. 9, 2018, pp. 1-8.
U.S. Environmental Protection Agency, "Determination of Volatile Organic Compounds (VOCs) in Air Collected in Specially Prepared Canisters and Analyzed by Gas Chromatography—Mass Spectrometry (GC-MS)" Sep. 2019.
United States Environmental Protection Agency, "SPod Fenceline Sensors Under Development", , retrieved from the Internet Jul. 19, 2019, 1 page.
United States Environmental Protection Agency, "Tracking Emissions Using New Fenceline Monitoring Technology", published Jun. 18, 2018, , retrieved from the Internet Jul. 19, 2019, 3 pages.
Werden, Benjamin Seth "Chemical Source Apportionment of Ambient Particulate matter in the Kathmandu Valley, Nepal" Drexel University, 2021.
Wisconsin Department of Natural Resources, "Evaluation of Passive Sampling Techniques for Monitoring Roadway and Neighborhood Exposures to Benzene and Other Mobile Source VOCs" WDNR Publication AM-384 2007.
Zimmerman et al., Atmospheric Measurement Techniques, "A machine learning calibration model using random forests to improve sensor performance for lower-cost air quality monitoring," Jul. 25, 2017, pp. 291-313.

* cited by examiner

AIR QUALITY MONITORING SYSTEM AND METHOD

CROSS REFERENCE TO RELATED APPLICATIONS

This application is a continuation of U.S. patent application Ser. No. 18/205,445 filed on Jun. 2, 2023, entitled "AIR QUALITY MONITORING SYSTEM AND METHOD", which is a continuation of U.S. patent application Ser. No. 18/098,430, entitled "AIR QUALITY MONITORING SYSTEM AND METHOD" filed on Jan. 18, 2023 and issued on Sep. 12, 2023 as U.S. Pat. No. 11,754,495, which is a continuation of U.S. patent application Ser. No. 17/843,613 filed on Jun. 17, 2022 and issued on Feb. 28, 2023 as U.S. Pat. No. 11,592,390, which is Continuation of U.S. patent application Ser. No. 17/843,554, filed on Jun. 17, 2022 and issued on Feb. 21, 2023 as U.S. Pat. No. 11,585,752, entitled AIR QUALITY MONITORING SYSTEM AND METHOD, which is a continuation of U.S. patent application Ser. No. 17/541,693, filed on Dec. 3, 2021 and issued on Jun. 21, 2022 as U.S. Pat. No. 11,366,057, entitled "AIR QUALITY MONITORING SYSTEM AND METHOD" which is a continuation of PCT/US2021/049702, entitled "AIR QUALITY MONITORING SYSTEM AND METHOD" filed on Sep. 9, 2021.

This application is related to issued U.S. patent application Ser. No. 16/188,793, filed on Nov. 13, 2018 and issued on Apr. 28, 2020 as U.S. Pat. No. 10,634,558, entitled "AIR QUALITY MONITORING SYSTEM AND ENHANCED SPECTROPHOTOMETRIC CHEMICAL SENSOR," which is hereby expressly incorporated by reference in its entirety for all purposes.

This application is related to issued U.S. patent application Ser. No. 16/823,205, filed on Mar. 18, 2020 and issued on Dec. 29, 2020 as U.S. Pat. No. 10,876,890, entitled "AIR QUALITY MONITORING SYSTEM AND ENHANCED SPECTROPHOTOMETRIC CHEMICAL SENSOR," which is hereby expressly incorporated by reference in its entirety for all purposes.

The present application is related to issued U.S. patent application Ser. No. 16/953,908, filed on Nov. 20, 2020 and issued on Dec. 7, 2021 as U.S. Pat. No. 11,193,822, entitled "AIR QUALITY MONITORING SYSTEM AND ENHANCED SPECTROPHOTOMETRIC CHEMICAL SENSOR," which is hereby expressly incorporated by reference in its entirety for all purposes.

PCT/US2021/049702 and the present application claim priority to U.S. Patent Application Ser. No. 63/076,829, filed on Sep. 10, 2020, entitled "AIR QUALITY MONITORING SYSTEM, ENHANCED SPECTROPHOTOMETRIC CHEMICAL SENSOR, AND RELATED TECHNOLOGIES," which is hereby expressly incorporated by reference in its entirety for all purposes.

PCT/US2021/049702 and the present application claim priority to U.S. Patent Application Ser. No. 63/233,694, filed on Aug. 16, 2021, entitled "AIR QUALITY MONITORING SYSTEM AND Method", which is hereby expressly incorporated by reference in its entirety for all purposes.

A portion of the disclosure of this patent document contains material, which is subject to copyright and/or mask work protection. The copyright and/or mask work owner has no objection to the facsimile reproduction by anyone of the patent document or the patent disclosure, as it appears in the Patent and Trademark Office patent file or records, but otherwise reserves all copyright and/or mask work rights whatsoever.

TECHNICAL FIELD

This disclosure pertains generally, but not by way of limitation, to systems and methods for reducing fugitive emissions. In particular, the system(s) and method(s) described herein provide remote monitoring of facilities and/or equipment that often emit gasses.

BACKGROUND

Air quality is one of the most important factors that can affect the health of a population. Countries around the world spend significant resources on monitoring air quality and controlling air pollution. One of the major problems is that instruments that can accurately monitor air quality are expensive and typically require expertise to operate properly. Currently, air quality monitoring is mainly performed by government agencies and dedicated organizations using specialized instrumentation. As a result, general air quality data often does not provide the fidelity necessary to pinpoint issues at a scale smaller than a regional level. Real-time air quality monitoring at a finer scale may be cost prohibitive because air quality monitoring instruments can be expensive.

There are three types of sensing systems that are generally used for the measurement for detection of compounds in air: point sensors, line (including long open path) sensors and imaging sensors. These systems can be statically field-deployed, integrated into handheld devices, or mounted on various vehicles, such as automobiles, drones, and other unmanned aircraft (such as balloons), planes, helicopters, and other manned aircrafts, and on satellites. Static line or imaging sensors can also be mounted on motorized systems to point toward different fields of view of a site.

SUMMARY

Various illustrative configurations of air quality monitoring system and method are disclosed. The air quality monitoring system and method may detect and report pollution from monitored site for a variety of reasons (e.g., corporate performance, quality of environment, regulatory requirements, etc.). For example, a monitored site may be an oil facility removing natural gas (and/or oil) from an underground reservoir utilizes equipment (e.g., pumpjacks, holding tanks, valves, pipes, etc.) that requires maintenance. Occasionally, this equipment releases pollution into the atmosphere. This release into the atmosphere is called 'fugitive gas emission' or generically 'pollution' that should be detected and reported so corrective action may be taken.

To address emission/pollution, the disclosed system monitors, detects, and reports the differential concentrations of gas from a population of monitors located around the perimeter of a site. Differential concentrations of gas from a population (of monitors located in a monitored area) indicates presence of a leak. An oil facility configured with the present system can sense the increase/presence of emissions by comparing readings from a plurality of pollution monitors. Each pollution monitor utilizes a logic control system to read at least one pollution sensor; furthermore, the aggregation of pollution monitors presents the sensed site data to determine if there is a leak. The pollution leak can be addressed accordingly (e.g., noted, repaired, observed, etc.).

At least some embodiments are air quality monitoring systems configured for wide-scale deployment of monitors with enough accuracy for meaningful and actionable data. In one aspect, an advanced technique is used to calibrate low-precision gaseous chemical sensors to obtain accurate measurements by cross-calibrating those sensors to correct sensitivities to parameters that cause errors in measurement of targeted chemicals. In another aspect, air quality measurements are used to identify sources of chemicals at a localized level by accounting for local conditions using data such as ambient condition data and user-provided data about the local environment. In yet another aspect, a gaseous chemical sensor with an improved encasement having a cell for reflecting and lengthening light path is provided to reduce the limitations and enhance the accuracy of a conventional spectrophotometric gaseous chemical sensor.

The system and components described herein can reduce the resources (e.g., instrument setup time, cost, expertise) that are needed to deploy a large-scale air quality monitoring system and to increase fidelity of air quality data. Reducing the need for resources also enables new ways of gathering air quality data, such as by crowd-sourcing data from instruments deployed by non-expert users. The technology also serves to democratize air quality monitoring by making air quality instrumentation and analysis affordable to individual users.

In some embodiments, a system can monitor one or more sites based on air quality. The system can include one or more monitoring elements capable of obtaining information, including air information, weather information, environment information, user-inputted information, predictions, etc. The monitoring elements can be configured to detect, for example, the presence of gases, concentrations of gases, air characteristics, emissions, or the like. Based on the detection by the monitoring elements, the system provides analytics of the site(s). For example, the monitoring elements can be sensors that analyze air to detect emissions caused by equipment leaks at a site (e.g., gas production site, manufacturing site, recycling center, power plant, refinery, etc.). The system can be an air monitoring system that obtains information about airborne particulate matter, gaseous emissions, or other desired information.

The air quality monitoring system and components further relate to the quantification, qualification, and/or localization of airborne particulate matter or gaseous emissions in the atmosphere using one or more point sensors configured to detect, measure, and/or sense one or multiple target compounds and/or to other compounds present in the atmosphere. The air quality monitoring system may use as few as one static, point sensor system that measures gas concentration as well as one or more environmental conditions (e.g., weather conditions) to qualify, quantify, and/or localize emissions in a broad area around the sensor system. In one embodiment, the air quality monitoring system may rely on multiple measurements by the sensor system over time from a fixed location, together with a fluid mechanics-based atmospheric simulation of the deployment site which integrates the weather information collected by the sensor system to infer, using an inverse model, spatially resolved information about the emission location, composition, flux and/or other parameters of interest for facilitating maintenance, tracking asset integrity, and evaluating environmental, health and safety impacts. Using a reduced number of sensors to achieve quantification, localization and qualification of emissions is of importance to reduce the cost of the technology, which is the first barrier to mass adoption of real-time emissions monitoring systems. The monitoring system allows for the use of the time resolution of the sensing system to evaluate and enhance the spatial resolution (localization) of emissions sources and the precision of concentration maps (quantification) of allowed or fugitive emissions (qualification). Further, the monitoring system proposes an enhanced, adaptive deployment method for sensor networks using site information to minimize the number of sensor systems to be deployed while meeting the site operator requirements regarding detection, quantification, qualification, and localization. Additional specific sensor system embodiments and methods for denoising and analyzing absorption spectra for improving speciation and long-term remote calibration and accuracy of a field-deployed spectrometer are disclosed.

With regard to detection, the method and sensor system has detection capabilities via adaptively modifying alert thresholds based on localization, quantification, and/or qualification of emissions.

With regard to localization, the system and methods can produce the required spatial resolution by using intensive modeling. An inverse problem strategy is employed, using frequent measurements of target compound concentrations, and co-located and contemporaneous weather data with a detailed simulation model integrating the fluid mechanics of the atmosphere around and in the site.

A single point sensor system can be used to spatially resolve the site and localize the emission sources. This localization is constructed over time by analyzing the concentration measured by the system configured with a point sensor in various weather conditions. The simulation allows a level of fidelity that is not possible through wind back-tracing, instead the present(s) system and method(s) integrates effects from weather, turbulence, terrain rugosity, obstacles and topology, and equipment geometry on the transport of the compound. This is particularly necessary for large sites such as landfills or other diffuse area sources of target compounds where wind patterns are influenced by the terrain (i.e., the landfill mound itself) and where the localization includes identifying hotspots amid diffuse sources.

With regard to qualification, multiple methods are proposed for the evaluation of the type and composition of emissions, particularly to separate fugitive emissions from operational emissions and to qualify emissions from diffuse sources. The emission qualification with respect to composition is possible in some embodiment of the disclosure using broadband spectrometry. The emission qualification with respect to type, for instance routine versus fugitive emission, is obtained by performing a statistical analysis of the detected emissions based on their source, magnitude, and frequency, compared to the source, magnitude, and frequency of routine emissions. The probability of an emission being due to unintended operations can be derived by statistical inference (i.e., a deviation from the 'routine' emission profile).

Specific methods for enhancing the selectivity, calibration, precision, and accuracy of measuring the concentration of compounds absorbing light in the mid-infrared range of the electromagnetic spectrum using a broadband, low spectral resolution spectrophotometer are proposed. Although the method may be detailed with respect to a specific sensor technology embodiment, this is not intended to limit the disclosure to spectrophotometers since other types of sensors available on the market can be used in the general method for the quantification, qualification, localization, and detection of emissions in an atmospheric context.

In one embodiment, the system uses a broadband absorption spectrophotometer as the point sensor. This spectrophotometer has a low spectral resolution, which means that the profile of the gas is detectable, but not the fine structure. Therefore, it is not possible to simply use peak amplitude to infer a compound concentration because many compounds may absorb that wavelength. The system and method include a wavelet-based method that enhances selectivity, accuracy, and precision by integrating sensor-specific information in pre-processing and identification of the mixture composition and concentrations. In particular, the method can help distinguish unknown compounds in the mixture even if such a compound interferes with the target compound absorption profile.

It can be difficult to quantify the flux, emission mass or rate, or size of a target gas emission event. This is because it is difficult to relate a certain concentration to an emission mass or rate. Based on weather conditions, the location of the emission source (with respect to the sensor) and emission characteristics (temperature/pressure differential, diffusivity of the compound, etc.) of a certain measured concentration may not directly relate to the emission mass, flux, or volume. The relationship between the concentration measurement and the flux, volume, or mass of the emission is therefore established by defining a model, which depends on the type of sensing technology that is used.

In certain cases, plume theory is used as the model. For point systems, the concentration of the target gas can be calculated by taking measurements at various positions across a transversal section of the emission plume. This can be done by using a dense network of point measurements with static point sensors. For line sensors, a single sensor can be used if the wind conditions are favorable and the pathlength completely passes across the plume. For mobile sensors, a single point sensor can be moved across the plume to form either a point cloud or a line across the plume. The objective is to measure an instantaneous cross section of the plume such that the mass-flow conservation principle can be applied. Extrapolation or models can be used to fully integrate the plume cross section where measurements are not available. For example, a line measurement across the plume together with a Gaussian plume model approximation and some estimate of wind speed and direction can be used to estimate the flux.

The present disclosure discloses a method for determining concentrations from a specific embodiment of the sensor technology and also methods for evaluating the flux, mass, and/or volume of emissions of a target gas. Two methods are provided as examples. One method is based on the inverse model, where the transport problem is explicitly defined and the relation between flux, location, and concentration is obtained based on the weather conditions and the simulation results. Another, simpler method is based on wind direction and speed alone, where the wind direction is used instead of movement to create a cross section of the plume. The second method relies on a simplification assumption and may not be usable in all conditions. In particular, the second method will be less accurate than the first method (inverse method) when turbulence dominates the transport of airborne gases, such as methane and when the source of such gases is too close to the sensor.

There are several strategies to deploy point sensor networks. Sensor networks known in the industry focus on the network effect on some sensor characteristics by the redundancy of measurement between multiple sensors. For example, this is the strategy taken for obtaining localization using point sensors in most industry references. The system and methods disclosed take the opposite approach, the objective being instead to minimize superimposition of the detection ranges of the sensors of the network, and to maximize coverage of potential sources while minimizing the number of sensors used. The goal is to meet the network requirements using the least resource(s). In one embodiment, a method is proposed which fully characterizes the detection area of the sensor system based on not only the sensor characteristics (detection limit, compounds detectable, frequency of measurement), but also project characteristics (fraction of emissions to be detected, localization requirement, report frequency requirement), site characteristics (location of equipment in the field, terrain topology, terrain cover and roughness, historical weather patterns, area where the sensor can actually be deployed, and restricted deployment area), and/or prior network data (if a prior deployment configuration was in place).

Once the detection area for a sensor in the field is characterized, a method is used to dynamically optimize the position of the sensor network that minimizes the number of sensor systems. For example, in upstream oil and gas, oil fields extend over large areas and are covered with hundreds of well pads. A network of sensors can be used to detect emissions across multiple well pads or well pad equipment groups with a single sensor. Each sensor is defined by a detection range, the shape and extent of which depends on the detection limit of the sensor unit, the smallest emission size to be detected (inferred by the fraction of emission to be detected), the diffusivity of the emission compound, and the wind speed. The terrain and surface roughness and land cover further influence the detection range, as well as the principal wind direction of the specific site (some wind directions can be only rarely observed). The localization is defined at the lowest level by the ratio of the distance separating two sources and the distance to the sensor. If two sources are too close together, the measurement and/or simulation may not be able to distinguish between them. Likewise, angular discrimination may matter; for example, if a small source is occulted by a larger, closer source and is close to being in the direction from the sensor. Based on the field information and the project characteristics, the position of the sensor is optimized by an algorithm that minimizes the amount of redundant information captured by the sensors measurement and maximizes the project objectives.

The detection, quantification, qualification, and localization of emissions is not always sufficient to provide the necessary actionable information about emitters of the target compounds in the environment; the operator may for instance lack the processes to seamlessly integrate such emission information into their standard operation methodology and work practices. What may be ascertained in the detection, quantification, qualification, and localization of emissions does not address operational integration and ultimately the utility of such emission information. Disclosed are specific methods for operational integration of the emission information. In particular, a maintenance triaging and tracking methodology as well as an emission abatement tracking methodology are proposed. Also disclosed is an actionability engine that proposes appropriate responses to the emissions and learns from maintenance practices over time.

The air quality monitoring system may focus on, without being limited to, anthropogenic and natural sources of atmospheric emissions. This is of particular interest in oil and gas applications such as at oil and gas extraction pads, in chemical production and transport activities, agricultural activities, and in the solid waste industry. The systems and methods described makes static, real-time monitoring more accurate and affordable.

In one configuration, a computer-implemented method of identifying a target emission at a site using a plurality air quality monitoring each implementing chemical sensors is disclosed. The method may include creating at least one simulation model for the site based on simulation parameters. The simulation parameters may include at least two of a wind direction, a wind speed, an air pressure, an air temperature, a number of potential emission sources, a location of each of the potential emission sources, a source flux associated with each of the potential emission sources, a surface concentration, a weather condition, a hygrometry data, and an altitude. The method may include obtaining actual parameters for the site corresponding to the simulation parameters, and receiving actual emissions measurements from a plurality of air quality monitors deployed at the site associated with the actual parameters for the site. The plurality of air quality monitors may be deployed at predefined locations at the site. The method may further include identifying a relevant simulation model from the at least one simulation model, wherein simulation parameters associated with the relevant simulation model match with the actual parameters, extracting virtual emissions measurements generated by the relevant simulation model. The method may further include receiving actual emissions measurements from the plurality air quality monitors deployed at the site associated with the actual parameters for the site, correlating the virtual emissions measurements with the actual emissions measurements from the plurality air quality monitors, and determining configuration of at least one emission source based on the correlation. The configuration of emission sources may include a location of the emission source at the site and a concentration of emissions from the emission source.

In another configuration, a computer-implemented method for identifying a source of a target chemical at a site is disclosed. The method may include providing at least a predominate air quality monitor including a first sensor responsive to the target chemical, and a first location at which a predominate air quality monitor is located. The method may further include measuring a first concentration of the target chemical at the predominate air quality monitor as a function of a wind speed a wind direction. The wind speed and the wind direction may be measured using a wind sensor. The method may further include providing a plume of the target chemical. The plume may include a horizontal distribution deviation defined as a standard deviation of a horizontal distribution of a plume concentration and a vertical distribution deviation defined as a standard deviation of a vertical distribution of the plume concentration. The method may further include creating at least one simulation model for the site based on the above-mentioned simulation parameters. The method may further include identifying an emission rate of the target chemical at the source using the simulation model functionally operated by the standard deviation of horizontal distribution, the standard deviation of vertical distribution, the first concentration at the predominate air quality monitor, and the wind speed. The identified source may be outputted to a computer device.

In another configuration, a method of installing an air quality monitor system at a site is disclosed. The method may include surveying the site by procuring an equipment log of a plurality of leak-prone equipment at the site, a centroid of the leak-prone equipment, and a wind-rose diagram representative of wind at the site. The method may further include attaching the wind-rose diagram to the site. The wind-rose diagram may include a predominate downwind direction, a secondary downwind direction angularly offset from the predominate downwind direction, and a tertiary downwind direction angularly offset from the predominate downwind direction and oppositely disposed from the secondary downwind direction. The method may further include installing a predominate air quality monitor in the predominate downwind direction from the centroid at a location where the predominate air quality monitor has a maximal angular separation between the leak-prone equipment, installing a secondary air quality monitor in the secondary downwind direction from the centroid where the secondary air quality monitor has minimal observational overlap with the predominate air quality monitor, and installing a tertiary air quality monitor in the tertiary downwind direction from the centroid where the tertiary air quality monitor has minimal observational overlap with the predominate air quality monitor and with the secondary air quality monitor.

In yet another configuration, a method of determining a plume flux of a plume of emissions at a site is disclosed. The method may include receiving a predetermined number of samples, by a plurality of air quality monitors installed at the site, of the plume at a plurality of angles of the plume, registering an associated concentration point based on the plurality of angles, and obtaining a fit of a point cloud. When measurements occur in idealized conditions site parameters, the method may include calculating the plume flux using a mass conservation equation by multiplying an area concentration of the plume cross section by its normal speed and by estimating the plume concentration in a height direction.

In another configuration, a method of transmitting data from an air quality monitor is disclosed. The method may include providing a memory in the air quality monitor, and providing an emissions sensor in the air quality monitor. The emissions sensor may be configured to obtain sensor data at a predefined frequency. The memory may be configured to store sensor data obtained by the emissions sensor. The air quality monitor may be configured to transmit the sensor data to a cloud-base database. The method may further include detecting a low-connectivity condition, and upon detecting the low-connectivity condition, starting to store the sensor data in the memory. Further, the method may include detecting a normal-connectivity condition, and upon detecting the normal-connectivity condition, transmitting the sensor data stored in the memory to the cloud-based database.

In yet another configuration, a system of one or more computers can be configured to perform particular operations or actions by virtue of having software, firmware, hardware, or a combination of them installed on the system that in operation causes or cause the system to perform the actions. One or more computer programs can be configured to perform particular operations or actions by virtue of including instructions that, when executed by data processing apparatus, cause the apparatus to perform the actions. One general aspect includes a computer-implemented method for identifying a source of a target chemical. The computer-implemented method also includes providing at least a predominate air quality monitor may include: a first sensor responsive to the target chemical. The method also includes a first location at which the predominate air quality monitor is located. The method also includes measuring a first concentration of the target chemical at the predominate air quality monitor as a function of a wind speed and/or a wind direction. The method also includes where the wind speed and the wind direction are measured using a wind sensor. The method also includes providing a plume of the target chemical, the plume may include a horizontal distribution deviation defined as a standard deviation of a horizontal distribution of a plume concentration. The method also includes a vertical distribution deviation defined as a standard deviation of a vertical distribution of the plume concentration. The method also includes identifying an emission rate of the target chemical at the source using a plume model functionally operated by a standard deviation of horizontal distribution. The method also includes a standard deviation of vertical distribution. The method also includes the concentration at the predominate air quality monitor. The method also includes the wind speed. The method also includes further identifying the source from a plurality of possible sources of the target chemical by correlating the emission rate. The method also includes outputting the identified source to a computer device. The method also includes providing a cloud server. The method also includes where the predominate air quality monitor further may include a processor. The method also includes an averaging routine operatively associated with the processor. The method also includes averaging a series of the first concentration of the target chemical to generate an averaged first concentration, according to at least one of a) with the processor at the predominate air quality monitor, b) according to the averaging routine, and c) before transmitting the averaged first concentration to the cloud server. The method also includes after transmitting the first concentration to the cloud server, bootstrapping a plurality of the first concentration.

In another configuration, a computer-implemented method for identifying a source of a target chemical. The computer-implemented method also includes providing at least a predominate air quality monitor may include a first sensor responsive to the target chemical. The method also includes a first location at which the predominate air quality monitor is located. The method also includes measuring a first concentration of the target chemical at the predominate air quality monitor as a function of: a wind speed and/or a wind direction. The method also includes where the wind speed and the wind direction are measured using a wind sensor. The method also includes providing a plume of the target chemical, the plume may include a horizontal distribution deviation defined as a standard deviation of a horizontal distribution of a plume concentration. The method also includes a vertical distribution deviation defined as a standard deviation of a vertical distribution of the plume concentration. The method also includes identifying an emission rate of the target chemical at the source using a plume model functionally operated by a standard deviation of horizontal distribution. The method also includes a standard deviation of vertical distribution. The method also includes the concentration at the predominate air quality monitor. The method also includes the wind speed. The method also includes further identifying the source from a plurality of possible sources of the target chemical by correlating the emission rate. The method also includes outputting the identified source to a computer device. The method also includes providing a cloud server. The method also includes where the predominate air quality monitor further may include a processor. The method also includes an averaging routine operatively associated with the processor. The method also includes averaging a series of the first concentration of the target chemical to generate an averaged first concentration, according to at least one of a) with the processor at the predominate air quality monitor, b) according to the averaging routine, and c) before transmitting the averaged first concentration to the cloud server. The method also includes after transmitting the first concentration to the cloud server, filtering a population of the first concentration to identify cyclical emissions that are dependent on at least one of a time of day and/or a day of month. The method also includes a month of year. The method also includes temperature. The method also includes wind direction. Other embodiments of this aspect include corresponding computer systems, apparatus, and computer programs recorded on one or more computer storage devices, each configured to perform the actions of the methods.

In yet another configuration, one general aspect includes a computer-implemented method for identifying a source of a target chemical. The computer-implemented method also includes providing at least a predominate air quality monitor may include a first sensor responsive to the target chemical. The method also includes a first location at which the predominate air quality monitor is located. The method also includes measuring a first concentration of the target chemical at the predominate air quality monitor as a function of a wind speed. The method also includes a wind direction. The method also includes where the wind speed and the wind direction are measured using a wind sensor. The method also includes providing a plume of the target chemical, the plume may include a horizontal distribution deviation defined as a standard deviation of a horizontal distribution of a plume concentration. The method also includes a vertical distribution deviation defined as a standard deviation of a vertical distribution of the plume concentration. The method also includes identifying an emission rate of the target chemical at the source using a plume model functionally operated by a standard deviation of horizontal distribution. The method also includes a standard deviation of vertical distribution. The method also includes the concentration at the predominate air quality monitor. The method also includes the wind speed. The method also includes further identifying the source from a plurality of possible sources of the target chemical by correlating the emission rate. The method also includes outputting the identified source to a computer device. The method also includes providing a cloud server. The method also includes transmitting a population of the first concentration to the cloud server. The method also includes identifying a highest first concentration of the population of the first concentration. The method also includes identifying a lowest first concentration of the population of the first concentration. The method also includes determining a signal-to-noise threshold. The method also includes dividing the first concentration by a difference between the highest first concentration and the lowest first concentration to produce a signal-to-noise ratio. The method also includes discarding individual readings of the first concentration that has a signal-to-noise ratio below the signal-to-noise threshold. Other embodiments of this aspect include corresponding computer systems, apparatus, and computer programs recorded on one or more computer storage devices, each configured to perform the actions of the methods.

In another configuration, one general aspect includes a computer-implemented method for identifying a source of a target chemical. The computer-implemented method also includes providing at least a predominate air quality monitor may include a first sensor responsive to the target chemical. The method also includes a first location at which the predominate air quality monitor is located. The method also includes measuring a first concentration of the target chemical at the predominate air quality monitor as a function of a wind speed and/or a wind direction. The method also includes where the wind speed and the wind direction are measured using a wind sensor. The method also includes providing a plume of the target chemical, the plume may include a horizontal distribution deviation defined as a standard deviation of a horizontal distribution of a plume concentration. The method also includes a vertical distribution deviation defined as a standard deviation of a vertical distribution of the plume concentration. The method also includes identifying an emission rate of the target chemical at the source using a plume model functionally operated by a standard deviation of horizontal distribution. The method also includes a standard deviation of vertical distribution. The method also includes the concentration at the predominate air quality monitor. The method also includes the wind speed. The method also includes further identifying the source from a plurality of possible sources of the target chemical by correlating the emission rate. The method also includes outputting the identified source to a computer device. The method also includes providing a cloud server. The method also includes where the predominate air quality monitor further may include a processor. The method also includes an averaging routine operatively associated with the processor. The method also includes averaging a series of the first concentration of the target chemical to generate an averaged first concentration, according to at least one of a) with the processor at the predominate air quality monitor, b) according to the averaging routine, and c) before transmitting the averaged first concentration to the cloud server. The method also includes the averaging to generate the averaged first concentration is dependent on either the wind speed or the wind direction. The method also includes the averaging to generate the averaged first concentration is increased when either the wind speed decreases below a diffusion-only speed or. the wind direction indicates delivery of dry air to the predominate air quality monitor.

Further areas of applicability of the present disclosure will become apparent from the detailed description provided hereinafter. It should be understood that the detailed description and specific examples, while indicating various configuration, are intended for purposes of illustration only and are not intended to necessarily limit the scope of the disclosure.

BRIEF DESCRIPTION OF THE DRAWINGS

The accompanying figures of the drawing, which are included to provide a further understanding of general aspects of the system/method, are incorporated in and constitute a part of this specification. These illustrative aspects of the system/method, and together with the detailed description, explain the principles of the system. No attempt is made to show structural details in more detail than is necessary for a fundamental understanding of the system and various ways in which it is practiced. The following figures of the drawing include.

In the appended figures, similar components and/or features may have the same reference label. Further, various components of the same type may be distinguished by following the reference label by a dash and a second label that distinguishes among the similar components. If only the first reference label is used in the specification, the description is applicable to any one of the similar components having the same first reference label irrespective of the second reference label. Where the reference label is used in the specification, the description is applicable to any one of the similar components having the same reference label.

DETAILED DESCRIPTION

Illustrative configurations are described with reference to the accompanying drawings. Wherever convenient, the same reference numbers are used throughout the drawings to refer to the same or like parts. While examples and features of disclosed principles are described herein, modifications, adaptations, and other implementations are possible without departing from the spirit and scope of the disclosed configurations. It is intended that the following detailed description be considered as exemplary only, with the true scope and spirit being indicated by the following claims.

Figure 1:
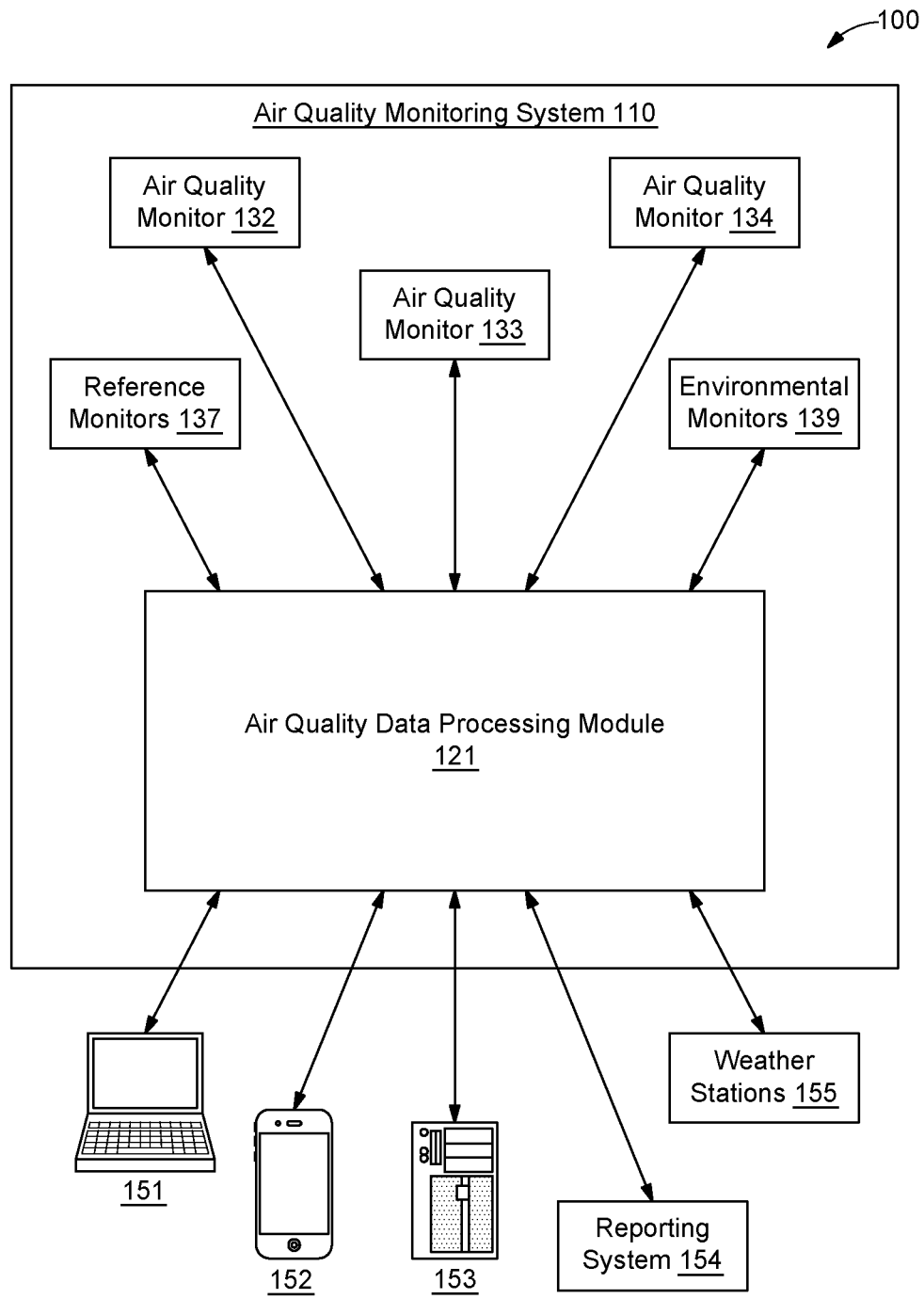
FIG. 1 illustrates an example of an air quality monitoring system, in accordance with an illustrative configuration of the present disclosure.

FIG. 1 shows an example of an air quality monitoring system 110, which handles air quality data from different sources. As illustrated in FIG. 1, air quality monitoring system 110 may include an air quality data processing module 121, a plurality of air quality monitors 132-134, reference monitors 137 and environmental monitors 139. Air quality monitors 132-134 can include one or more chemical sensors configured to detect and measure chemicals, such as ozone, nitrogen oxide, carbon dioxide, sulfur dioxide, volatile organic compounds, methane or other hydrocarbons, and other chemicals in gaseous state (these are herein being described as gaseous chemicals), as well as one or more particle sensors configured to detect and measure the presence of suspended particles in air such as dust, smoke, pollen, or soot (these are herein described as particulate matter or PM). Air quality monitors 132-134 may include an enhanced gaseous chemical sensor having a multi-pass cell for light rays, as will be described in more detail below, such as in conjunction with FIG. 6. Air quality monitors 132-134 may be located at multiple different locations. For example, multiple monitors may be located around a sizable area, such as a county, a city, or a neighborhood. Several instruments may also be located within a building or a dwelling.

Reference monitors 137 include precision gaseous chemical sensors and are configured to provide measurements for use in calibrating the gaseous chemical sensors in air quality monitors 132-134. Environmental monitors 139 are configured to measure environmental conditions, such as humidity, temperature, atmospheric pressure, air density, ambient light, geographic location, wind speed and direction, and the like.

Air quality data processing module 121 is configured to communicate with air quality monitors 132-134, reference monitors 137, and environmental monitors 139. For example, air quality data processing module 121 may receive data from these monitors, such as measurements. Air quality data processing module 121 may also transmit data to these monitors, such as providing calibration data. Air quality data processing module 121 can correct measurements from air quality monitors 132-134 using cross-calibration factors, as will be explained below. Air quality data processing module 121 is also configured to process the data from monitors and perform analyses to calculate or infer additional air quality data such as the amount of various gaseous chemicals in various locations, sources of those gaseous chemicals, and recommendations based on elicited requirements or preferences of end users. Air quality data processing module 121 is configured to communicate with mobile devices 152, computing devices 151 and server devices 153 to receive data and provide received, calculated, and inferred air quality data. For example, air quality data processing module 121 may receive user-input data and use that data to derive additional air quality data relevant to the area of analysis. Air quality data processing module 121 is also configured to communicate with other sources of data such as reporting system 154 and weather stations 155. Air quality data processing module 121 may be implemented in any appropriate physical or virtual computing platform (such as a networked server) and may operate and act through any suitable interface (such as a cloud computing platform).

Air quality monitoring system 110 may also be configured to process incoming data to provide a variety of outputs. For example, air quality monitoring system 110 may analyze measurements from air quality monitors 132-134 to determine sources of the gaseous chemicals being detected. Air quality monitoring system 110 may provide actionable steps to affect the chemical sources, such as ways to reduce the release of those chemicals or ways to minimize exposure to those chemicals, making use of stated preferences or user requirements, and/or ancillary (e.g., topological, geological, meteorological, demographic) datasets relevant to the area of investigation. The air quality monitoring system 110 can be used to quantify, qualify and/or localize sources, as discussed in connection with FIGS. 12-16.

Figure 2:
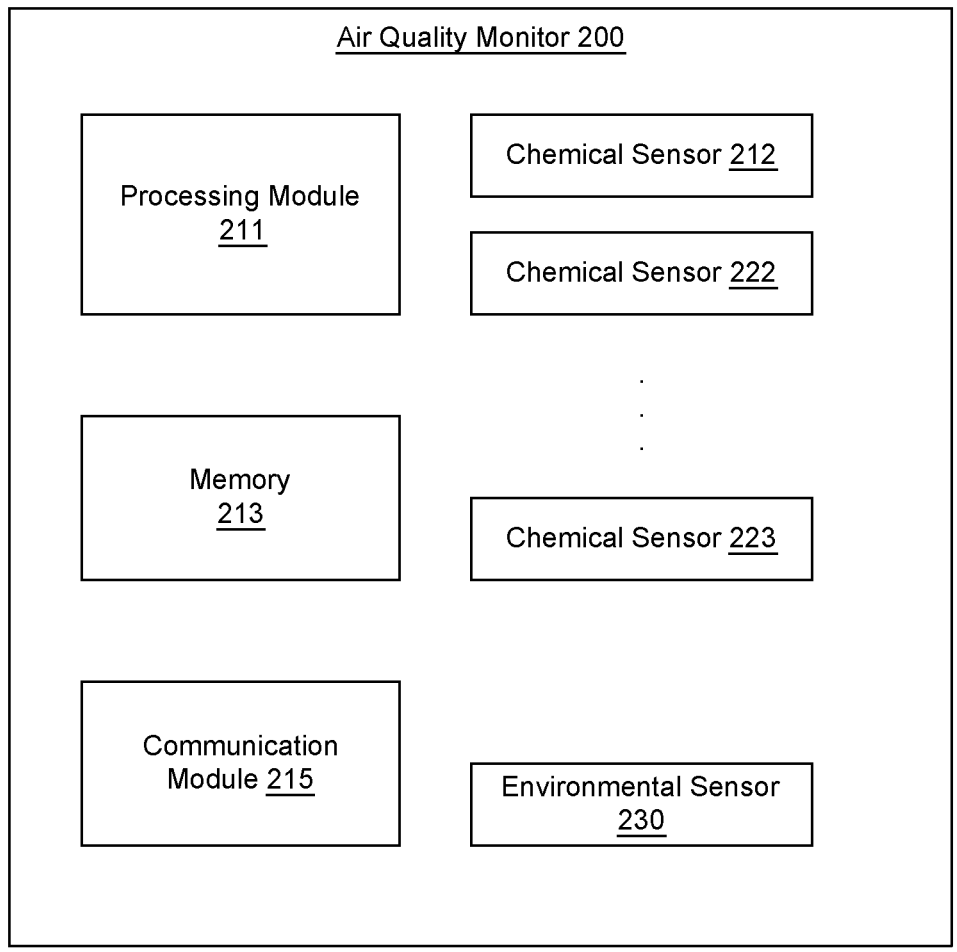
FIG. 2 illustrates an example air quality monitor and select example components that may be included, in accordance with an illustrative configuration of the present disclosure.

FIG. 2 shows an example air quality monitor 200 (such as air quality monitors 132-134 in FIG. 1) and some example components that may be included therein. Air quality monitor 200 may include processing module 211, memory 213, communication module 215, and one or more gaseous chemical sensors, such as chemical sensors 221-223, and environmental sensor 230. Processing module 211 processes computing tasks and controls other components. The computing tasks may include calibration. Memory 213 stores data, such as measurement data from gaseous chemical sensors 221-223 and calibration data such as cross-calibration factors. Chemical sensors 221-223 are configured to measure gaseous chemicals and particulates in analyte gas, such as gas under sampling by air quality monitor 200. Environmental sensor 230 measures environment conditions, such as temperature, pressure, humidity, location, wind speed, and the like. Communication module 215 handles communication with other devices. For example, communication module 215 may handle communication between air quality monitor 200 and air quality data processing module 121 of FIG. 1, other air quality monitors, user-devices such as mobile devices 152 and computing devices 151 and 153, and the like. Communication module 215 may communicate through any of a variety of wired and wireless mechanisms, such as Wi-Fi, Bluetooth, mobile networks, long-range radio, satellite, and the like. Air quality monitor 200 may also be configured to measure time, position, and other relevant information for computing devices. The components, functionality, and configuration of the sensor can be selected based on desired monitoring capabilities.

Figure 3:
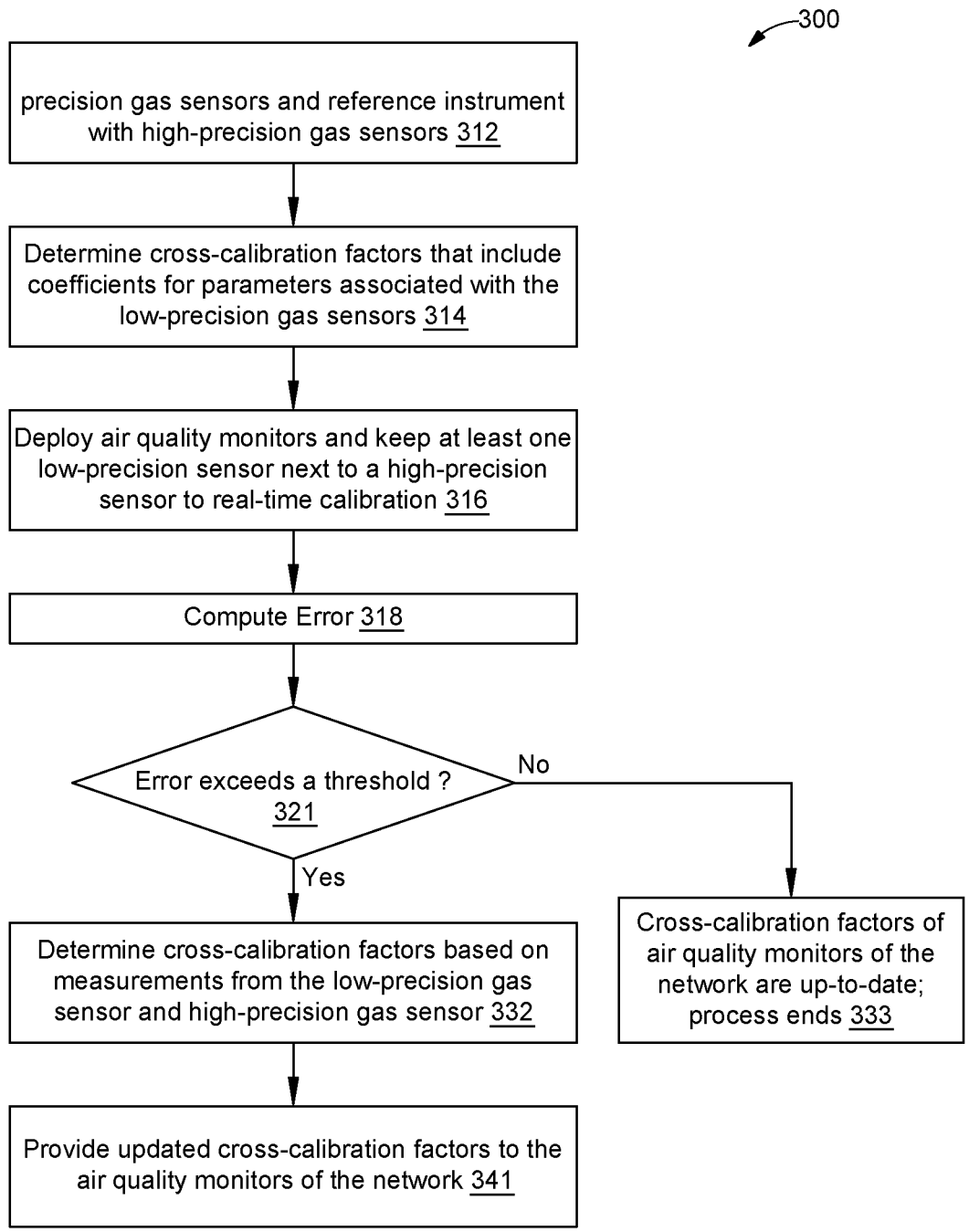
FIG. 3 illustrates a flow chart of an example cross-calibration method for calibrating a gaseous chemical sensor in an air quality monitor, in accordance with an illustrative configuration of the present disclosure.

Sensor Calibration Process: Air quality monitoring system 110 of FIG. 1 may be configured to increase the accuracy of low-precision gaseous chemical sensors through cross-calibration. Operators of air quality monitoring system 110 may implement a cross-calibration method 300 as shown in FIG. 3. This cross-calibration method 300 can improve the accuracy of low-precision gaseous chemical sensors, which are sensitive to both their target gas as well as additional parameters, including (but not limited to) other gases, changes in environmental conditions (wind, pressure, humidity/moisture), or e.g., radio waves. Cross-calibration method 300 calculates sensitivity of one of the gaseous sensors to the target gas as well as confounding factors and deduces the true value of the target gas by, for example, placing air quality monitors with low-precision gaseous chemical sensors next to a reference monitor with high-precision sensors.

Example equations for calculating cross-calibration factors and errors for calibration are shown below. According to the cross-calibration method, a low-precision sensor tasked with measuring a gas concentration X is sensitive to additional parameters $y_1, y_2, \ldots, y_n$, as illustrated in equation 1. In practice, one or more air quality monitors and one or more reference monitors may be used. The air quality monitors with low-precision gas sensors are placed next to reference monitors with high precision gas sensors which are not sensitive to these additional parameters. The calibration method determines the concentration of gas X as a function of the measured concentration $y_0$ and additional parameters $y_1, y_2, \ldots, y_n$ using the following equation. Coefficients $a_0, a_1, \ldots, a_n$ are determined where these coefficients represent sensitivity of the low precision sensor to parameter $y_1, y_2, \ldots, y_n$.

$$y_0 = a_0 X + a_1 y_1 + a_2 y_2 + \ldots + a_n y_n$$

After the air quality monitors are deployed in the network, an air quality monitor with low-precision gaseous chemical sensors may be placed next to a reference monitor with high-precision gaseous chemical sensors. The error between the high-precision monitor and the low-precision monitor may be calculated using the following equation:

$$\epsilon = X' - \frac{1}{a_0}(y_0 - a_1 y_1 - \ldots - a_n y_n)$$

If the error is nonzero, the cross-calibration method is performed for this pair of low-precision sensor and reference sensor. The difference in original and updated parameters $y_1, \ldots, y_n$ is reported and then pushed to devices on the network. For a naive implementation, only the error E is applied as a correction to the network of air quality monitors with similar low-precision gaseous chemical sensors, though more involved methods may be used.

Figure 4A:
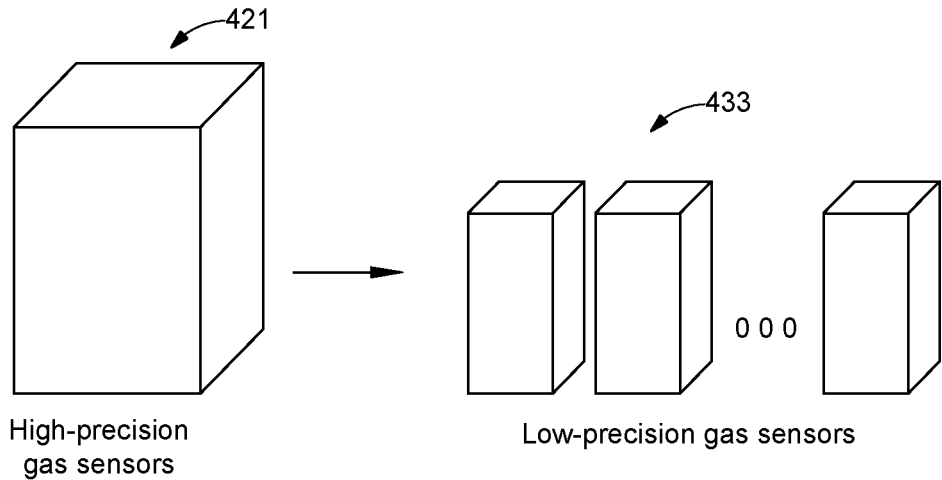
FIG. 4A illustrates an overview of sensor calibration, in accordance with an illustrative configuration of the present disclosure.

In the air quality monitor network, cross-calibration method 300 can be implemented by first placing each of the air quality monitors next to a reference monitor to calculate coefficients of the parameters for calibration. As described in step 312, and illustrated in FIG. 4A, cross-calibration begins by co-locating low-precision gaseous chemical sensors and high-precision gaseous chemical sensors. These sensors can be co-located using any of a variety of different configurations, such as by themselves, while incorporated in air quality monitors and reference monitors, a mix of different configurations, and the like.

At step 314, cross-calibration factors are determined. Cross-calibration factors may include coefficients for parameters associated with the low-precision gaseous chemical sensors. These cross-calibration factors may be implemented in any of a variety of ways and data structures, such as being simple values of the coefficients, combining the coefficients with the parameters, as an array of values, and the like. These cross-calibration factors may be used by individual air quality monitors, air quality data processing modules, other systems to calibrate and correct measurements of low-precision sensors of air quality monitors, and the like.

Figure 4B:
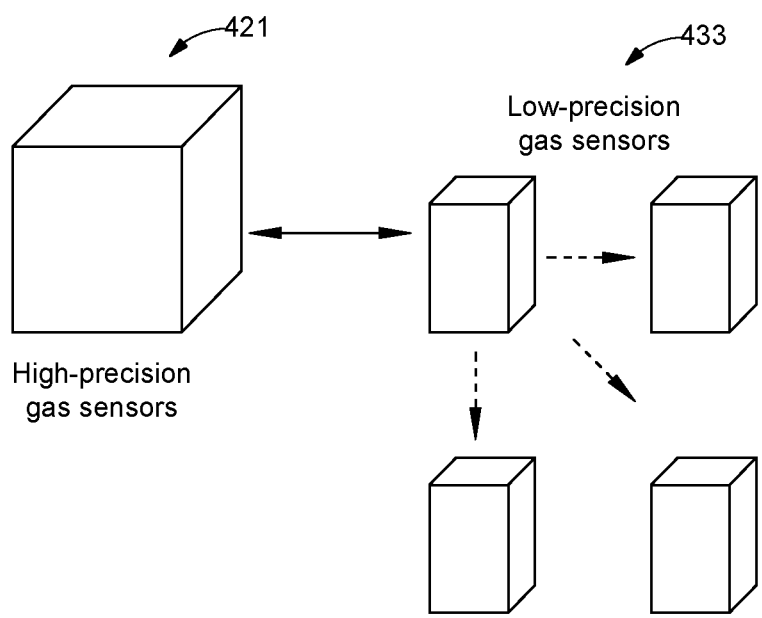
FIG. 4B illustrates an overview of sensor calibration update, in accordance with an illustrative configuration of the present disclosure.

At step 316, the air quality monitors are deployed in the network. As shown in FIG. 4B, one or more selected low-precision gas sensors 433 may be kept in proximity to one or more reference monitors 421 for updating cross-calibration after deployment.

Cross-calibration method 300 of FIG. 3 can calculate updated coefficients in real-time and apply that update to the network of air quality monitors. For example, at step 318, an error is computed to determine if the cross-calibration factors require an update. The error may be calculated using example equation 2 and as discussed above.

At decision step 321 of FIG. 3, a determination is made whether the error exceeds a threshold. An error that exceeds a threshold indicates that the cross-calibration factors may require an update. If the error exceeds the threshold and an update is needed, method 300 moves to step 332 where the cross-calibration factors are updated based on measurements from the low-precision gaseous chemical sensor and high-precision gaseous chemical sensor that were co-located after deployment for calibration updating purpose, as discussed in connection with step 316 and FIG. 4B. At step 341, the updated cross-calibration factors are provided to the air quality monitors of the network and the process ends.

Back at decision step 321, if the error is below the threshold, method 300 moves to step 333 where cross-calibration factors of air quality monitors of the network are up to date and the process ends.

Cross-calibration method 300 above may be implemented in any of a variety of different ways by different devices in many combinations. For example, air quality data processing modules may implement this process to initially calibrate the air quality monitors by determining the cross-calibration factors and then updating the air quality monitors on a periodic basis. The air quality data processing module may correct data received from the deployed air quality monitors based on the updated cross-calibration factors, push these updated factors to the deployed air quality monitors so that the monitors can update the data before sending these data to the air quality data processing module and other devices, a combination of correction steps, and the like.

One or more steps of the cross-calibration method 300 can be used to calibrate other types of sensors. Output from non-gas sensors can be used to further calibrate the gas sensors. For example, the method 300 can be used to calibrate wind sensors by, for example, using wind sensors rather than gas sensors. High-precision wind sensors and low precisions sensors can be employed. The cross-calibration method 300 can be modified based on the sensor characteristics and desired level of precision.

Gas Sensors Calibration Examples: The below examples illustrate some possible implementation scenarios of the calibration process and example capabilities of the air quality monitoring system.

Calibration Example 1: A low-precision ozone sensor is sensitive to rapid changes in humidity and nitrogen dioxide. Using a high-precision instrument, the process calculates sensitivity of the sensor to ozone, humidity changes, and nitrogen dioxide. The process uses these values to eliminate humidity changes and nitrogen dioxide from the values returned by the low-precision ozone sensor and deduce the true ozone value.

Calibration Example 2: A low-precision sulfur dioxide sensor is sensitive to changes in humidity and passing radio waves. The system combines the sulfur dioxide sensor with a humidity sensor, and a hydrogen sulfide sensor with similar sensitivity to confounding factors—while hydrogen sulfide (outside of sewers and marshes) is known to be low in the environment where the sensor system is deployed. The process calculates the sensitivity of the hydrogen sulfide sensor to sulfur dioxide and the sensitivity of the sulfur dioxide sensor to humidity changes. When the sulfur dioxide sensor reads high and hydrogen sulfide reads high, the system ignores the sulfur dioxide reading, assuming that a passing radio wave is setting off the system. When the sulfur dioxide sensor reads high and hydrogen sulfide sensor reads low, then a sulfur dioxide reading is confirmed.

Calibration Example 3: A network of air quality monitors is installed in a city. One of the air quality monitors is placed next to a reference monitor with high-precision gas sensors. Periodically (e.g., every minute), the error between the air quality monitor and the reference monitor is calculated and applied as a correction to other air quality monitors in the network.

Figure 5:
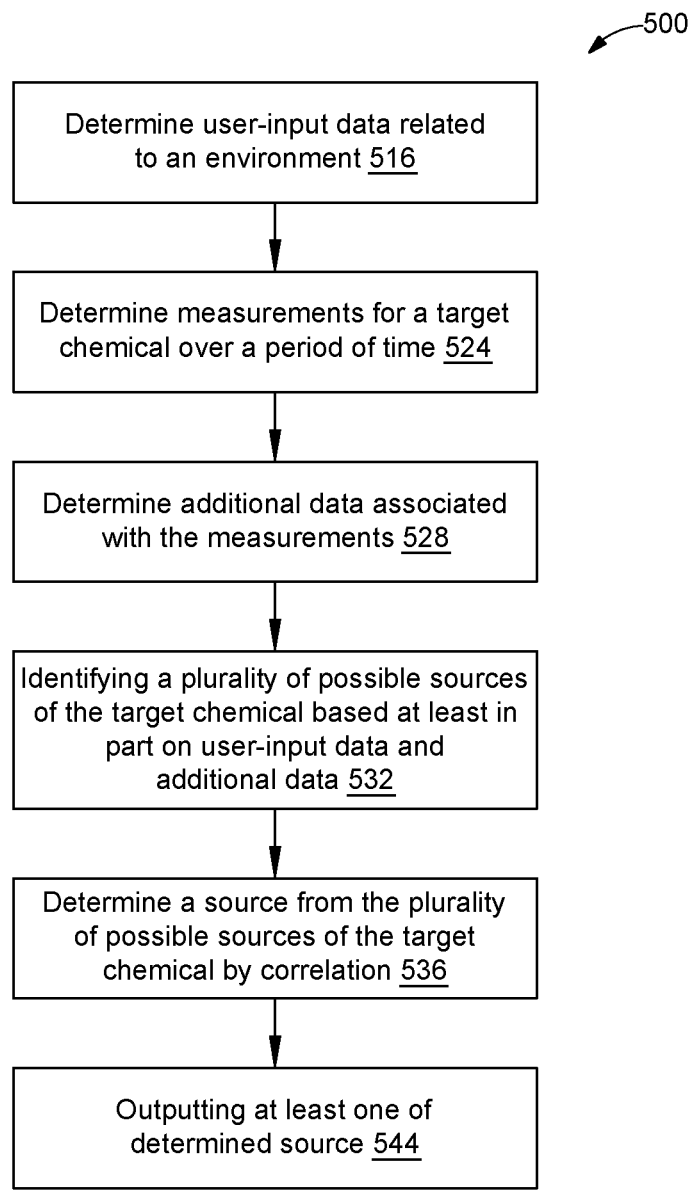
FIG. 5 illustrates a flow chart of an example source determination method, in accordance with an illustrative configuration of the present disclosure.

Source Determination and Action Recommendation Process: Air quality monitoring system 110 can be configured to determine sources of gas that are detected by air quality monitors. An example source determination method 500 is shown in FIG. 5. At step 516, user-input data related to an environment is determined. The user-input data may include any type of input about the environment, as such conditions associated with one or more air quality monitors deployed around a location. User-input data can include any of a variety of types of data such as:

1. type and location of objects, such as newly installed carpet that can out-gas chemicals;
2. events that can cause chemical emissions in the air, such as cleaning using chemical products;
3. layout of the location of concern, such as the placement of vents, windows, and doors; and
4. users' personal data, such as allergies, medical conditions, health concerns, daily routines, travel plans, and the like.

Air quality monitoring system (e.g., air quality monitoring system 110 of FIG. 1) may receive this data in any of a variety of way, such as through a website, an application installed on a mobile device, automatically from home sensors or mobile devices, information from other systems and services, and the like.

At step 524, the source determination method 500 determines measurements for a target gaseous chemical over a period. These measurements may be provided by air quality monitors of air quality monitoring system 110. At step 528, additional data associated with the measurements are determined. The additional data may include data from a variety of sources that are relevant to determining sources of gaseous chemicals measured by air quality monitoring system 110. The additional data may come from any of a variety of sources, such as weather data from weather stations, traffic data from traffic management administration, chemical emission events data such as from government reporting agencies, online services such as social networks, and the like.

At step 532, a plurality of possible sources of the target chemical are identified based at least in part on the user-input data and additional data. At step 536, one or more sources from the plurality of possible sources of the target chemical are identified by correlation. The correlation may be determined between the measured data from an air quality monitor, user-input data, and additional data. For example, the presence and amount of a gaseous chemical may correlate to an event or an object at the proximate location and at around the same time. The correlation process may be implemented in any of a variety of ways. An example process is shown below along with example equations that illustrate the methodology. Artificial intelligence algorithms and cloud-based data analytics may be employed as part of the correlation process.

At step 544, at least one determined source is output. The source may be output in many different ways, such as data to a service, a website, a user-interface on a mobile app, and the like. Source determination method 500 may also provide recommendations, such as to reduce the gaseous chemical from the source, reduce exposure to the gaseous chemical, and the like. Examples are provided in the source determination examples below.

Correlation Process and Calculations: An example of correlation steps and calculations are provided below:

1) Sort training data into categories using a clustering algorithm, such as a k-means clustering approach. Given a set of d parameters and n observations of each parameter, the present disclosure solved the following minimization equation to cluster the data into k sets S. This is done by finding means mu (μ):

$$\operatorname*{argmin}_{S} \sum_{i=1}^{k} \sum_{x \in S_i} \|x - \mu\|^2 = \operatorname*{argmin}_{S} \sum_{i=1}^{k} |S_i| \sigma^2 S_i \quad \text{Equation 3}$$

2) In real-time, feed in data. Using the categorization established in (1), determine which category $S_i$ variable x is most likely to fit by solving for i:

$$\min \sum_{i=1}^{k} \sum_{x \in S_i} \|x - \mu_i\|^2 \quad \text{Equation 4}$$

3) Map the categorization S to solutions S' using scientific literature reviews, best practices from experts, and clinical guidelines.

Source Determination and Action Recommendation Examples: The below examples illustrate some possible implementation scenarios of the chemical source differentiation process and example capabilities of the air quality monitoring system.

Source Determination and Action Recommendation Example 1: A volatile organic compound (VOC) sensor detects a large, quick increase in VOC concentration that quickly dissipates. By considering the concentration, change of concentration over time, and time of the signal, the process determines that the source is most likely to be a consumer cleaning product.

Source Determination and Action Recommendation Example 2: Detecting high VOC concentrations in an indoor environment, the air quality monitoring system recommends that individuals open a window to increase airflow and reduce their exposure.

Source Determination and Action Recommendation Example 3: The air quality monitoring system detects high temperature, pressure, and ozone levels outdoors characteristic of a stationary pressure weather system during the summertime on the East Coast. The system determines that the high ozone levels are most likely due to high levels of ozone being blown into the area, coupled with high levels of traffic. The system recommends that the city increase carpooling and public transportation use.

Source Determination and Action Recommendation Example 4: The air quality monitoring system detects moisture, pressure, and high levels of particulate matter during an early fall cold spell in the Pacific Northwest. It deduces that an inversion layer is responsible for the buildup in pollution and suggests that the city reduce biomass burning to reduce pollution (e.g., what is colloquially referred to as a 'burn ban').

Source Determination and Action Recommendation Example 5: The air quality monitoring system detects high levels of particles and nitrogen dioxide in India in the winter. The system recommends that users wear a protective mask to lower their health exposure to pollution.

Enhanced Gaseous Sensor with Paired Spectrophotometry and Nephelometry: The air quality monitoring system described herein may include an enhanced gaseous chemical sensor configured as a low-maintenance spectrophotometer and nephelometer that identifies gaseous chemicals by their light absorption spectrum and particulate matter by their scattering spectrum. The gaseous chemical sensor described below is a gaseous chemical sensing device for measuring chemicals in air. It includes a light source that emits light rays, and a spectrophotometric detector. The chemical sensor also includes a cell having two reflective surfaces located at opposite ends of the cell. The reflective surfaces are configured to reflect the light rays along a path across the cell and to direct the light rays to the spectrophotometric detector. This cell enables light rays to pass through the analyte gas multiple times to enable more accurate measurements and to minimize the interference of particulate matter in the analyte gas with respect to the spectral analysis. The configuration of the cell also enables the measurement of particulate matter in the analyte gas, for example, a sensor that measures light scattered by particulate matter that intercepts the light rays along the path.

Figure 6:
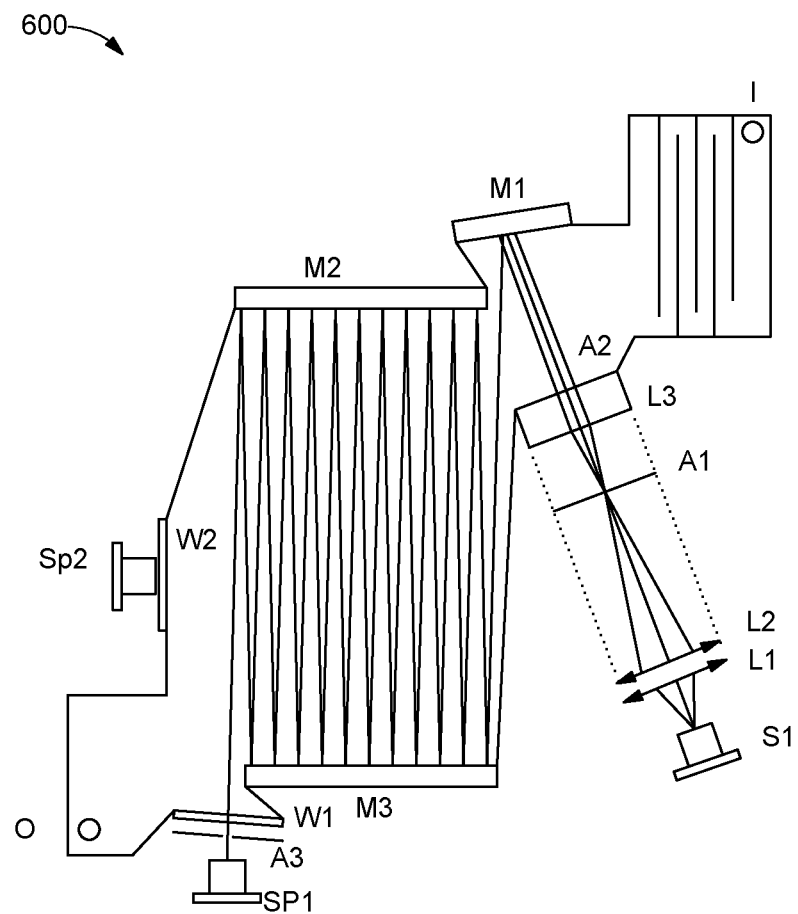
FIG. 6 illustrates an example of a gaseous chemical sensor with example components, in accordance with an illustrative configuration of the present disclosure.

The chemical sensor also includes an analyzer that measures at least one chemical by receiving measurements made by the spectrophotometric detector. It is configured to determine the amount of spectral absorption due to presence of at least one gaseous chemical and to compensate for the presence of particulate matter based on the amount of scattered light measured by the photodetector. An example such sensor that can be implemented in an air quality monitor and example components of the sensor are illustrated in FIG. 6 and described in more detail below. The example components illustrated in FIG. 6 include:

I: Gas intake followed by an inertial trap for large particulate matter
O: Gas outlet (where the analyte is pumped out)
S1: light source
A1, A2, A3: Round apertures to improve coherence
L1, L2, L3: lenses for the collimator/concentrator system; L3 serves as seal
M1: Alignment mirror to inject the collimated rays in the multi-pass mirror cell
M2, M3: pair of flat or concave mirrors forming a multi-pass mirror cell for path length extension.
W1, W2: Observation windows for the spectrometers
SP1, SP2: Spectrophotometer sensors; SP2 acts alternately as a nephelometer Optical Description: Light is produced by the light source S1 and collimated into (nearly) parallel rays by the optical system formed by L1, L2, L3, A1 and A2. The light source may have a reflector to improve light concentration. The chosen layout of lenses and apertures concentrate the collimated light into a tighter beam as well. Any other system of optical elements may be used to generate the light collimation and concentration, or other sources of collimated light such as a laser or laser comb may be employed.

The rays of light, concentrated and collimated, are injected in a multi-pass mirror cell by mirror M1. Such a cell may use flat or focusing mirrors M2, M3 such as convex mirrors (as with a Herriott cell, White cell, Pfund cell or circular multi-pass cell). The cell is configured to increase the pathlength of light passing through the analyte gas. The longer path length increases absorption and Signal-to-Noise Ratio (SNR). The rays of light, after exiting the cell, are directed toward the spectrophotometer sensor SP1. This sensor and accompanying digital circuitry determine the intensity and spectral distribution of light that travelled from the source and through the analyte gas. Sensor SP2 analyzes the spectrum and intensity of light rays scattered by any particulate matter present in the analyte gas traveling through the system from I to O. Micro-spectrophotometers, such as a Fabry-Perot Interferometer (FPI, such as those made by the manufacturer Infratec®) or diffraction grating-based micro-spectrophotometers (such as those made by manufacturer Hamamatsu) among others, may be suitable for SP1 and SP2. Alternatively, the light source S1 may be tuned to span the wavelengths of interest.

Structural Description: The body of the device separates the optics and electronics from the environment, exposes the optical cell to the pumped gas analyte, rigidly maintains alignment of the optical elements, and limits the influence of stray light rays on the light spectrum emitted by S1 and on the measurements obtained by SP1 and SP2. The body of the device may be built as a single structural unit with top and bottom plates for sealing. The body may be built out of various rigid materials, and can be 3d-printed, machined, molded, injected, extruded, or produced through other suitable processes. Interface elements are used to connect the optical elements to the body. The structure may also be optimized to limit the upper bound of particulate matter in the device body without placing filters on the input analyte gas channel.

For sealing, gaskets may be used between the mirror cell (exposed to the analyte gas), the environment, and the optics and electronics (maintained in a dry and neutral atmosphere). Certain optical elements, such as the observation windows W1 and W2 and the lens L3, serve as an interface between the optical chamber and the rest of the system, and may be used as seals.

For optics alignment, the structure is rigidly constructed and may use symmetries, topology optimization and low thermal expansion materials to limit misalignment of the optical elements during the lifetime of the device. Opto-mechanics systems may be used to ensure calibration and positioning of optical components. Interface elements in the form of adjustable mounting plates act as optical holders for precise alignment and calibration. These plates may be machined to fit the optical elements precisely and may be linked to the main body with screws, bolts, or other fastening systems. The plates are set in place in the body such that the described optical path is realized, and their positions can be calibrated at assembly and during periodic maintenance.

For stray light ray limitation, the entire body of the device in the optical cell may be coated with a light-absorbing coating with low reflectivity in the band of observational interest. This can be achieved in a variety of ways, such as by anodization, by deposition, or by painting a coating using carbon black, nigrosin, black oxides of various metals (such as aluminum, zinc, or platinum), graphene, graphite, carbon nanotubes or fluorenes, felt, or various other materials. The structure may further integrate optical baffles and reflection traps that can limit stray rays reaching SP1 or SP2.

For passive, filter-less avoidance of clogs, an inertial trap can be used by taking advantage of the conservation of linear or angular momentum. Vortex-like traps can be used to force larger particulates out for high-speed pumping rate, and meander-like traps (such as the physical element proximal to I in the schematic) can be used with a low-speed pumping rate. These structures can be added to serve as passive filters of large particulate matter in order to extend operations of the device between routine maintenance servicing. Disposable filters may also be used.

Functional Description of Gas Identification: The analyte gas may be pumped into the spectrometer through I and may exit the device through O. Pumping can be performed with any type of fan or pump. The pump may be located on the output line to provide laminar flow and pumps the gas out from O.

The analyte gas contains trace gases to be identified by the spectrometer. While passing in the spectrometer, the analyte gas intercepts rays of light and absorbs specific wavelengths, which depend upon the type and concentration of gases in the sample. Further, the analyte gas may contain a heterogeneous suspension of particulate matter which intercepts, absorbs, and scatters light. The scattering depends upon the size distribution of the individual particles in the particulate matter suspension and the absorbance depends upon the albedo and geometry of those various individual particles. By observing the spectrum of the transmitted light and the spectrum of the scattered light, information relevant to the gas type and scattering profile of the particulate matter can be inferred.

Signal Processing: The raw information gathered by the proposed system is in the form of light intensity, with respect to wavelength and time, as gathered from the spectrometers SP1 and SP2. These signals, called spectra, depend on the properties of the analyte gas and particulate matter, the light source, the optical system, and the spectrometer sensor properties. By using the known properties of the light source and the optical system, the signal is first processed. The optical properties of the specific spectrometer sensors employed are also used to further refine the signal. For the case of Fabry-Perot Interferometer (FPI) sensors, the information about the FPI transfer function is used to apply a signal deconvolution (or convolution of the reference solution) and enhance the sensor sensitivity when compared to the manufacturer-reported resolution.

For trace gas detection, the spectrum values from sensor SP2 is used to further enhance the spectrum data obtained by sensor SP1. Some of the spectrum of SP1 that may be attributed to absorption may in fact be the result of scattering, and the scattered light spectrum obtained by SP2 can be used to assist interpretation of the signal from SP1. Ad hoc knowledge about the probable analyte content using the data analytics methods described herein, together with the known typical spectral signatures for various gases at ambient environmental concentrations may be used to assist with interpretation of the spectrometric data into probable gas mixtures and concentrations.

For particulate matter detection, the spectrum values from SP2 are used to identify characteristics of the particulate, such as material, size, or albedo, depending on what is known or may reasonably be inferred about a particular particulate matter suspension. The particulate matter scattering spectrum can be used as a fingerprint for a particular type of particulate. The alignment of sensor SP2 in the optical system is standard for a light-scattering detector known as a nephelometer. However, nephelometers generally do not use broad-spectrum analysis and rely on aggregate particle scattering behavior in a single light wavelength to analyze scattered light. By using a broadband spectrum for light source S1, more information could be gained on the size, material, or albedo of the particulate matter. Acquiring a library of spectral responses for various particulate mixtures could be used to help identify probable mixtures of gases and particulate matter at ambient environmental concentrations in the sample, particularly when paired with environmental information regarding a given sampling location.

Example of Signal Processing for Methane Monitoring: The analyte gas mixture contains an inert gas, water vapor, carbon dioxide and methane as well as particulate matter. The spectra from SP1 and SP2 are collected, as well as the temperature and pressure of the chamber. The signals SP1 and SP2 are first deconvolved from the known transfer function of the optical system and the light source at the known temperature and pressure of the chamber. The transmission spectrum from SP1 is compensated by the scattered spectrum of SP2. Similarly, the transmission spectrum from SP1 is used to improve the scattered spectrum of SP2. The individual reference spectra at known concentrations of water vapor, carbon dioxide and methane may be recovered from investigations or from a public database. The known transfer function of SP1 is applied as a convolution to the reference spectra of water vapor, carbon dioxide and methane. One illustrative algorithm generates synthetic spectra of the water vapor, carbon dioxide and methane mixture from the convoluted reference spectra for various concentrations at the measured temperature and pressure. By minimizing the difference of the generated synthetic spectra and the actual refined spectrum from SP1, best estimates of the actual concentrations of water, carbon dioxide and methane are found.

Figure 7A:
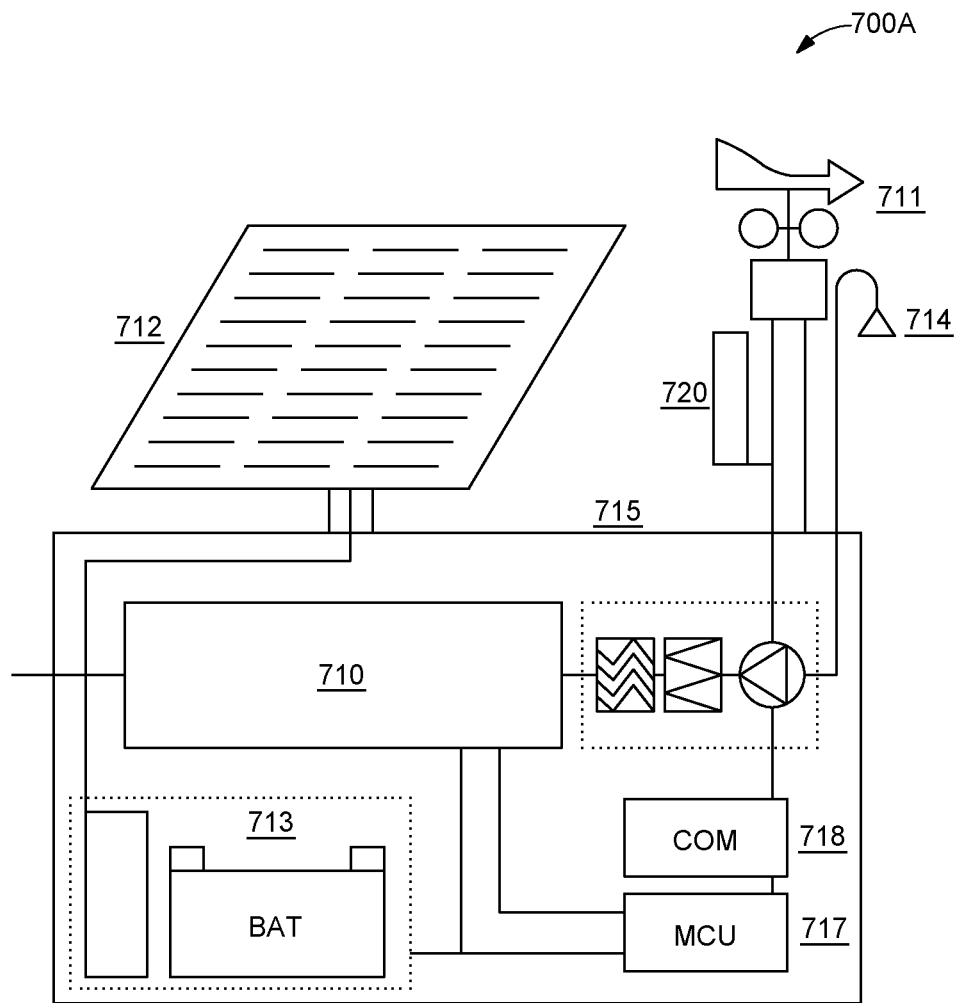
FIG. 7A illustrates an embodiment of the sensor system, which is deployed in the field, in accordance with an illustrative configuration of the present disclosure.

FIG. 7A presents a particular embodiment of a sensor system 700 capable of measuring a target compound and one or more environmental parameters (e.g., weather conditions) in a collocated and contemporaneous manner. The compound measurement function of the sensory system of FIG. 7A is performed by the compound sensor or sensors 710. These sensor(s) are point sensors, which means that their function is to measure a particular physico-chemical property of the target compounds to distinguish them from background atmospheric composition (targeted compounds include, but are not limited to: one or more gases and aerosols that are emitted by one or more industrial, anthropogenic, or natural activities). In particular, one embodiment focuses on hydrocarbons and other greenhouse gases that absorb in the mid-IR region of the electromagnetic (EM) spectrum, in particular wavelengths between 1 um and 5 um. In one embodiment, compound sensor 710 is an absorption spectrophotometer that can measure mid-infrared absorption in the 3 um to Sum range of the EM spectrum. Without loss of generality, compound sensor 710 may comprise other sensor technologies that may be similarly used for the measurement of target compounds.

In order to capture a sample for analysis, a sampling cane 714 may be used to pump an air sample at a specific height and avoid sampling water in the case of precipitation or other foreign agents of large size. The sample may be pumped and conditioned by a sample pumping and conditioning system 719. The system depicted 719 may include a pump for sampling the air for the compound sensor 710, a filter for the removal of particulate matter and a coalescent filter for the removal of water. The system may further include desiccant filters, temperature and pressure adjustment systems, valves, and additional drain pumps to facilitate moisture removal, temperature conditioning of the sample, or for flushing and other filter regeneration tasks. The purpose of this is to provide a properly conditioned sample based on the sensor system requirements, while limiting the necessary maintenance of the pumping and conditioning system 719.

In some embodiments, the compound sensor 710 may use an open path in order to avoid the necessity of pumping or conditioning samples. The sample may then be naturally transported into the sensing area by weather patterns without the use of a cane 714 or sampling pumping and conditioning system 719.

The sensor system of FIG. 7A further includes a weather sensor system 711 collocated with the sampling point of the compound sensor 710 around the sampling cane 714. The weather sensor system should at least include sensing elements to measure wind speed and direction. Further sensing about temperature, pressure, hygrometry, insolation, and precipitation may also be used to refine the subsequent modeling effort. The wind speed and direction may be measured by a combination of a wind vane and an anemometer, or by an anemometer alone such as in the case of using an ultrasonic anemometer. The wind direction measurement may be made in two or three dimensions. Temperature may be measured using MEMS sensors, thermistors, or other suitable sensing technology. Pressure may be measured using a barometer sensor and hygrometry by a moisture sensor. The sensors for temperature, pressure and moisture may be connected for improvement of each of the measures as they are interdependent. Insolation may be measured using a photodiode or any other appropriate light-sensitive sensor. Precipitation may be measured using a precipitation sensor with auto-draining capability. While collocating the weather measurement with the sampling point is important for the purpose of accurately characterizing emissions, it is not absolutely necessary for performing the method as long as weather measurements are collected in close proximity to the sensor system (e.g., within 100 m). This conformation, i.e., being collocated, minimizes the measurement error and is the one illustrative configuration of the present disclosure.

The data collected by the compound sensor 710 and weather sensor system 711 may be collected and processed by a local computing unit 717. The local computing unit may also control the execution of the main sampling and measurement program and the actuation and controlling of any subsystem of the sensor system 700. The local computing unit 717 runs the main firmware, which schedules and collects data from compound sensor 710 and weather sensor system 711, conditions the sensor signals into a rational format, performs data preprocessing, locally stores data, formats, and prepares messages, and generates diagnostic and metadata pertaining to the identification, time stamping and operational diagnostics of the sensor system and supporting circuitry. The messages may be encrypted and transferred to a communication unit 718 and messages may be received from remote assets. The communication unit 718 includes a modem or other interface that conditions the message to the right protocol for communication or receives external messages to be communicated to the computing unit 717. The communication protocol may be wired, such as a SCADA system or wireless, such as Bluetooth®, Wi-Fi, LoRa, cellular or satellite or any other radiofrequency, optical line of sight, or other wireless data-transmission protocol. If a wireless protocol is employed, the data may be relayed using a communication antenna 720, if appropriate. In general, a communication system, which may consist of a communication antenna 720 and communication unit 718, has a role that includes the communication of the measurement to a remote or centralized node and the receipt of communications related to settings and operations changes or firmware updates. The communication system may be used to relay messages to and from other sensor systems such as in a daisy chain, star, or mesh configuration in order to reduce the communication cost when relying on external communication infrastructure such as cellular or satellite communication networks. In case of communication error, or other cases that warrant it, the messages may be stored by the computing unit 717 to communicate at a later more opportune time. For example, when communication services may be interrupted, multiple channels of communication (such as multiple wireless data-transmission protocols) may be used to attempt to alert the computing unit 717 to changes of operating conditions and to receive instructions.

The deployment of sensors in the field may require the exposure of the equipment to harsh outdoor conditions with no external support such as power access and communication infrastructure. The sensing system is housed in an enclosure 715 to protect the system from the environment and from tampering. This may include, but is not limited to: precipitation, moisture, surface water and flooding, high temperature and insolation, low temperatures, high winds, storms, hurricanes, typhoons, tornadoes, lightning, external impacts and vibrations, robbery, defacement, damage, earthquakes, light or electromagnetic interference, foreign agents or fauna and flora disturbance or intrusion. The enclosure 715 may also be highly visible by day and reflective at night to avoid accidental damage. The enclosure 715 may be directly on the ground, mounted on a foundation, or pole-mounted.

The sensor system in FIG. 7A may produce and manage its own power. In one embodiment, the sensor system may include a solar power system 712 and a power conversion and storage system 713. The solar power system 712 and power conversion and storage system 713 are designed to provide sufficient power to the various other subsystems with sufficient reserves and capacity to ensure proper functioning of the sensor system in most environmental conditions present in the field. Solar power system 712 may be replaced by wind- or gas-based power generation, or any other form of compact power generation system if the conditions warrant it. For instance, at high latitudes wind-based power generation may be preferable to solar on account of low insolation. The power conversion and storage system 713 may include a battery storage bank and a charge controller. The power conversion and storage system 713 may further include power converters for providing appropriate power to the various systems, relays, fuses, and breakers, and switches appropriate for the power protection, function, and physical interfacing required by a particular embodiment of the sensor system. The battery storage bank may include lithium-ion (such as LiFePO4 cells), lead acid (such as a deep-cycle sealed battery) or any other appropriate battery technology that can operate nominally in conditions that may include high and low temperatures and irregular charging profiles. The charge controller may use Pulse-Width Modulation (PWM) or Maximum Power Point Tracking (MPPT) or other technology appropriate to convert the raw energy from the solar power system 712 to the battery storage bank charging requirements. All subsystems of FIG. 7A may be modular in nature to facilitate replacement of subsystems with minimal tools in the case of maintenance.

Figure 7B:
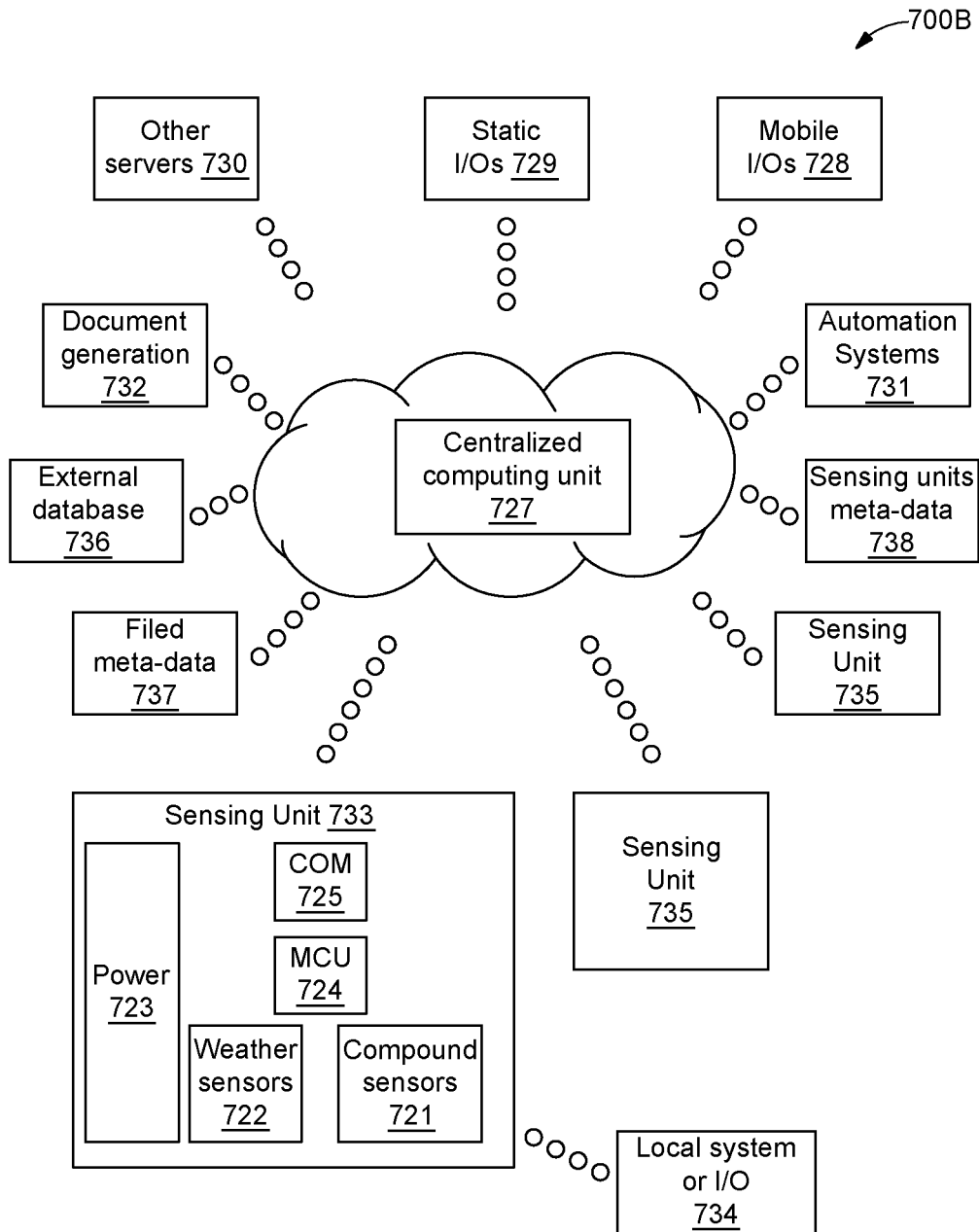
FIG. 7B illustrates an embodiment of a communication architecture of a set of sensor systems, in accordance with an illustrative configuration of the present disclosure.
Figure 7C:
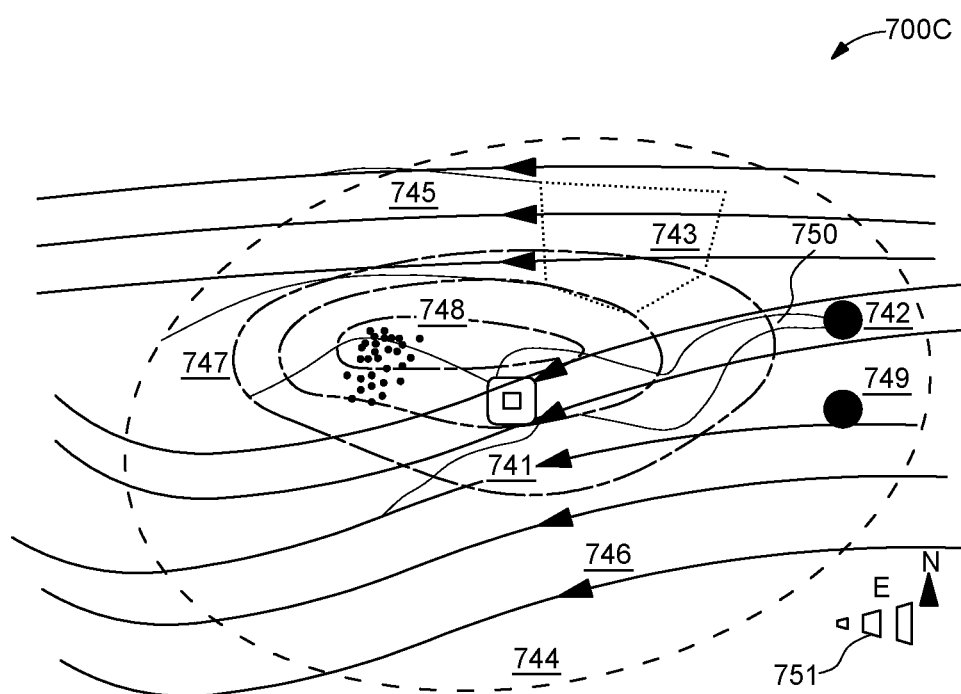
FIG. 7C illustrates a symbolic map representation of a sensor deployment amid the field where sources are present, in accordance with an illustrative configuration of the present disclosure.
Figure 7D:
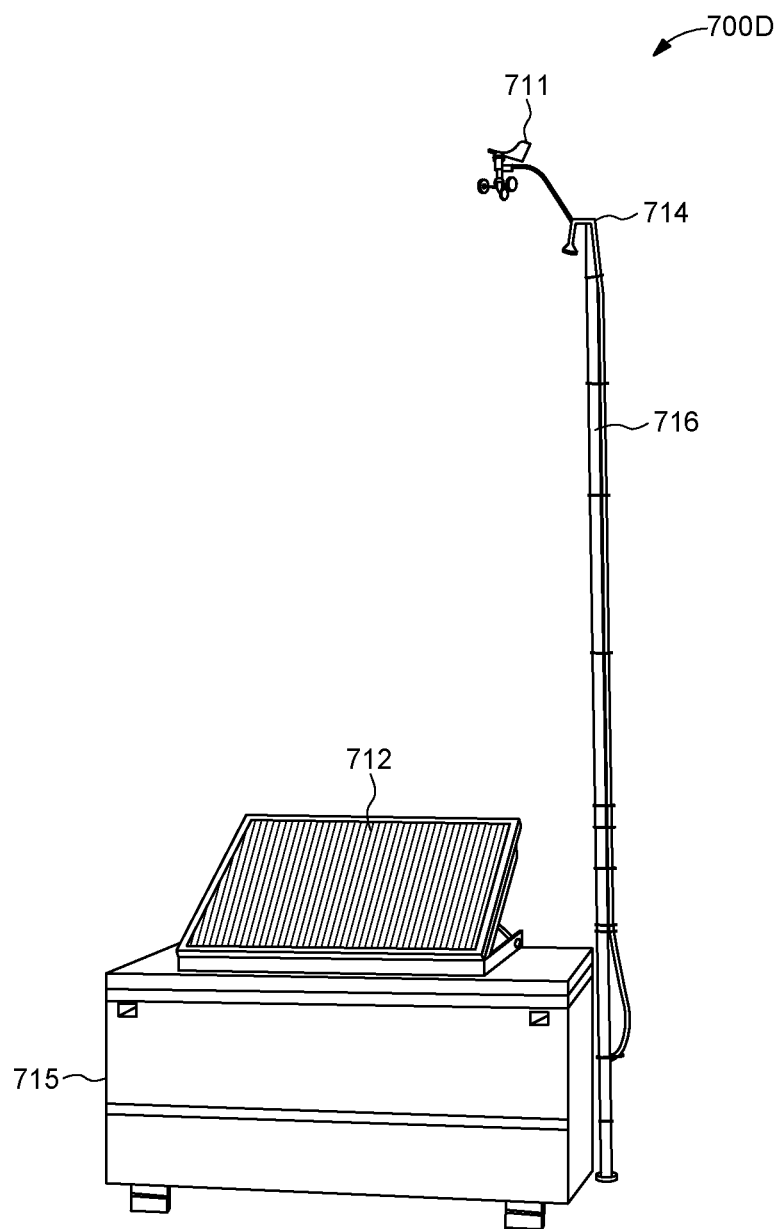
FIG. 7D illustrates another view of the embodiment of the sensor system of FIG. 7A, in accordance with an illustrative configuration of the present disclosure.

FIG. 7D shows another view 700D of the embodiment of the sensor system of FIG. 7A. The system includes enclosure 715, anemometer 711, pole 716, sampling cane 714, and solar power system 712.

Figure 8A:
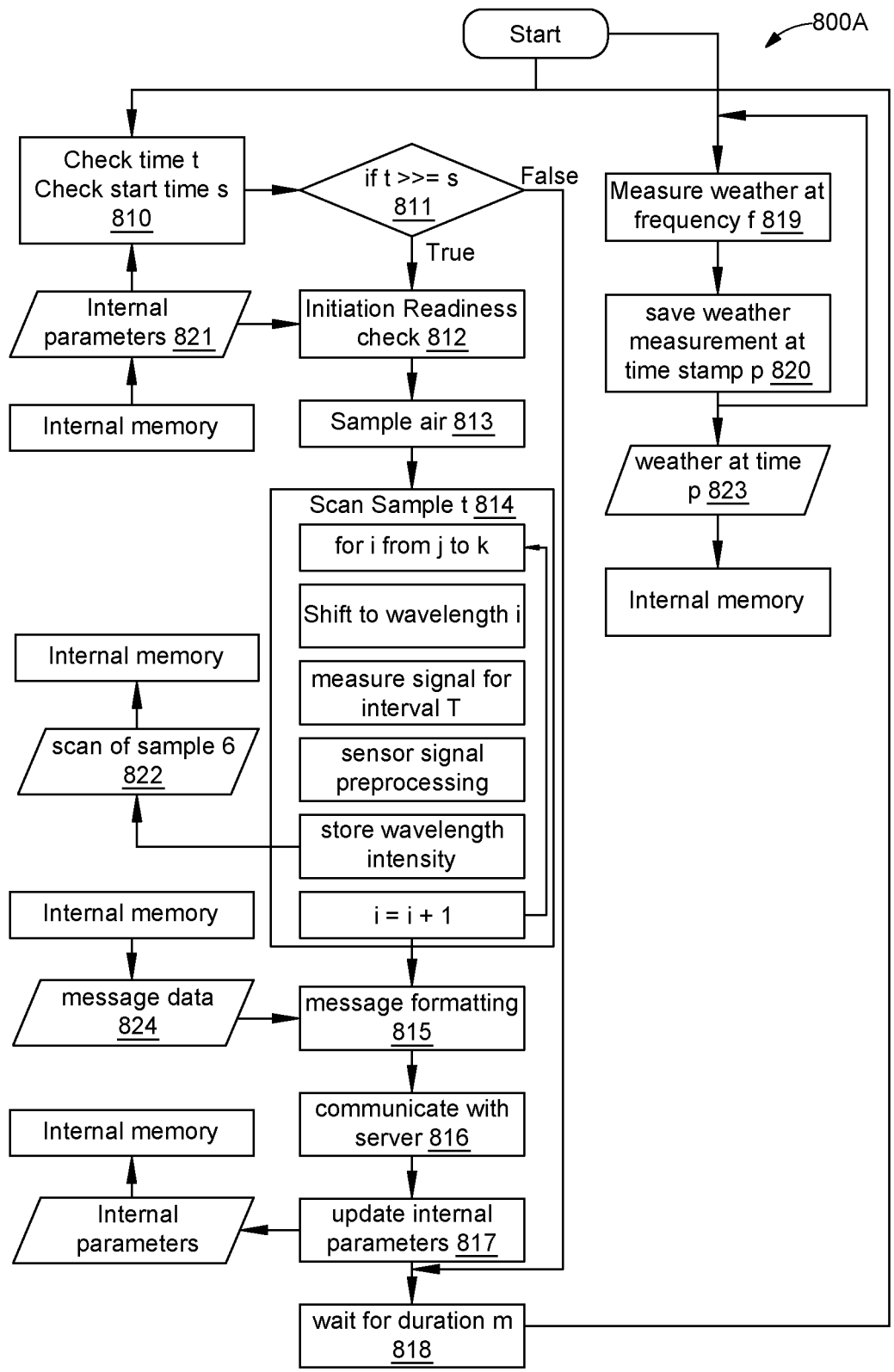
FIG. 8A illustrates an embodiment of a method for compound measurement related to spectroscopy, in accordance with an illustrative configuration of the present disclosure.

With regard to the sensor system disclosed in FIGS. 7A and 7D, certain critical functions may be performed for the collection of sensor data and for relaying sensor data through the communication units. The flowchart 800A displayed in FIG. 8A presents an embodiment of a method for collecting weather data as well as compound measurement data. In particular, a compound sensor is capable of scanning the absorption spectrum of a sample as presented in 814. Step 814 may be generalized to any other compound sensor system embodiments that are sensitive to certain physical or chemical aspects of said compound(s) such that concentration of such compound(s) in the sample can be derived from the measurements of such physical or chemical aspects with a sufficient actionable detection limit for the end user's intended application. FIG. 8A presents an example of a method using a particular embodiment of the sensor. Other embodiments which collect and communicate compound and weather measurement may be also used. For example, the sensor system in FIGS. 7A and 7D may have other operational functions that can facilitate the sensor system operation and the functions described in FIG. 8A.

The sensor system performs measurement of the weather concurrently to the measurement of the compounds of interest. The weather measurement step 819 by the sensors, such as those described in reference to FIG. 7A, is performed continuously at a frequency f. In step 820, each weather measurement is time-stamped at time p and saved. In step 823, the weather measurement at time p is stored in the internal memory. The frequency f may be read from an internal parameters table 821 and may be dynamically allocated. The measurement at time p in step 823 may also be obtained as a combination of multiple measurements obtained during step 819. For example, wind direction may be measured every second but stored over 1 minute averages.

The sensor system of FIG. 8A as described above operates on a dynamic schedule for the sampling of air. In step 810 of FIG. 8A, the time stamp t as kept and measured by the device and the scheduled start time s as read in from the internal parameters table 821 as stored in the internal memory may be checked. The device compares times t and s in step 811 to determine if it is time for starting the sample sequence. If too early (false; t<s), the device waits for the duration m in step 818 and restarts the loop from step 810. The duration m may be selected as the time difference between t and s minus the process time to loop from step 818 to step 811. If step 811 instead finds that it is time to sample (true; t>=s), the function proceeds forward to step 812.

In step 812, initiation and readiness checks are performed. This may involve diagnostic functions for all the subsystems, the communication unit pinging the server, and readying of the compound sensor such as reaching a target temperature or any other necessary state for operations. Step 812 may trigger the operation of a subsystem dedicated to enforcing nominal conditions. For example, the temperature of the sensor may be found out of bounds for optimal operation and a thermal regulation subsystem may be triggered to raise or lower the sensor temperature. Step 812 may result in delaying the sensor measurement, aborting the sensor measurement in the case where critical issues are found that inhibit measurement, delaying or aborting communication of the message if communication can't be performed, or fully aborting the performance of the sampling sequence. For example, a battery voltage may be found to be under a critical voltage that would reduce the sensor system's life expectancy between maintenance cycles, and the sample sequence may be aborted to avoid damaging the battery. Another example may be that the server link may not be possible at this time and the measurement may be stored for subsequent communication. The diagnostic result may be stored in step 812 for the purpose of communication to the server and for storage in the internal logs for subsequent maintenance check. When all the diagnostic functions are performed in step 812 and if all the diagnostics point toward a nominal state, the firmware may progress to step 813.

In step 813, a sample acquisition mechanism may be triggered. In the case of a short open path, the sample collection may be achieved naturally by the force of the wind without any actuator. Other systems may trigger a pumping mechanism that transfers the air sample to a sampling chamber. The step 813 may further involve the trigger of active subsystems for the conditioning of the sample, such as pneumatic systems for the removal of water or particulate matter or other undesirable contaminants. For example, a subsystem may involve, prior to sampling, a regeneration mechanism for adsorption or absorption-based desiccation. The conditioning of the air sample in step 813 may be fully passive, for example, when the pumping pressure differential is used for actuation in the case of an auto-draining coalescing filter.

When the sample of air is in a sample cell where the compound- or compounds-sensitive sensor operates, the measurement may be performed in step 814. The specific sensor technology embodiment presented in step 814 of FIG. 8A may operate, for example, by scanning absorption spectroscopy. In this case, the sensor measurement is operated by observing sequentially a set of target wavelengths from j to k. For a specific wavelength i, the sensor or source proceeds to shift in order to observe the spectrum centered on wavelength i. The sensor's analog signal is then measured for a time interval T and converted into a digital signal at a certain sampling rate. The digital signal is then preprocessed to identify the sensor's response intensity associated with the measurement centered at wavelength i. This wavelength intensity is stored as part of the scan 822 of the sample measured at time stamp t, which is completed when all the intensities associated with wavelengths j to k are measured.

When the sample scan is performed in step 814, the sensor system proceeds to message preparation and formatting in step 815. The message formatting involves message data 824 gathered from the internal memory. This may involve the current sample t measurement. This may include a set of weather measurements at time p measured before and during sampling. Diagnostic information as well as sensor metadata identifying the sensor and its subsystem, operation, and such may also be added to the message. Furthermore, previously captured, and stored sample and wind measurements may be added to the message data, for example when communication was unsuccessful at the previous sampling schedule time. Finally, relayed messages from other sensor systems deployed in the field may be added to the message data 824, for example when the sensor systems are networked to reduce the cost of communication to the central computing unit. The formatting in step 815 may involve encryption of the message. The message in step 815 may be further formatted into packets suitable for transmission by the communication unit.

In step 816, the message is transmitted to the server in suitable packets. Packet integrity may be evaluated to ensure that any data transfer or communication failure may trigger retrying transmission or the storage of the message for subsequent transmission. The sensor system may further query for an update of internal or operational parameters in step 817. This step may involve a general firmware update that would alter the operation of the device to a new modality or may simply influence critical parameters, such as the schedule for sample measurements, weather measurement frequency and storage or other parameters that pertain to the operation of the critical and non-critical functions. In some embodiments, step 817 may be triggered by dynamically analyzing the latest measurements. For example, the schedule of subsequent measurements may be shifted as a response to changes in recent past measurements. For instance, if a large concentration of a target compound is detected, the frequency of measurements may be augmented to increase the response speed in case of a critical emission. In another instance, wind measurement may trigger an immediate sample sequence in order to capture an emission from a critical direction. The critical direction may be, for example, the direction from which a source emission is likely to be observed. This dynamic scheduling may be decided by a sensor system control unit using edge computing resources, or by query from the centralized computing unit 727 of FIG. 7B for scheduling decisions requiring human intervention or larger computing resources. The sensor system firmware may loop in step 817 for dynamic scheduling until the time for the next scheduled sample approaches. The device may then proceed to step 818 until time s is near and repeat the main sample loop starting at step 810.

In some configurations, a cloud server (for example, "Amazon Wes Services" or simply "AWS") may be provided. Further, each of the sensor systems (i.e., the plurality of air quality monitors) may include control unit which may be using edge computing resources. The edge computing resources may further include a processor (for example, processing module 211), and an averaging routine operatively associated with the processor. The processor may be configured to average a series of the actual emissions measurements obtained by the each of the plurality of air quality monitors to generate an averaged actual emissions measurement. The averaged actual emissions measurement may be generated by the processor at each of the plurality of air quality monitors, according to the averaging routine. The processor may be further configured to transmit the averaged actual emissions measurement to the cloud server. It may be noted that the each of the plurality of air quality monitors may be communicatively coupled to the cloud server. As such, the data received from all the plurality of air quality monitors may be received and analyzed at the cloud server.

In some configurations, the averaging to generate the averaged actual emissions measurement may be dependent on either the wind speed or the wind direction. Further, the averaging to generate the averaged actual emissions measurement may be increased when the wind speed decreases below a diffusion-only speed. The diffusion-only speed may refer to the wind speed when the speed of wind is insufficient to cause considerable movement of emission gases along with the wind. As such, the emission gases only tend to diffuse in the surrounding air (i.e., move from region of high concentration to lower concentration). Additionally, or alternately, the averaging to generate the averaged actual emissions measurement may be increased when the wind direction indicates delivery of dry air (i.e., the air when the concentration of target compound/emission on the air is minimal or absent) to a predominate air quality monitor 3804(1) of the plurality of air quality monitors. As will be appreciated, increasing the averaging allows for more accurate detection of emissions, if any, in the above situations.

Further, in some embodiments, the edge computing resource of the air quality monitor may include a memory (for example, memory 213). The air quality monitor may further include emissions sensors (for example, chemical sensors 221-223) configured to obtain sensor data at a predefined frequency. The memory may be configured to store sensor data obtained by the emissions sensors. The air quality monitor may transmit the sensor data to a cloud-base database (for example, "AWS"). Further, the edge computing resources (or processing module 211) may detect a low-connectivity condition. The low connectivity condition may be as a result of network downtime/failure, power failure, etc. Upon detecting the low-connectivity condition, the air quality monitor may start storing the sensor data in the memory. Further, upon detecting a normal-connectivity condition, the air quality monitor may start transmitting the sensor data stored in the memory to the cloud-based database.

Further, the air quality monitor may detect a threshold condition. The threshold condition may be one of a large concentration of a target compound, or a wind measurement from a threshold direction. It may be noted that the threshold direction may be a direction from which a source of emission is likely to be observed. In such a threshold condition, the air quality monitor may augment the frequency of obtaining sensor data by the emissions sensor, based on the detection of the threshold condition. The processor (e.g., processing module 211) may further procure the sensor data from the emissions sensor, and average the sensor data to obtain averaged data. The averaged data may be obtained according to one of a time-based criterion, or an event-based criteria. For example, the time-based criteria may define a time period (e.g., 60 seconds) after which the averaging of the sensors data obtained during that period may be performed. The event-based criteria may define an event (e.g., a low wind condition or high wind condition based on a windspeed threshold) on occurrence of which the averaging may be performed. The air quality monitor may further include a transmitter communicatively coupled to the processor. The transmitter may transmit the averaged data to the cloud-based database. In some embodiments, the air quality monitor (i.e., the processor) may sequentially combine the averaged of the sensor data into a data packet, and transmit the averaged data to the cloud-based database via a receiver. The receiver may be one of a cellular networks, a wired network, a satellite, a shortwave radio, a CDMA network, or a GSM networks.

The embodiment of the system as in FIGS. 7A and 7D or any other sensor system embodiment capable of measuring target gas and weather measurements in a collocated manner may be deployed in a field where prospective emission sources are present. A symbolic map 700C of a prospective field deployment is presented in FIG. 7C. In FIG. 7C, a sensor system 741, as depicted by a rounded-corner square, is deployed in the field to detect emissions plumes 745, 750 of target compounds, depicted by color gradients. These emissions plumes 745, 750 may be emitted by point sources 742, 749 depicted by circles, or by area source 743 depicted by a filled polygon. The plumes 745, 750 are transported by advection by an air flow as denoted by streamline arrows 746, and by buoyancy and diffusion of the compound in air. Typically, the air flow is of a complex three-dimensional geometry and depends on many parameters including, but not limited to, terrain, surface roughness and obstacles, temperature and pressure differential, insolation and inversion layer position, turbulence, and atmospheric boundary conditions or other atmospheric conditions forced by large-scale weather patterns. The streamlines 746 are a simplified view of the average transport (where turbulence is approached as an average) of air parcels during the sampling time. Note that the streamlines 746 are influenced by the effect of a terrain 747, as noted by isoclines, and by the presence of obstacles 748 (e.g., trees) represented by the small black dots. In this specific snapshot, the point source 742 is emitting the target gas, thereby producing plume 750 which is transported by the air flow 746 to the sensor system 741. Note that the cross section of the plume 750 increases when further from the source 742 due to diffusion and turbulent mixing. Plume 750 can also appear to have a tortuosity due to the dynamic change in wind speed and direction during the transport. In this example, point source 749 is not emitting and area source 743 is emitting but its plume 745 does not intersect the position of the sensor system 741 in this particular snapshot. Note that plumes are typically three dimensional and may vary in vertical cross sections, though this is not displayed in this figure.

It may therefore be necessary to have precise wind measurement collocated at the sensor system as well as a modeling of the emission transport that considers terrain, obstacles, rugosity, and other field parameters that can affect transport. For instance, in the specific snapshot presented in FIG. 7C, local wind pattern 751 at long distance comes approximately from the East direction before entering the field of interest. The wind measurement collocated at sensor system 741 is approximately Northeast as denoted with streamline 746 intersecting sensor system 741. From the perspective of sensor system 741, diffusing area source 743 is located in the northeast sector, point source 742 is located in the east-northeast sector, and point source 749 is in the east sector. Only plume 750 from point source 742 is measured by sensor 741 in this particular snapshot.

If a model only accounted for a wind direction and/or speed from a local weather pattern, such as that for a distant wind measurement of local wind pattern 751, the perceived source for plume 750 detected by sensor system 741 would be in the East sector, thereby leading to the incorrect guess that point source 749 is the source that is emitting plume 750. However, if the collocated measurement of wind direction at sensor system 741 is considered, plume 750 appears to be coming from area source 743, which is also incorrect. Note that a simple, linear local back-tracing of the wind parcel from the perspective of the wind sensor in sensor system 741 would have led to the same bad conclusion that area source 743 is the source since the terrain is the main source of the non-linear wind flux geometry. What this example shows is that identification of sources from wind speed and direction measurements alone is difficult without large numbers of wind measurements.

In one embodiment, fine measurements of wind around the site would be taken to properly measure the complex wind pattern responsible for the plume transport. Using multiple wind measurements can be cost-prohibitive. In another embodiment, a simulation of the emission transport using a digital twin of the site is performed. Such a digital twin can reconstruct an estimation of the actual flux responsible for the transport and consider the effect of terrain 747, obstacles 748, source geometry 743, 742, 749, as well as other parameters relevant for the turbulent advection/diffusion of the target emitted compounds. With that simulation, the accuracy of the flux in the site is enhanced and closer to the actual flux of air flow 746. Because of this, attributing the plume 750 to point source 742 with a single deployed point sensor is possible.

The same model may allow for reconstructing a detection limit 744 of the sensor system 741. Detection limit 744 denotes the limit for which the smallest leak size is only detected 50% of the time. Other criteria for detection limit 744 may be specified for different leak size or different confidences of detection. In a perfectly flat model with a uniform chance of wind in any direction, the detection limit at a constant altitude is circular (approximated by a cardioid in three dimensions). In practical cases, the shape of the detection limit may be very complex and may change based on wind pattern, temperature and pressure, terrain and other parameters impacting the transport of the compounds as well as detection limits of the sensor itself. FIG. 7C gives an approximation of the detection limit at constant altitude as an ellipse. In this case, sensor system 741 is adequately positioned to detect emissions from sources 743, 742, and 749 as these potential sources are within a range of the detection limit 744 of the sensor system 741. Note that other positions may lead to higher sensitivity to sources 743, 742, and 749 but the position of sensor system 741 may be dependent on other factors, such as land usage authorization, better line of sight for communications, or network optimization positioning for a deployment with more than one sensor system.

Multiple sensor systems as described in FIGS. 7A, 7C, and 7D may be deployed in a field for the acquisition of weather measurement and compound measurements. The sensor system takes these measurements and relays messages related to these measurements with timestamps, identifiers, and other metadata regarding sensor operations to a centralized computing unit 727 in FIG. 7B. The communication of data and commands is represented in FIG. 7B. Sensing unit 733, which may or may not be the same as that described in FIG. 7A, can incorporate components such as a power system 723, weather sensors 722, compound sensors 721, a computing unit 724, and a communication unit 725. Sensing unit 733 can relay messages, as described above, to centralized computing unit 727 using network layer. The network layer may rely on existing communication infrastructure such as cellular or satellite, or dedicated infrastructure such as custom wired or wireless systems, including but not limited to, Wi-Fi, Bluetooth, SCADA systems, LoRa, and other telemetry and data transmission systems. The data transmission may rely on other network infrastructure, such as the Internet or on dedicated networks such as intranet or LAN. Sensing unit 733 may also directly transmit messages to non-networked systems or local systems 734 as may be the case for a local interface used by the sensor system user. The message from sensing unit 733 may be relayed through other sensor units as in daisy-chained or starred sensor system networks or through a dedicated unit for the local storage, scheduling and packaging of messages from various sensing systems 733, 735, deployed in the vicinity of each other. This may be done to amortize the cost of expensive transmission technology such as satellite links.

Once in centralized computing unit 727, message processing is performed to transform raw data into actionable data. This may include simple operations such as data formatting or more complex operations such as creating a maintenance tracking system for the operator. In one embodiment, the data processing is the conversion of weather and compound measurements into detection, localization, quantification, and qualification of target compound emissions. To transform the raw compound measurement into speciation and concentrations, an external database 736 such as the HiTRAN database may be queried for reference spectra, or internal databases of calibration measurements taken with the specific sensing unit 733 during calibration runs. Other information such as sensor units' metadata 738 may be used for the specific instrument characteristics to enhance speciation and concentration measurements.

In order to perform localization, quantification and qualification, centralized computing unit 727 may reference field metadata 737 collected by field operators such as, but not limited to, topological maps of the field deployment, images of site, the potential sources and equipment, equipment inventory and GPS coordinates of features of interest, for the purpose of creating a digital twin of the site for the purpose of atmospheric transport modeling and simulation. Other field metadata may include previous local weather information and the external weather databases 736 are queried.

Centralized computing unit 727 may use other messages from another sensing unit 735 for enhanced localization, quantification, and qualification of the emissions. Sensing unit 735 may include multiple sensing units and may be of the same type as sensing unit 733 or any other sensing units present on the sites. For example, sensing unit 735 may be a flare lighting sensor used as an indicator to help attribute an emission detected by sensing unit 733 to a flare misfiring.

Actuator commands may be used as a sensor feed as well. For example, the actuation of pneumatic equipment at oil sites may result in a predictable emission; therefore, command signals from actuators may be used to help predict expected emissions from an oil site. An example in the landfill industry may be variation in the pressure head of wells which may be correlated with a local emission hotspot. This concept can be extended to all existing command signals and process sensors already present in equipment associated with potential emissions sources.

Once detection, quantification, qualification, and localization of sources is obtained by the processes in the centralized computing unit 727, actionable data may be generated. Actionable data may mean the data necessary to take a corrective action, including, but not limited to, emission reports, maintenance lists, maintenance tracking and emissions-reduction tracking tools. The actionable data may further be used as commands or scripts for automation systems 731. For example, actuators on a site may be automatically put in a safe position if an explosive concentration of a flammable compound is detected. Another example would be the operation of alert equipment such as sirens or visual cues triggered to alert operators to perform emergency evacuation if a toxic compound is detected. At times, robotic or automated inspection and repair or maintenance of equipment may be deployed as a response to a command. For example, a drone may be deployed to perform precise automated inspection of a certain area identified by sensing unit 733 to perform fine-scale equipment leakage detection. Another example would be automated excavation equipment which can be deployed for placing additional ground cover on a detected emission hotspot at a landfill. A third example would be triggering an automated self-diagnostic system in a continuous production environment which may require large computation power for distinguishing problems in the process.

Actionable data may be used to generate automated reports in document generation task 732. For example, the sensor data may be used to generate regulation-mandated emission inventory reporting and edit auto-completed reports to be physically or digitally sent to the concerned agency with or without operator intervention.

Actionable data, emission data and raw data may be transmitted to other servers 730, that may be internal or external. The purpose of this may be to relate raw data for archiving or post-processing, or to send data to servers behind a firewall in specific user instances where proprietary data is collected and require different levels of encryption. In that case raw encrypted data may not be decrypted in the centralized computing unit 727 for data safety reasons and may only be safely decrypted behind a client's firewall.

Actionable data such as triage information, reports, maintenance, and abatement data may be communicated through emails, text messages, dashboards, or dynamic notebooks, to static I/Os 729 and mobile I/Os 728. Static I/Os 729 can include PC and other fixed computing units such as in the office of the field manager. Mobile I/Os 728s can include pagers, PDAs, phones, tablets or laptop computing units and equivalents such as the phone of a field operator such as a pumper or a field foreman for oil and gas applications.

As seen in FIG. 7B, the centralized computing unit 727 processes the messages received by the sensing unit 733. Now referring to FIG. 8B, an embodiment of a method 800B executed in the central computing unit for converting the information received in messages 840 originating from the sensing system described in FIG. 7A is described. The message generation process described in FIG. 8B converts messages 840 into actionable data in the form of emission detection, localization, quantification, and qualification as well as other actionable data generated by an actionability engine 837.

First, in step 830, message 840, which may be stored in a server database 870 after reception, is routed to the server instance that is responsible for message processing. Message 840 includes the information formatted by the sensor system of FIG. 7A and may be constituted of spectral or concentration information as measured for a certain sample t (which is taken at the time t) as well as weather information and sensor metadata (such as, but not limited to, diagnostic parameters, GPS location and sensor ID). The message is first decrypted and decoded in step 831.

Figure 8B:
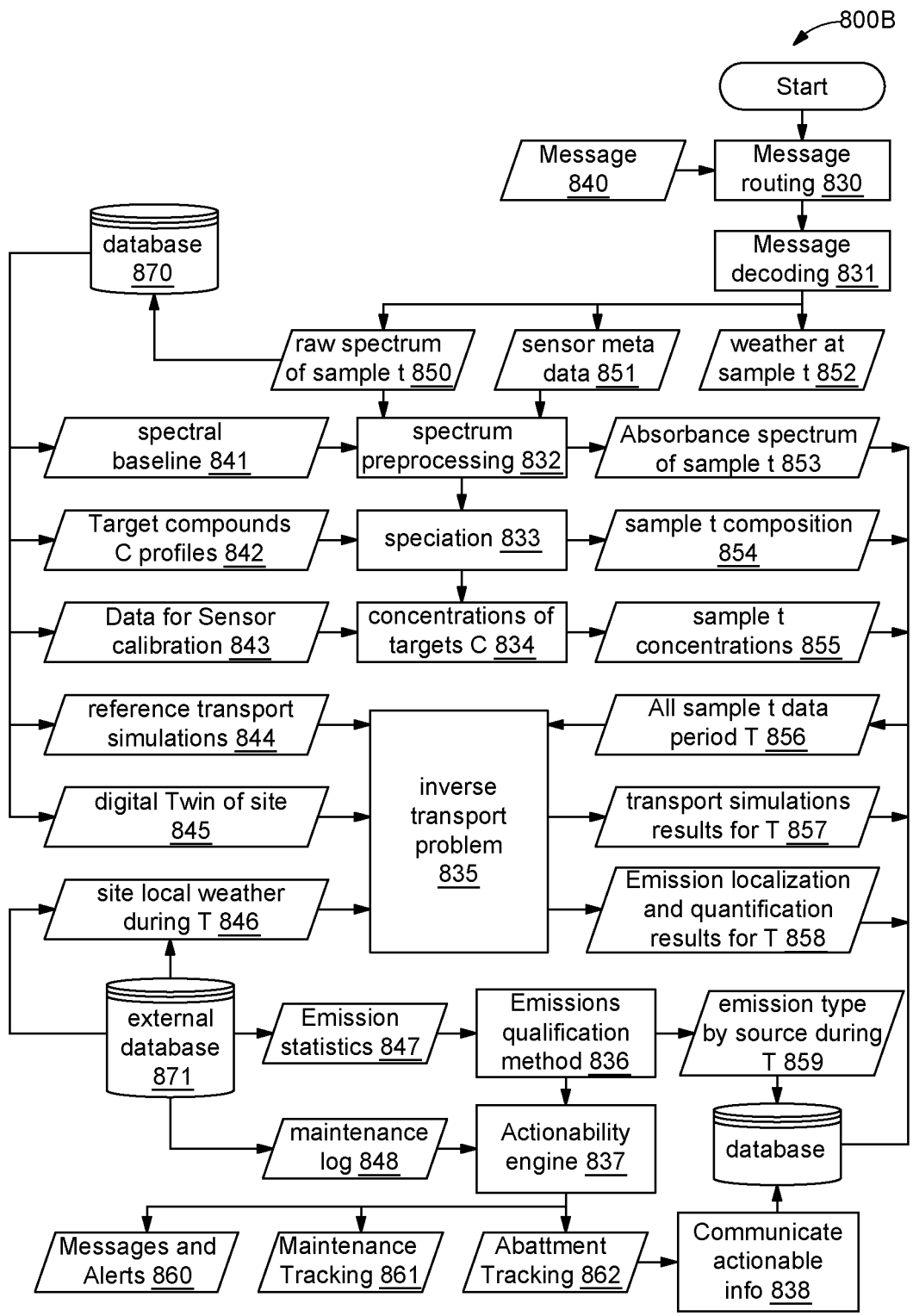
FIG. 8B illustrates an embodiment of a method for converting messages from the sensor systems via cloud implementation, in accordance with an illustrative configuration of the present disclosure.

Step 831 of FIG. 8B first uses a decryption protocol associated with the encryption method employed in step 815 of the message formatting as described in FIG. 8A. Message 840 may be parsed into three datasets: (1) raw spectrum 850, which may contain an absorption spectrum measured at sample t; (2) sensor metadata 851, which may contain sensor diagnostic, ID, GPS location and such; and (3) weather data 852 that may be taken around the time of the sample t. Raw spectrum data 850, sensor metadata 851, and weather data 852 may be stored in database 870 for future reference or for recalculation if new computation methods are later available. Note that raw spectrum data 850 is specific to an embodiment of the sensing technology and could be any other type of raw data associated with measuring the concentration of a target compound.

In step 832, the data of step 850 associated with the sensing of the target compounds is preprocessed. In an embodiment of step 832 for the specific case of spectroscopy sensor technologies, a raw spectrum is processed. The preprocessing includes denoising the data, peak alignment and bias shifting and computing an absorbance spectrum of sample t 853 from the transmission spectrum by using a spectral baseline 841 as a reference transmission. This step may involve sensor metadata for sensor-specific preprocessing, for example for accounting for light source power shifts, using sensor-specific information stored in database 870. Generally, regardless of the sensing technology embodiment used, step 832 may involve denoising, debiasing, or otherwise calibrating and enhancing the raw signal with preprocessing strategies that may involve sensor-specific information such that the preprocessed sensor signal may be analyzed.

Figure 8C:
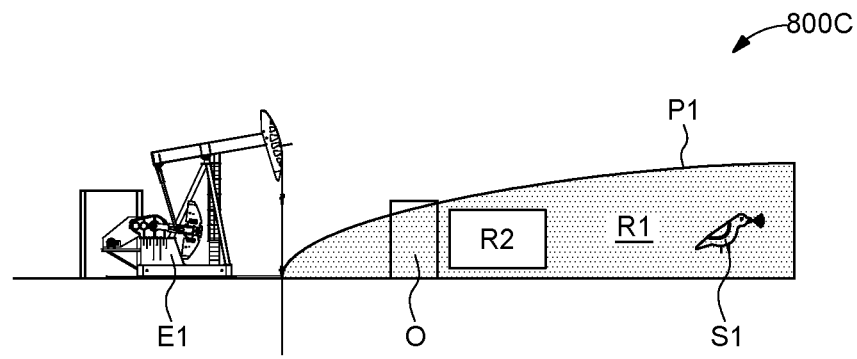
FIGS. 8C-8D illustrate a front view and a top view, respectively, of an example site that includes an emission source, in accordance with an illustrative configuration of the present disclosure.
Figure 8D:
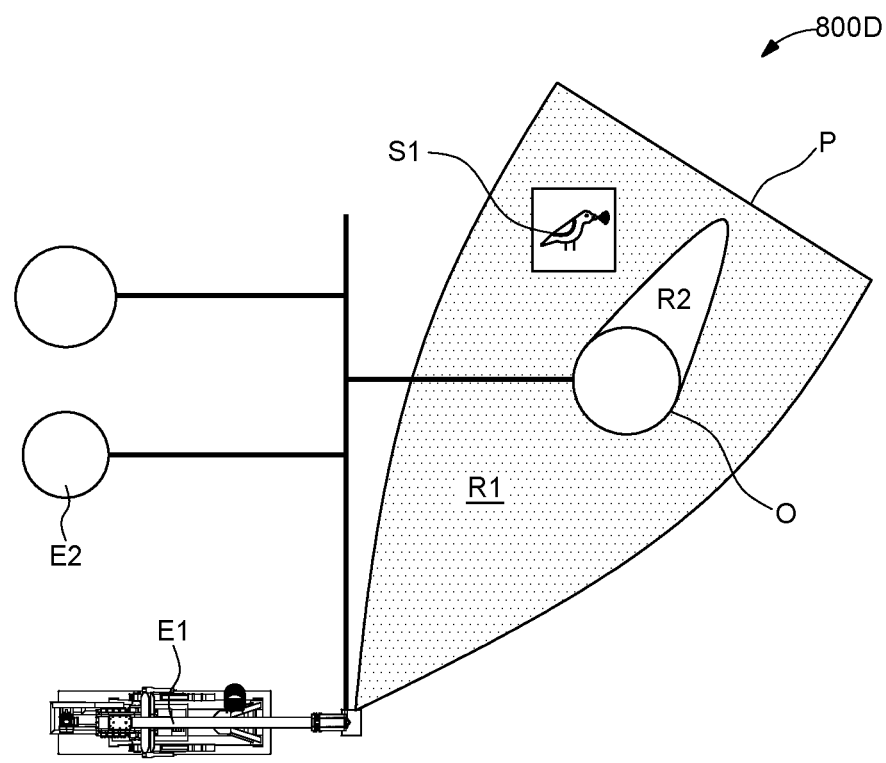

In step 833, the preprocessed sensor signal may be analyzed for speciation. The process of speciation involves the identification of various compounds from a raw signal. For example, FIGS. 8C-8D illustrate a front view 800C and a top view 800D, respectively of an example site. The site may include multiple potential emission sources E1, E2, etc. Further, the site may include a sensor S1. In the scenario depicted in the FIGS. 8C-8D, a target compound C1 is emitted from the source E1 and forms a plume P1 covering a region R1. Further, an obstruction O is present which may obstruct the plume P1. As such, the obstruction may result in a region R2 within the region R1 where the target compound C1 is not present or is minimally present. The sensor 51 which may be lying within the region R1 but outside the region R2 may detect the target compound C1.

Figure 8E:
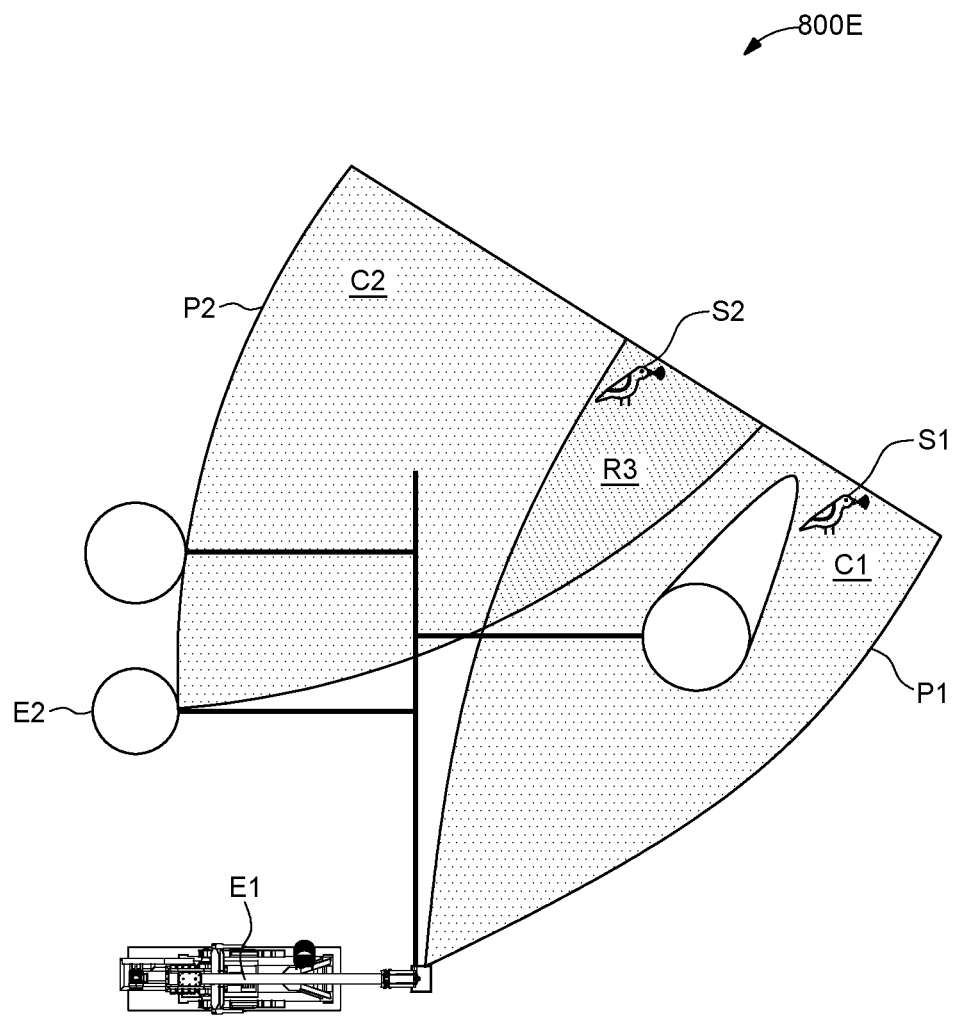
FIG. 8E illustrates a top view of a scenario with respect to an example site that includes multiple emission sources, in accordance with an illustrative configuration of the present disclosure.

Referring now to FIG. 8E, a top view 800E of another scenario with respect to an example site is shown where mixing of multiple target compounds takes place. As shown in the FIG. 8E, the site may include multiple potential emission sources E1, E2, etc. Further, the site may include the sensor S1 and S2. Target compound C1 is emitted from the source E1 and forms the plume P1. Further, a target compound C2 is emitted from the source E2 and forms a plume P2. The plumes P1 and P2 merge in a region R3. As such, the region R3 includes both the target compound C1 and the target compound C2. The sensor S1 which may be lying outside the region R3 may detect only the target compound C2. The sensor S2 lying in the region R3 detects both the target compounds C1 and C2 and therefore generates a confounding signal.

Referring back to FIG. 8B, the process of speciation therefore involves may involve identifying the contribution of one or multiple target compounds and separating them from confounding signals. This step may not be necessary for single-compound sensor signals that have no confounding elements. For the specific embodiment of a spectrometer absorbance signal, the identification may involve using reference target compounds spectral profiles 842 and minimization, inverse, or inference methods to decompose the spectrum into its component spectral signatures associated with target compounds. The target compounds profiles 842 may originate from the database 870 or from external spectral databases 871, for instance a HiTRAN database. A residual spectrum may be left over that may contain noise, non-linear contributions from light source and sensor bias over time and a spectrum of non-target compounds that may or may not be known.

A sample composition 854 for the sample t taken at time t is generated and stored in the database for the target compounds. This may further contain a residual signal for further analysis. Once the composition is identified, the concentration of each target compound in this composition may be obtained in step 834. For certain embodiments of the sensor technology, the concentrations may be obtained directly from steps 832 and/or 833. In one embodiment related to spectroscopy, the composition may be identified for normalized target compound profiles in step 833; the purpose of step 834 is then to associate the normalized profiles to a certain concentration. This may be achieved by using data from a specific sensor calibration data 843 as stored in the database 870. This calibration data 843 may be obtained by testing the specific sensor that has taken the sample t, or a reference sensor of the same type, with a multiple point test against a calibrated compound mixture. For example, when measuring methane, a five-point calibration in the range of concentration of interest such as 0 ppm to 100 ppm may be taken. The calibration data 843 associates a known concentration to spectral profile intensity, which may be nonlinear and can use the composition of speciated spectra from steps 833 to derive the concentration of each species of the composition. The sample t concentration data for the target compounds 855 is stored in the database 870.

Once the sample composition and concentration with respect to target compounds are found for a certain sample t, the localization, qualification, and some of the quantification is performed in steps 835 and 836. Step 835 focuses on solving an inverse transport problem. That may include a representative fluid mechanics model and models of the geometry, topology and other characteristics of the site surrounding the sensor system responsible for a set of measurement samples t. The model is created to recreate the condition in which the compounds of interest may be transported from the prospective sources and other confounding sources to the sensor system. The direct problem creates the relations between causes, such as source location and emissions flux for each source, weather at the sources, and consequences, such as sensor concentrations measurements and weather at the sensor.

The inverse model identifies the inverse relation; that is, finding the sources of emissions and emission intensities knowing the sensor system's measurements. This may be done explicitly by running a set of reference transport simulations 844 that may be stored in the database 870 for reuse and creating an inverse relation matrix to relate measurements with sources. Two inverse problems may also be run by first solving the flux inverse problem, i.e., finding the weather conditions at boundaries of a simulated domain that would result in the observed weather measurements by the sensor system, and then solving for the transport inverse system, i.e., what source's emissions would have resulted in the observed compound concentrations in the weather conditions found in the first inverse problem. The inverse problem may also be solved by modifying the transport equations such that they may run backward in time. Furthermore, local weather during the period of interest T 846 from external databases 871 may be used to enhance the selection of appropriate initial and boundary conditions in the solving of the direct or inverse problems. Together with this inverse problem solving, uncertainty quantification may be used to enhance the result and/or reduce the burden of large simulation sets by rewriting the problem as a function of probability distribution functions of the input parameters, formulating prior probabilities, and using statistical inferences such as Bayesian methods. This can help in source identification by explicitly solving for the probability that a prospective source is an actual source given the sensor system measurements and may reduce the number of direct simulations to an acceptable minimum based on known error distributions. Results of the transport simulations for a certain period T 857 may be stored.

In order to improve the inverse transport problem in step 835, all the samples t in a data period T 856 may be used by a solver algorithm. This is important because each sample t constitutes only a snapshot of the site for a given weather pattern. Therefore, in order to both build accuracy through repeated observations and in order to increase coverage of the site, a certain number of samples t are used, all within a contiguous period T. The period T is selected based upon the expected detection speed, the time necessary for the weather pattern, in particular the wind direction and speed, to change sufficiently such that the detection of potential emission for the observed sources is possible and based on the expected accuracy of reporting. The period T can shift from 1 minute, for example for the detection of critically dangerous compounds where emergency protocol may be engaged, to multiple months, for example at remote sites where intervention may not be possible or of concern for long periods of time. The period T may be dynamically, manually, or automatically allocated based on the sample t concentration 855 and composition 854, operator requirements, maintenance schedule, hazard, duration of emission and such.

Without loss of generality, the longer the period T, the higher the accuracy of the inverse transport problem in identifying average emissions over the duration T and with higher spatial resolution. However, in case of the identification of transient emissions, that is, emissions that may be intermittent rather than continuous, it may be better to select a duration T that matches the expected time characteristics of such emissions. In the embodiments related to upstream oil and gas, a judicious period T may be 1 to 2 weeks for emission monitoring purposes and shorter for safety purposes. In the embodiments related to solid waste, such as solid waste landfills and composting operations, a judicious period T may be from 5 days to a month when identifying cover hotspots and shorter for diagnosing well failures and for safety purposes.

The inverse transport problem 835 may be solved for various periods T using the same dataset in order to achieve different objectives. Once the inverse problem is solved, both the emissions probable sources and emissions flow rates for the selected period T, 858, are identified and stored in the database 870. This allows both the quantification (by identifying emission fluxes) and localization (by associating the probable sources with the site's equipment or areas). Then, emissions are to be qualified in step 836. The qualification allows further refinements of the understanding of the emissions. Indeed, emissions can come from different elements within an equipment but more importantly, emissions from the same equipment may be separated into categories of expected emissions from normal operation and spurious emissions from leaks or abnormal operations. For example, in the upstream and midstream oil and gas industry, equipment such as compressors and pneumatic actuators may emit methane in normal operation. In another example, landfills may have diffuse emissions depending on the presence or type of cover. This means that successfully detecting, localizing, and quantifying an emission may not mean that a leak has been detected, and may in fact indicate that the site is operating as designed.

One embodiment of step 836 uses statistical inference together with emission statistics 847 to identify the type of normal emission or leaks by distinguishing their intensity, frequency, and composition over time during a period of interest. Each emission type indeed has a specific signature in terms of intensity, frequency, and composition over time. Matching these signatures with the observations allows for the identification of emission profiles or outliers. The emission statistics 847 can be generated as a composite from equipment characteristics, for instance by accessing external databases 871 such as the Environmental Protection Agency (EPA) expected average emission by equipment type, by in situ statistical quantification by observing the emission profile of a site under normal operation, or by any other suitable experimental or theoretical methods to create such emission statistics. Statistical inference may be used to classify the emission type by source 859 which may be saved in the database.

The accuracy of the statistical inference can be improved by integrating a feedback loop, such as using operator data and/or maintenance logs 848. Indeed, these logs may be used to positively identify that a certain footprint was really indicative of a certain emission type. An alternative method to this qualification method embodiment may be to use artificial intelligence, machine learning, or neural networks. In this case, a training set is first created to identify the signatures of the emissions. The artificial intelligence method may learn over time by accumulating validation information from the type of emission through the site operator maintenance log 848. Over time, emission types may be more and more accurately qualified by a learning algorithm.

Once emissions are detected, qualified, quantified, and localized, this data needs to be provided in an actionable form to the end user. An actionability engine 837 provides this additional layer of intelligence by matching the characteristics of the emission to the needs and objectives of the end user. The actionability engine 837 may interpret the emission data, together with the maintenance logs 848, to provide three categories of actionable information. Some additional categories may be extracted from the data as well, may the need arise.

The first category is messages and alerts 860. The purpose of these is to relate the relevant information to the operator, to provide either a call to action or a status update. The messages may be, but aren't limited to, an indication of the current state of emissions in all the covered sites, a triaged list of emission flags ranked by intensity or gravity for maintenance intervention, and alerts in case of critical or emergency conditions due to the emitted compounds. For example, in the upstream oil and gas industry, a ranking of notifications or virtual "flags" for potential fugitive emissions may be sent to a field foreman in order to prioritize sites for inspection and maintenance. In another example, an alert for high concentrations of hydrogen sulfide may be sent to all field operators or pumpers in the vicinity of a dangerous hydrogen sulfide leak at a specific well pad. In yet another example, the emission inventory for a specific site for a quarter may be summarized for an operational field manager to track emission inventory objectives. This first category of actionable insights provides one-way, summary information that may be used for metrics tracking, safety alerts, or maintenance scheduling. Fundamentally, this first category does not have a feedback loop.

The second category generated by the actionability engine 837 may be a maintenance tracking system 861, where information from the operator may be used, for example as maintenance log 848, to actively update the maintenance strategy. In the oil and gas industry, the maintenance tracking system 861 could be used to track and schedule maintenance efforts based on available resources and to flag resolutions. For example, the maintenance tracking system 861 could limit the number of flags by avoiding notifying the operator multiple times for the same emissions until the emission is marked as fixed. For example, in the landfill industry, the flag associated with a particular hotspot may be suspended until the site manager confirms that cover remediation was attempted by adding more cover around the hotspot. In effect, the maintenance tracking system 861 can help ascertain that remediation for a particular emission was successful. The maintenance tracking system 861 may also suggest the most likely faulty component to look for based on a site's known equipment inventory. The maintenance tracking system 861 may directly allocate works to various maintenance teams based on availability of tools, human resources, and time. The maintenance tracking system 861 may suggest replacement parts when repeated leaks are detected from certain components, for example a particular actuator being known as faulty may be replaced by a better model to avoid the repeat maintenance cost. The maintenance tracking system 861 may send a triage list of unwanted emissions by intensity and suggest intervention speeds for each considering the likely maintenance cost, lost gas, and resource intensity requirements. For example, in upstream oil and gas, an open thief hatch identified as the likely emission source from a liquid tank would be rated as a high priority, as it is a high emitter, does not require specialized equipment to address or find, does not require large amounts of human resources to address, and is easy to verify. The maintenance tracking system 861 therefore does balance practical requirements with emission reporting for maintenance purposes and make use of operator feedback in its updating.

A third category of actionable information lies in abatement or emission reduction tracking 862. For this category, information over a longer time trend is analyzed. By collecting maintenance information and emission over long periods of time, emission inventories and repeat equipment failures may be compared across many sites. This may allow ranking sites which are attempting emission reductions by various strategies. For example, one site may use compressed air actuators in one oil field and low-bleed actuators in another and compare emission intensities of both technologies in real life conditions. This may lead to better decision making when implementing pilots for new, lower emission technologies. In particular, the cost per avoided ton of CO2 equivalent may be compared when using an embodiment technology which tracks greenhouse compounds. Emission inventory trends may be used to evaluate the efficacy of practice or equipment change using the abatement tracking system 862.

In general, the actionability engine 837 may involve a set of rules, algorithms, and artificial intelligence to generate actionable data for the messages and alerts 860, maintenance tracking 861, and abatement tracking 862. This actionable data may be stored in the database 870 and may be communicated to stakeholders in step 838.

FIGS. 8A and 8B have detailed an embodiment of a process for the conversion of weather and compound sensor measurements for emission detection, qualification, quantification, and localization, and for the generation of actionable data, insights, and maintenance and emission reduction tracking. The described method is not limited with respect to the type of sensor technology. The following presents the particularities associated with signal treatment in the near to mid-infrared region for an embodiment of the sensing technology which utilizes absorption spectroscopy. This region of the spectrum is of particular interest for detecting greenhouse gases, which are gases that absorb electromagnetic radiation in the infrared part of the spectrum and contribute to the trapping of heat when present in the atmosphere.

Figure 9:
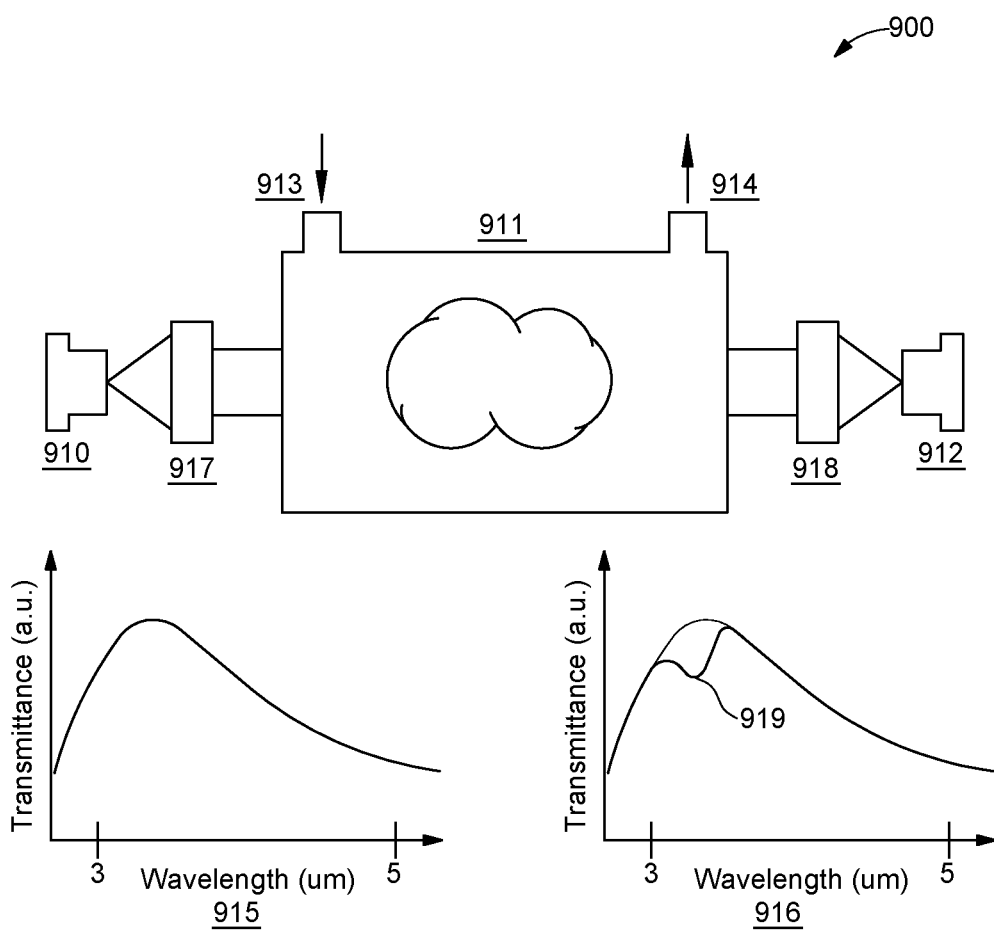
FIG. 9 illustrates a simplified graphical explanation of the physics involved in a specific embodiment of the sensing technology; namely absorption spectrophotometry, in accordance with an illustrative configuration of the present disclosure.

With regard to FIG. 9, a schematic representation 900 of absorption spectroscopy as a concept is given. The basic concept of absorption spectroscopy is to identify the presence and concentration of a compound by its ability to absorb light of particular wavelengths. An absorbance of a sample depends on concentration of the various compounds present and on a pathlength of light through the sample. This relation may be given by the Beer-Lambert law, which relates the absorbance of a certain compound to its concentration in a mixture. Compounds may be identified and distinguished by the unique set of wavelengths that they absorb.

The particular embodiment presented in FIG. 9 may use a source of infrared light 910, a gas cell 911, and a microspectrophotometer or infrared sensor 912. The light source 910 produces infrared light in the spectral region of interest. This source 910 may be a laser or light panel (e.g., LED light panel) with an acceptable spectral width, or another emitting source such as a filament or a thin-film resistive source which may behave similarly to blackbodies emitters. The sensor 912 may be a spectrophotometer or a light sensitive detector. This sensor 912 may be sensitive to light in the spectral region of interest. The spectrum may be obtained from tuning a laser to scan the spectrum of interest such as in a Tunable laser Diode Absorption Spectroscopy or TLDAS method, by using a scanning microspectrometer (such as in Fourier Transform Infrared or FTIR or Fabry-Perot Interferometry or FPI-based sensors) where a specific wavelength or interference pattern is sub-selected for observation in turn, or by having diffraction-based microspectrometer where the light is sorted based on its wavelength and projected onto a sensitive sensor array. One embodiment relies upon FPI-based microspectrophotometry using a broadband resistive light source 910. However, this configuration of the system, i.e., for the processing and analysis of spectra, may be applied to any sensing technology resulting in a measured spectrum of light and is in no way restricted. In particular, absorption spectroscopy relies on transmitting light through the sample, but aspects of the signal treatments can apply to different spectral methods, for example for Raman or reflection. In the case of the observation of particular matter compounds, nephelometry may be an alternative to spectroscopy, where the observed light is not the transmitted light through the sample but the scattered light at an angle from the cell that is not the transmitted light angle.

The sample cell 911 may be a cavity which contains a sample. The sample may be input through an entry point 913 and output through an exit point 914. Entry point 913 and exit point 914 may be the same point and the sample may be naturally fed into the sample cell 911 by wind (in the case of an open path spectrophotometer) or aspirated with a pumping system. Light from the source 910 interacts with the sample in the sample cell 911 and exits the cell to be collected on the sensor 912. The interaction occurs over the pathlength of light within the cell and the absorbance of the sample increases with pathlength. Thus, detection threshold and precision of the instrument may be improved by increasing the pathlength. Optical elements 917 and 918 may be used to collimate the light from the source 910 and collect or focus light on the sensor 912. Optical elements 917 and 918 may be reflective or transmissive optics elements or element groups suitable for collimation and focusing that would result in low diffraction and chromatism. These elements 917, 918 may or may not be imaging. In one embodiment, a single off-axis parabola is used for both optical elements 917 and 918.

The sample cell 911 may also contain optical elements to increase the light pathlength within the sample. Common strategies may rely on multipass cells such as Herriott, White, or circular cells. Other strategies may increase the pathlength by measuring extinction rate such as in cavity ringdown spectroscopy where pathlength can be increased to kilometers by creating a cavity with highly reflective surfaces. One embodiment uses a Herriott cell with collimated broadband light from a thin-film source, which is a novel way of using a Herriott cell with a broad source.

Graph 915 gives an example of a transmission spectrum before interaction with the sample. Graph 916 shows the transmission spectrum after interaction with the sample. In 915, the transmission spectra emitted by the source 910 is presented. In this example, these spectra are akin to a transmission spectrum of a blackbody radiator with a peak at 3.5 um. In the case of a typical tunable laser, this may look like a very narrow band of the spectrum (typically less than 10 nm), but some broadband tunable lasers exist as well. The light then proceeds through the sample cell 911 and exits after interaction with the sample. The resulting spectrum is depicted in 916. The black line spectrum is the exit spectrum, to be compared with the light gray curve representing the entry spectrum. An absorption peak 919 is identified. This is indicative of the absorption of a part of the light by the sample. The peak shape, width and position in the spectrum is indicative of the compound signature, and may depend on the instrument transfer function, temperature, pressure, and concentration of the compound in the sample. Other compounds in the sample may also broaden peaks. In the case of a laser-based system, the spectrum of the laser light may be very narrow, resulting in a very narrow transfer function and to the observation of the fine structure of the spectrum signature of the compound. Some spectrophotometers have a very large detection half-width resulting in the impossibility of observing the fine structure of a compound's spectral signature. It may therefore be difficult to identify and specify spectra obtained by large half-width spectrophotometers as the spectral signature of many compounds may look similar or may superimpose. While the following signal processing may apply for all spectral methods presented herein, it is specifically adapted for the interpretation of spectrum with transfer function resulting in the superimposition of the compound signatures.

Figure 10:
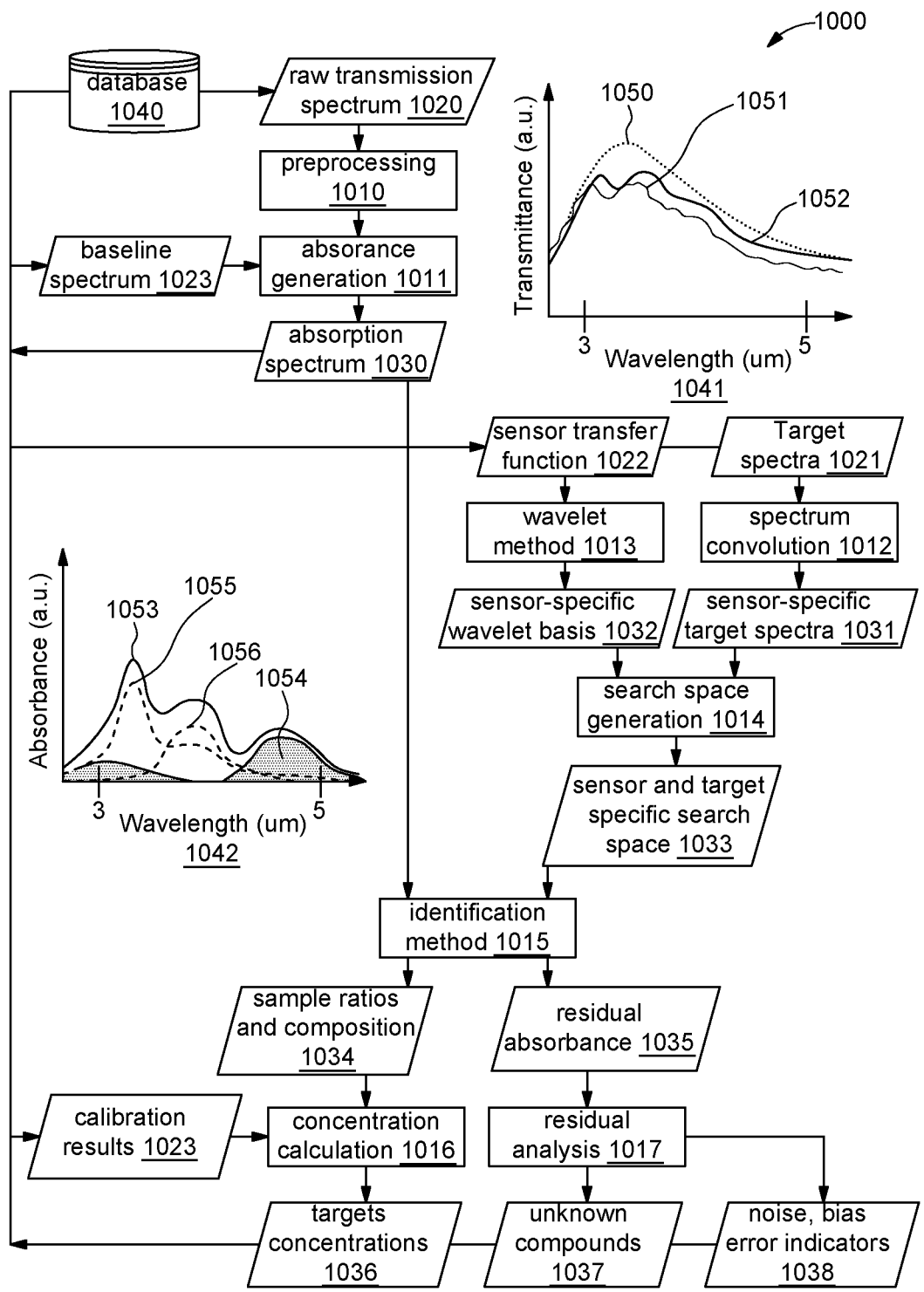
FIG. 10 illustrates a detailed description of the process involved in the interpretation of the spectra obtained from the embodiment of the sensing technology presented in FIG. 9, in accordance with an illustrative configuration of the present disclosure.

Now referring to FIG. 10, a flowchart of a method 1000 of processing of absorption spectra is illustrated. A graph 1041 presents a raw spectrum 1051 obtained from a compound sensor such as those previously described. This is denoted by raw transmission spectrum data 1020 stored in a database 1040. The raw transmission spectrum data 1020 (noted 1051 in graph 1041) is first preprocessed in step 1010. Step 1010 performs basic operations to improve the accuracy of the spectrum such as denoising, debiasing, and peak alignment. One potential embodiment of denoising may use a wavelet method where the transfer function of the potential instrument at various wavelengths is used to generate a wavelet basis. Such a method would allow for the rejection of noise which is not projectable on the wavelet basis, or which only contributes to the higher order wavelets. This may allow a significant reduction of noise from the raw signal. Debiasing may be performed on the raw signal or on an absorption spectrum by comparing the baseline absorbance to the expected baseline. This process is simplified by an embodiment of the debiasing which uses the wavelet described in this disclosure. When projecting to a wavelet basis, the lowest-order wavelets are indicative of the baseline and may be deleted with minimal loss of information about the absorption resulting from the target compounds. Peak alignment may be performed using reference absorption peak or baseline profile matching. For example, one potential embodiment of this is to use the CO2 peak at 4.2-4.3 um that is present within the observed spectra 1051 for the alignment, since CO2 has a high concentration in ambient air. Baseline matching may be obtained by the wavelet method by observing the baseline in the lower order-wavelets, resulting from the source emission profile, and by matching the profile to the known emission spectrum of the source.

The denoising, debiasing and peak alignment may result in the correction of the raw transmission spectrum 1051 into a processed transmission spectrum 1052. A light emission spectrum 1050 is given, which would be a native emission spectrum of the light source before interaction with the sample.

When preprocessing is finished in step 1010, an absorption spectrum is generated in step 1011. Absorbance is calculated from the transmittance obtained from the sample compared to a reference transmittance, which did not go through the sample. One example is to generate a differential absorption spectrum by using a sample observed at the site as a reference sample. This reference sample is selected from its low absorption in the zone where target compounds are searched, for example, from a wind direction where no sources are in the vicinity. The purpose of this is to eliminate the particular background of the site and to keep an updated reference sample to compensate for biases in the system from loss of performance of the light source, the sensor, or the optics. A reference sample is selected and taken as a reference baseline spectrum 1023 from the database 1040. This reference baseline spectrum 1023 is comparable to the light emission spectrum 1050 of graph 1041. The absorption spectrum 1011 is generated using the equation $A=-\log(T/T0)$, where A is a resulting absorption spectrum 1030, T is the processed transmission spectrum 1052 at step 1010 and T0 is the reference baseline absorption spectrum 1023. As an example, the resulting absorption spectrum 1030 is plotted as curve 1053 in graph 1042. The resulting absorption spectrum 1030 may be stored in the database 1040.

A second part of the processing may involve identifying compounds and their concentrations by their absorption signatures, and avoiding confounding agents such as unknown factors, residual biases, and noise in the signal. One embodiment of this identification may involve decomposing the absorption spectrum 1030 into its component absorption spectra, each associated with a target compound as well as a residual. To do so, one may use a wavelet method. In one embodiment, a sensor-specific wavelet basis 1032 to decompose the absorption spectrum 1030 is used.

A sensor transfer function 1022 is recovered from the database 1040. This may be measured for each sensor system or calculated from measured transfer functions of each subsystem. A wavelet basis may be constructed from the set of transfer functions 1022 when fit with Gaussian functions or other suitable fit. A wavelet generation method may be used for constructing wavelets in step 1013 resulting in a sensor-specific wavelet basis. In parallel, spectra of the target compound 1021 may be recovered from the database 1040. These target spectra 1021 may be constructed from reference measurements or obtained from an external source such as the HiTRAN database. In step 1012, the sensor transfer function 1022 is used to convert the reference target spectra 1021 into sensor-specific target spectra 1031 in a process akin to a convolution. This transformation simulates the peak broadening that would result from observing the target compounds' spectra through the sensor system. Step 1012 may be omitted if the sensor-specific target spectra 1031 are generated from experimental measurements on the sensor for each target compound.

In step 1014, a search space is formed for speciation of the absorbance spectrum 1030. To do so, a new basis is generated from the sensor-specific target spectra 1031 and with quasi-orthogonal residual basis selected from the sensor specific wavelets 1032 such that the resulting basis is complete over the absorption spectrum 1030. This basis forms a sensor and target-specific search space 1033, where an identification method 1015 is applied. Other basis generation methods may be used, to generate a quasi-orthogonal residual basis to form the search space.

In step 1015, a regularized minimization method under constraints may be used on the absorption spectrum 1030 to identify the coefficients associated with each term of the functional basis forming the sensor- and target-specific search space 1033. An example minimization method is a least-squares method under positivity constraints. Other minimization norms may be used besides the L2 norm, as well as other identification strategies based upon wavelet transform, Monte Carlo search, genetic algorithms, bayesian inference, neural networks or other machine learning strategies which may require experimental training sets of various spectra with known compositions. In some of these identification methods a search space 1033 may not need to be generated as it may be implicitly part of a prior training set.

Resulting from step 1015 may be a detected composition of the sample with coefficients associated with each target spectra 1034 and a residual absorbance 1035, which may contain information related to noise, biases, and unknown compounds. A graphical representation of this is given in graph 1042, where target spectra 1055 and 1056 may be identified from the absorbance 1053, as well as a residual 1054.

One particularity of the embodiment is that spectra originating from unknown compounds may be identified with the aforementioned method even if their spectra significantly overlap with the spectra of target compounds, specifically because the proposed search space relaxes constraints related to finding a fit with an unknown absorption profile.

In step 1016, the sample ratios and composition 1034 related to target compounds may be analyzed to identify the concentrations of the speciated mixture. For this, calibration results 1023 which relate the coefficients associated with the reference target compound spectra 1021 with the compound's concentration are used from the database 1040. These calibration results are obtained from experimental measurement using the sensor system or a reference sensor system and may also be calculated from a known absorption cross-section of the target compound stored in an external database such as HiTRAN together with a known pathlength of the instrument. This results in an estimation of the concentration of the target compound present in the sample 1036, which may be stored in the database 1040. Parallel to this, a residual absorbance 1035 may be analyzed in step 1017. This may involve reviewing prior residuals from previous samples on the same instrument for comparison. By doing so, unknown compounds that are repeatedly observed 1037 may be isolated over time, and noise, bias, and other errors may be qualified and quantified 1038. This can provide valuable insight on the accuracy of the sample identification in the form of error indicators, that may be used to generate upper and lower bounds in the identification of the target concentrations 1036. The unknown compounds 1037 and noise, bias, and error 1038 data may be stored in the database 1040.

Note that the analytics method presented in FIG. 10 may not only be applied to airborne or gaseous spectra but in general to any spectrum, and in particular those taken by low spectral resolution instruments where signal overlaps may be common. This may be applicable to identification of compounds in liquid spectroscopy, for instance in milk quality analysis, alimentary oils, lubricants, fuel and so on. In these cases, the optical cell may be reduced to a thin layer such that the composition of the sample may be observed without extinction at certain wavelengths. For example, a mid-infrared (2.5 to 25 um) methodology may be applied to identify water, soot, oxidation, nitration, sulfation, or other composite indices such as total base and acid numbers, and may be applied as a real-time, in-line instrument for the evaluation of lubricant quality on mobile or stationary mechanisms requiring lubrication.

FIG. 7C presents how a sensor system may be deployed in the field in a manner accounting for terrain, potential source location, transport obstacles and wind pattern. The underlying principle for uncovering a source is to sample from the plume of said source when the wind direction and speed point (in an average sense) form a line from the emission source to the sensor system.

Figure 11A:
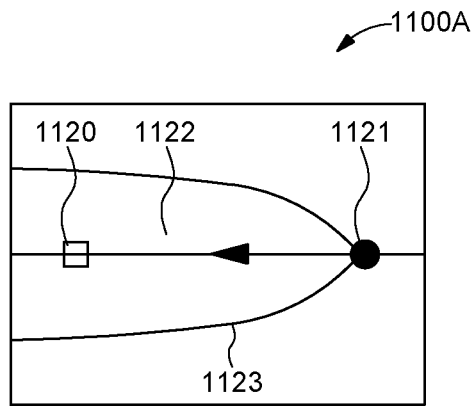
FIGS. 11A-11D illustrate multiple cases of the transport of a compound from a source to a sensor, based on wind direction, wind speed, and dynamic wind effect, in accordance with an illustrative configuration of the present disclosure.
Figure 11D:
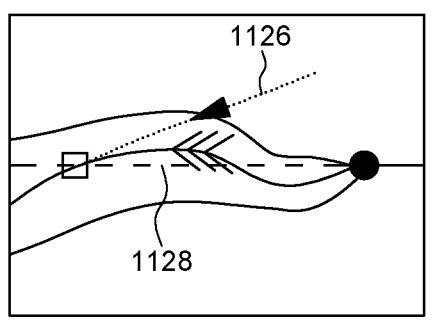
Figure 11B:
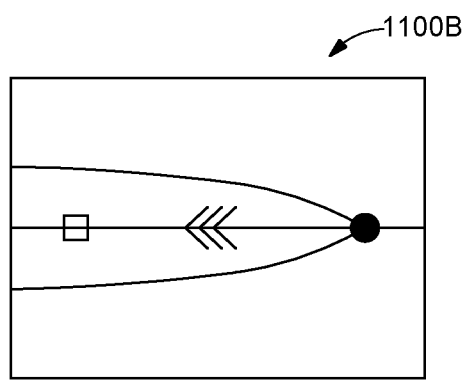
Figure 11E:
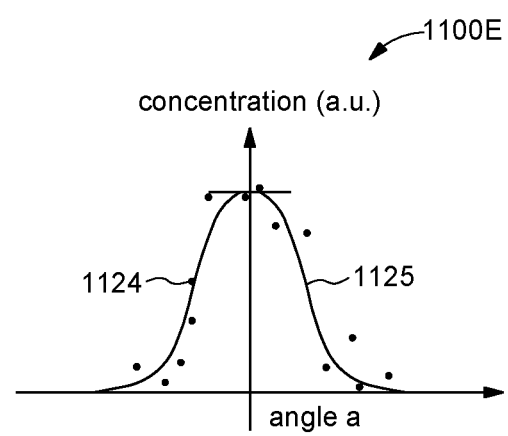
FIG. 11E illustrates a graph related to the concentration across the cross section of an emission plume, in accordance with an illustrative configuration of the present disclosure.
Figure 11C:
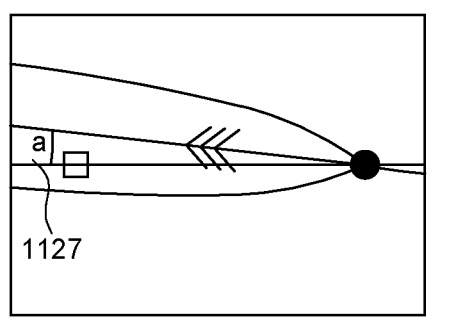

The fundamental principles of this plume detection are detailed in FIGS. 11A-11E. FIG. 11A presents a symbolic top view 1100A of the transport of an emission plume 1123 from a source 1121 to a sensor system 1120 via transport denoted by streamline 1122. In reality, the plume 1123 may not be contiguous and may have a complex three dimensional shape. FIG. 11A presents the transport in the case of a steady medium-speed wind pointing directly to the sensor system 1120. FIG. 11B illustrates a similar symbolic top view 1100B but with a faster wind speed. FIG. 11C illustrates another symbolic top view 1100C showing effect of a change in wind direction. FIG. 11D yet another symbolic top view 1100D showing the effect of a tortuous streamline. FIG. 11E illustrates a symbolic representation 1100E of construction of a plume cross-section using the wind direction to 'scan' across the plume.

Comparing FIGS. 11A to 11B, it can be observed that an increase in speed may result in a narrower plume extent since the plume spread is determined by a balance between diffusion and turbulent mixing, and advection, and at higher wind speeds, horizontal advection becomes the dominant force. This results in a change in an observed concentration at the sensor system 1120, namely that a maximum concentration observed across the plume may be higher in the case of higher wind speeds. However, higher wind speed can also result in more turbulent mixing in some conditions which may influence this result, particularly resulting in a large spread of measurements of maximum concentrations. This change from low speed to high speed clearly denotes the importance of wind speed in transport, and therefore the necessity to measure wind speed when measuring concentrations of the emitted compounds.

In FIG. 11C, the average wind transport is shifted angularly compared to the direct line from the source to the sensor as in 11A and 11B. Angle 1127 is denoted "a". In idealized conditions, an increase in "a" may result in a reduction of the observed plume concentration. The concentration in an idealized plume is maximum at the center. In practice, due to turbulence, the plume may be branched, and its cross section profile may not follow a regular pattern like the one shown in FIG. 11E. FIG. 11E presents an idealized profile of the cross section of the plume as measured by the sensor system 1120. The sensor system 1120 may sample the plume at different angles and register an associated concentration point 1124. When sufficient numbers are obtained, a fit of a point cloud 1125 can be obtained. If the measurements occur in idealized conditions when the wind speed, temperature and other parameters beside wind direction are stable, the plume flux may be calculated using a simple mass conservation equation by multiplying the area concentration of the plume cross section by its normal speed and by estimating the plume concentration in the height direction. This approach may be taken using plume theory for the estimation of the plume geometry and using a mobile sensor across the plume cross section to estimate the average plume concentration.

One illustrative configuration instead uses shifts in wind direction to estimate the plume average concentration, as depicted in FIG. 11E. Another, more precise embodiment is given in the description of the inverse model used to estimate emission source and flux. The wind may change dynamically during transport from the source to the sensor system 1120, as shown in FIG. 11D. FIG. 11D shows a case where the transport from source to sensor is on average direct as denoted by an average flow direction 1128 but may have a dynamically tortuous path. Moreover, a wind direction as sensed by the sensor system 1120 is shown as vector 1126. This exemplifies that in case of dynamic wind or when the topology influences the actual path taken by air flow, the source position may not be given by the wind direction measurement at the sensor system or at the source. This exemplifies the need for modeling of the air flow in the vicinity of the sensor to better understand the transport of the emission from a source to a sensor system when dynamic effects, obstructions, topology, or other effects may influence the transport.

Figure 12:
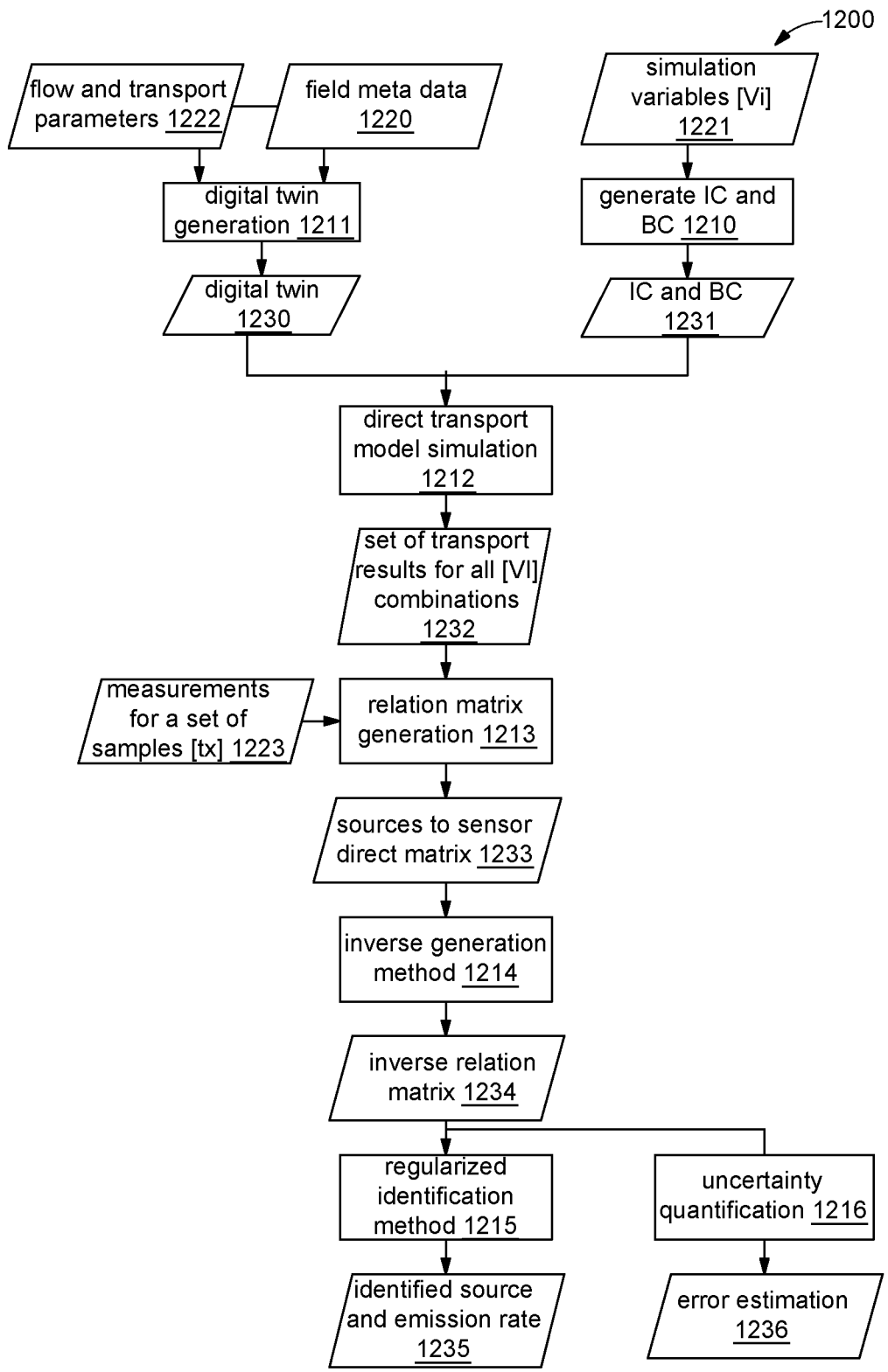
FIG. 12 illustrates an embodiment of a method to quantify, qualify and localize sources relying on transport simulation and a source identification strategy relying on solving an inverse problem, in accordance with an illustrative configuration of the present disclosure.
Figure 13A:
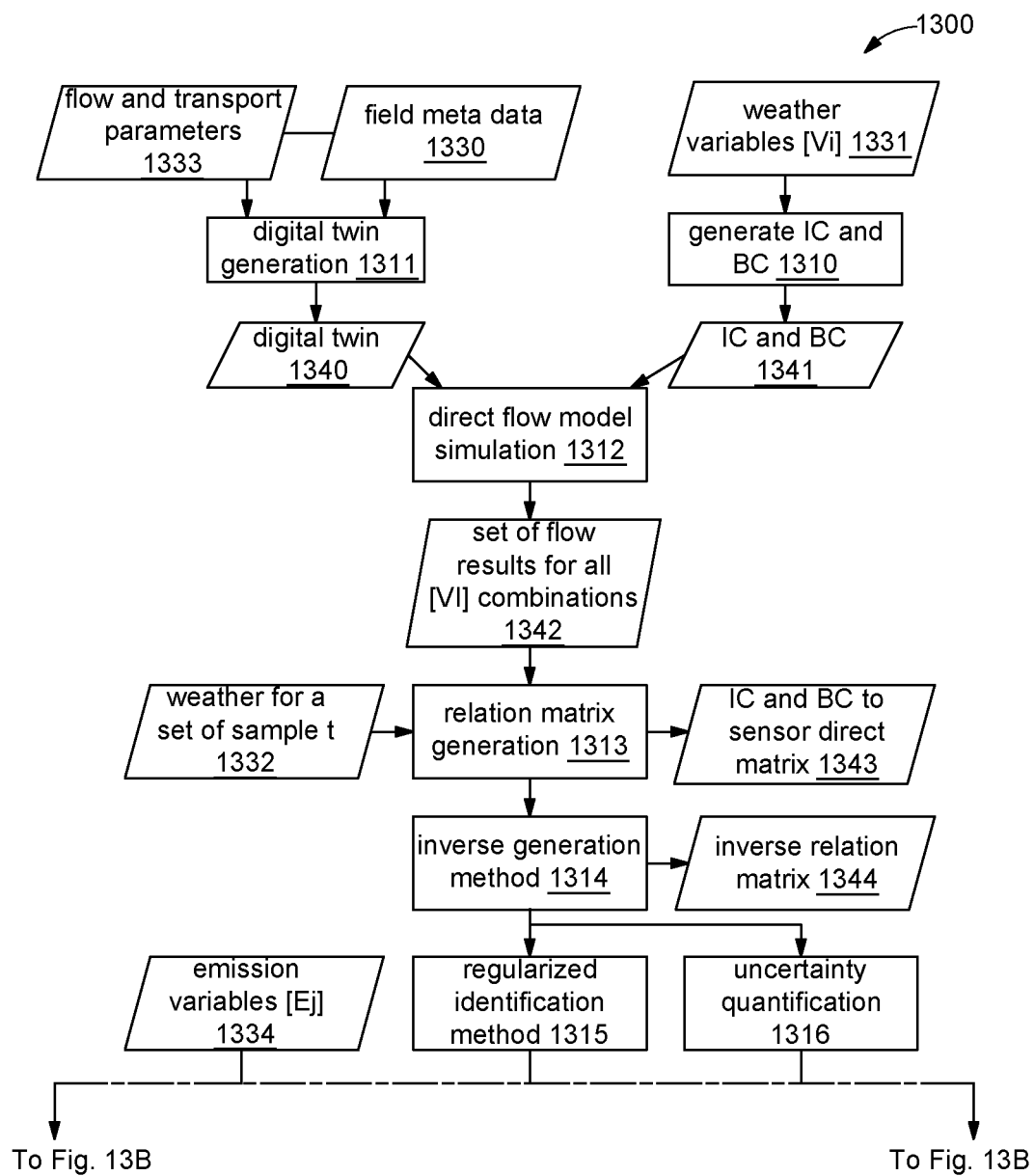
FIGS. 13A-13B illustrates another embodiment of a method to quantify, qualify and localize sources, in accordance with an illustrative configuration of the present disclosure.
Figure 13B:
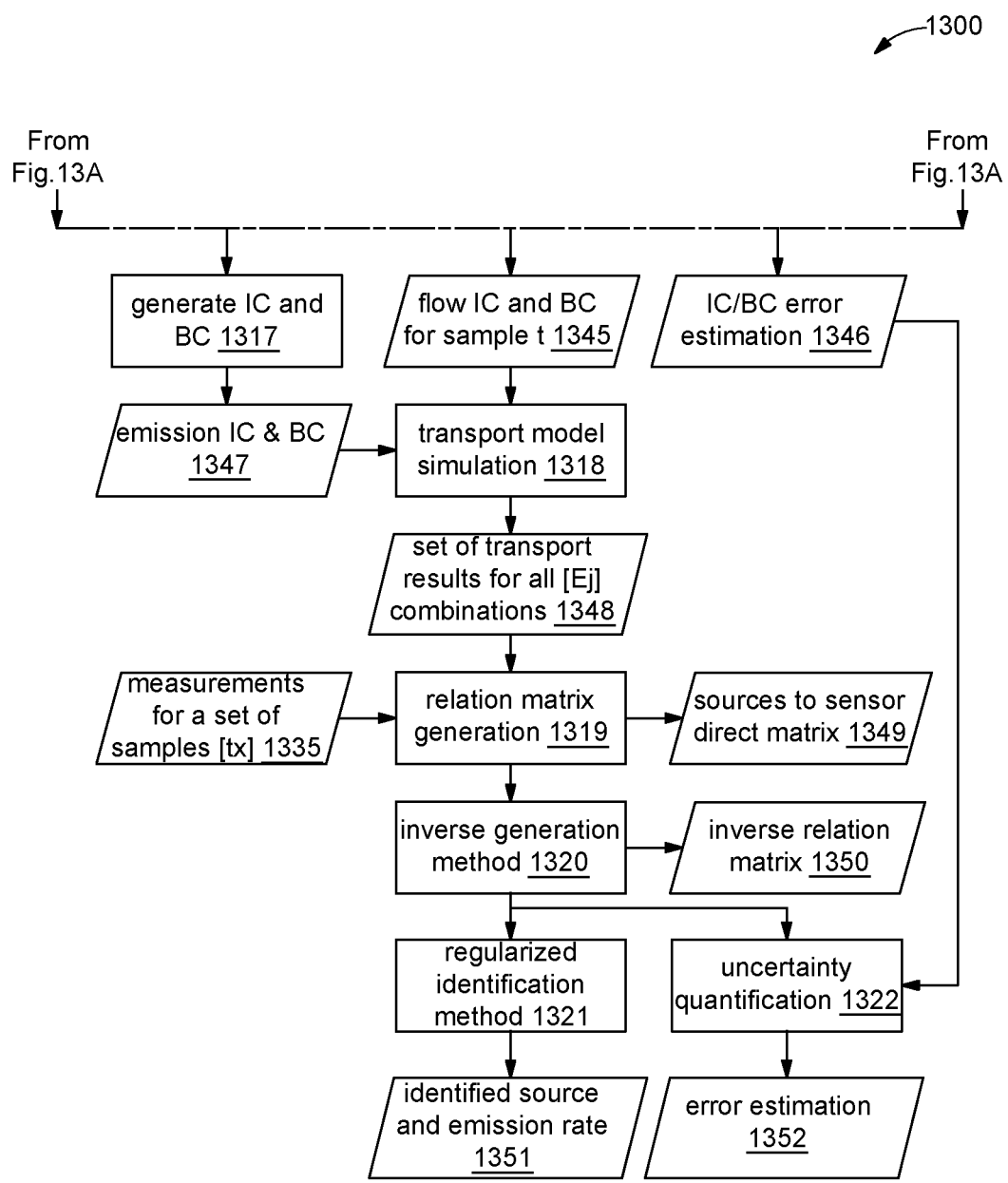

An embodiment of processes 1200 and 1300 for transport modeling including an inverse solver to identify source location and emission flux is given in FIG. 12 and FIGS. 13A-B, respectively. In both of these models, a digital twin of the site where the sensor system is placed is modeled and may include, without limitation, topology, obstacles, equipment on site, potential emission sources and a model of the sensor system itself. FIGS. 13A-B propose a complete solving of the problem with two distinct inverse problems being solved, one to identify the flow over the site and a second to identify the sources and emission flux. In FIG. 12, a single inverse problem is solved for localizing the sources while the weather over the site is found by matching the weather measured at the sensor location of a pre-simulated set of weather conditions. The method 1200 depicted in FIG. 12 may be used when the flux is easier to define such as when the wind is constant during sampling, with the advantage that most of the direct simulations can be carried out in advance and reused for subsequent source and flow identification. The method 1300 in FIGS. 13A-B may be suitable when the wind conditions are shifting during sampling and in complex transport cases. The method 1300 in FIGS. 13A-B may take longer to compute as it may be necessary to run direct simulations for the data processing every time a sample is analyzed. In both methods in FIG. 12 and FIGS. 13A-B, a probabilistic approach such as prescribed in uncertainty quantification or statistical inference methods may be used, in which case the simulation variables may be described as probability density functions in order to propagate an error estimator to the results such as a probability of positive source identification and error estimation on the predicted emission fluxes. The advantage of such a probabilistic method is that the number of pre-simulated models may be reduced or tailored to the precision requirement, thus limiting the computational cost of the methods.

Further, a method of identifying a target emission at a site is disclosed. The method may include creating at least one simulation model for the site based on simulation parameters. The simulation parameters may include a wind direction, a wind speed, an air pressure, an air temperature, a number of potential emission sources, a location of each of the potential emission sources, a source flux associated with each of the potential emission sources, a surface concentration, a weather condition, a hygrometry data, and an altitude. According to the method, actual parameters for the site corresponding to the simulation parameters may be received, receiving actual emissions measurements from a plurality of air quality monitors deployed at the site associated with the actual parameters for the site may be received. The plurality of air quality monitors may be deployed at predefined locations at the site. The method may include identifying a relevant simulation model from the at least one simulation model. It may be noted that the simulation parameters associated with the relevant simulation model match with the actual parameters. The method may further include extracting virtual emissions measurements generated by the relevant simulation model, and receiving actual emissions measurements from the plurality air quality monitors deployed at the site associated with the actual parameters for the site, correlating the virtual emissions measurements with the actual emissions measurements from the plurality air quality monitors, and determining configuration of at least one emission source based on the correlation. The configuration of emission sources may include a location of the emission source at the site and a concentration of emissions from the emission source.

In particular, with respect to FIG. 12, a digital twin (also, referred to as simulation model in this disclosure) is first constructed in step 1211. To construct the digital twin, field meta data 1220 (part of simulation parameters) is collected. The field metadata 1220 includes all the relevant information about the site in the vicinity of the sensor system at least containing the detection range of the sensor system. The field metadata 1220 may use satellite images, altitude, and topographic data to reconstruct the terrain, location of equipment, type of ground cover and so on. Furthermore, field metadata 1220 may be collected by an operator to ascertain the relative position of the equipment and sources relative to the sensor system, GPS coordinates of the sensor, list of potential obstacles, actual covers such as grass, earth, and trees, as well as a series of pictures of the site. These can be used to properly identify a geometry of the site and surface properties that may influence the simulation. Additionally, a three dimension cloudpoint of the site may be obtained by one or more scans, such as a LIDAR or radar scan. A numerical mesh or simulation grid is then constructed to represent a section of the atmosphere around the site that includes ground topology, large surface covers like trees, as well as discretization of equipment, obstacles, and the sensor system. Atmospheric borders of that mesh are defined as boundaries for the simulation and properties such as friction and slip may be attributed to surfaces associated with ground, cover, equipment, and other topological features. Sources are located in the mesh and identified as potential boundaries to specify emissions. The simulated volume may be as small as 100 by 100 by 100 meters (m) and as big as necessary to include a large field network, and the characteristic mesh size may be as small as 10 cm and as big as 100 m.

For example, consider the case of an upstream natural gas well pad. The well pad may be 100 m by 100 m. A sensor system is positioned on this site. Assume for this example that the sensor system is configured to detect methane and is accurate enough to detect leaks within 200 m in the conditions encountered at this pad. Satellite images give an accurate view of the pad, containing wells, separator groups and liquid tanks. The pad surface is identified by the operator pictures as gravel and the pad is surrounded by hilly grassland. The altitude is given as 500 m with a continental climate. A patch of pine trees lies to the north. Topological survey maps of the site are obtained in a national database. The sensor is positioned in the north corner of the pad and angular position and distance of the different equipment group is measured by an operator for validating the satellite images. From all this information a three-dimensional numerical mesh may be generated by an engineer. The mesh is a box roughly 300 m long by 300 m wide by 200 m high for this example with a mesh size of 1 m. The terrain is first created using point cloud extraction from the topological map. The equipment position is marked and three dimensional models of the equipment group, generated with a 3d modeling software, are positioned. The patch of trees may be added as individual trees or as a forest block with an appropriate diffusion model attached. The different terrain rugosity is attributed to the appropriate mesh elements. Boundaries of the 300×300×200 m box are specified for boundary and initial conditions. The surface of the potential sources, here the equipment groups including the well heads, separators, and tanks are identified as sources boundaries.

Consider another example, in the case of a landfill. The landfill may be 400 by 400 m and includes a 35 m high mound. Four sensor systems are positioned on the landfill. The landfill is surrounded by forested areas and the surrounding terrain is more or less flat. A service building lies to the north along an access road and a flare with a collection pond to the east. The landfill operator provides an up to date topological survey of the landfill. In this case, the mesh is 1200×1200×500 m with a mesh grid size of 5 m. The building and flare are 3d rendered as obstacles and the dense forest is represented as a diffuse cover group. The surface of the landfill is denoted as a source and divided into sectors of interest based on the landfill cover type and based on the location of the sensors. Each sector's emission may be evaluated individually in order to determine the presence of emission hotspots. The flare is also noted as a potential point source as are the individual wells over the landfill.

Parallel to the task of generating the geometry of the mesh and mesh surface classification in step 1211 (digital twin generation), simulation flow and transport parameters 1222 may be introduced. These parameters may facilitate the simulation by providing values for internal parameters such as diffusion of the target compounds in air, buoyancy of the compounds and boundary parameters such as typical atmospheric wind profile at the site's altitude and location, frictional parameters associated with cover type and such. These parameters 1222 may be collected from scientific studies, external databases, or experimental data. These parameters 1222 may be added to a generated digital twin 1230 to constrain and bound the digital twin 1230. Note that FIGS. 13A-B have the same process for generation 1311 of a digital twin 1340, from field metadata 1330 and flow and transport parameters 1333.

Now with respect to FIG. 12, consider a generation of initial and boundary conditions in step 1210. As stated earlier, FIG. 12 denotes an embodiment of the method where a set of reference simulations is conducted a priori to identify the relation between the virtual sources, their emission flux and the concentration measured virtually at the location of the sensor system in the digital twin simulation under simulated weather conditions. To do so, this set of reference simulations may need to include a large dataset to encompass weather conditions likely to be observed at the site as well as a combination of emitting sources at likely emission rates. A set of simulation variables [Vi] (i.e. simulation parameters) 1221 may include, but is not limited to, the wind direction (varying from 0 to 360 degrees, at 1 to 45 degree resolution), the wind speed (from 0 to 50 m/s, at 0.5 to 5 m/s resolution), the air pressure (+−150 mbar around the predicted nominal pressure at the altitude of the site, at 1 to 20 mbar resolution), air and soil temperature (+70-90 C, at 1 to 20 C resolution), potential emission sources (their location and number is specified by the equipment or sector to be monitored), source flux (from 0.01 g/s to 500 g/s, with resolutions from 0.01 g/s to 100 g/s), surface concentrations (in the case of diffuse sources, from 0 ppm to 10%, with resolutions of 0.01 ppm to 100 ppm), hygrometry (0 to 100%, from 1% to 20% resolution) or boundary layers altitude, if necessary. The number of simulations may therefore be high due to the dimensionality of the variable space and the resolution at which these simulations may be taken and may be carefully selected based on the site's specifics. For example, it may be unnecessary to run a reference direct simulation using temperatures under −15C if the site's lowest recorded temperature is −15 C. Furthermore, some parameters can be ignored if their variation does not fundamentally affect the transport result.

Each of the simulation variable combinations selected is used to generate the initial conditions (IC) and boundary conditions (BC) of a single reference simulation in step 1210. This step is repeated for each available variable combination. The initial conditions may include setting the sites temperature and pressure and initial turbulence pattern within the simulation domain. The active sources and their emission flux may be specified on the appropriate boundaries, and the wind conditions may be set on the simulation mesh external boundaries. The simulation of the digital twin 1230 under these conditions 1231 may be executed in step 1212.

In step 1212, a transport simulation is performed. Flux over the site is simulated by an appropriate closure of the Navier-Stokes function, for example, using a Large Eddy Simulation (LES) model which may be static or dynamic, and the transport is ruled by an advection-diffusion model. Simpler or more complex simulation models may be used here as long as the fidelity of that model is sufficient for the appropriate source allocation and emission flux quantification within the site operator requirements. The effect of gravity and earth's rotation may be considered when appropriate, that is, when the size of the simulated site calls for it. In other words, simulation parameters may also include effect of gravity and earth's rotation. The result of the simulation is a series of fields (i.e., virtual emissions measurements), static or over time, that describe the evolution or the steady-state of the concentration of the target compound across the site and in particular at the location of the virtual sensing system, as well as other flux and transport parameters. These results 1232 are accumulated for all the combinations of simulation parameters.

In particular, in step 1213, the weather conditions and the concentrations of target gases can be extracted from these simulations and directly related to the simulation variables related to sources and emissions flux. That creates a set of relationships between the potential emission sources and sensor (It may be noted that the term sensor and air quality monitor may have been used interchangeable in this disclosure) for certain weather conditions observed at the sensor location. A subset of these may be selected based on a set of measurements 1223 collected on the basis of real samples. In particular, the weather conditions measured from the site in a period of interest may be compared to the simulated weather conditions. For example, three samples may have been taken at 25, 24 and 25 C, and with wind speeds of 1, 3, 5 m/s and wind directions of 12 degrees, 24 degrees and 15 degrees respectively. It may be therefore possible to not consider other combinations of temperature, wind direction and wind speed from the reference set of simulations. Then, it may be possible that the resolution of the reference set does not match the exact condition monitored, in which case, the results may be interpolated across multiple reference simulations. For example, the sample at 24 C, 3 m/s and 24 degrees may not have been simulated, but a case at 24 C, 4 m/s and 24 degrees and one at 24 C, 2 m/s and 24 degrees were. The results in terms of concentrations may then be interpolated (i.e. correlated) to get a composite relationship between potential emissions sources, emission flux or surface concentrations (for diffuse sources) and sensors at 3 m/s. Additionally, multiple samples may occur in the same weather conditions, in which case, the sample concentrations may be averaged over the various observations in the same weather conditions, or any other appropriate weighed associative or multiplicative combination.

This process allows the creation of a set of relationships between virtual sources, prescribed emission fluxes or surface concentrations, and compound concentration measurements at the virtual sensor in weather conditions that matches the set of sample measurements [tx] of the real sensor over a period of interest. This relationship may be stored in a direct matrix 1233. The purpose of the inverse method is to identify the inverse relationship between source and sensor; namely, given certain weather conditions measured at the sensor, this method predicts the configuration of emitting sources and source flux/surface concentration from the measured concentration at the sensor during a period of interest. The direct matrix 1233 then needs to be inverted. In general, the matrix 1233 is an injection and may be ill-posed (generally due to rank deficiency); as a result, an inverse generation method may be necessary to inverse the matrix in step 1214. The most trivial method is to use the Moore-Penrose generalized inverse, which pads the relationship with zero eigenvalues, but any suitable inversion method may be used, in particular methods that specify more complex eigenvalue estimates; for instance, by complementing the solution space by appropriate fits that may minimize various norms or by constitutive-based approaches based on the nature of the equations used to calculate the transport problem. Regularized generalized inverse strategies may also be taken.

The end result of that inversion process is an inverse relation matrix 1234 that predicts the sources and their emissions or surface concentrations from a certain concentration observed at the sensor and given certain weather conditions. The inverse matrix may be evaluated for quality using its conditioning number as an error indicator or any relevant matrix invariant. In case of a bad condition number or equivalent error indicator, the condition number may be improved by varying the dimensionality of either the image space or the initial domain. In practice, this means that a larger number of observations may be chosen or that potential sources may be eliminated from the search in the hope of improving the well-posedness of the problem. For example, if the wind direction does not shift enough during the inspected period to observe all the potential sources of emissions, it makes sense to either eliminate from the relation matrix the sources that have no chance to be detected by the sensor (a source north of the sensor may not have a plume detected by the sensor if the wind is predominantly from the east in the sampling period), or by adding additional samples from an extended testing period where a sufficient number of wind directions are sampled to detect plume from all the potential sources of emissions.

A follow-up method for improving the quality of the inverse may also arise from regularized or tailored padding inverse generation methods, where the regularization or padding parameters may be explored in order to minimize the error indicator associated with the inverse matrix 1234, thereby improving the prediction accuracy of the method. Once a satisfactory inverse relation matrix 1234 is obtained, a regularized identification method 1215 may be attempted. The trivial operation is to perform a matrix vector operation where the matrix is the relation matrix 1234 and the vector is the set of concentration or concentration averages as observed by the sensor in the sample period of interest. If both the model and the detection instrument were perfect, this method could be applied straight away. However, the model and instrument are subject to error, which is generally greatly amplified by inverse methods. It may be therefore advantageous to regularize the inversion method. This may be done by adding constraints to the matrix operation, akin to a minimization, where the weight of the constraints may be tailored to optimize the result. For example, one potential constraint is to force values to remain close to the mean. Other methods may introduce ad hoc information about the error bounds of the instrument. Other strategies may be used for regularization for that purpose.

The weight of the regularization may be obtained using tools such as an L-curve optimization. In general, one may use similar inverse methods as the ones used for MRI image generation or seismic mapping. The result of the regularized identification method 1215 is a prediction of the sources that are actually emitting the target compound and an estimation 1235 of their emission rates for both point and diffuse sources and/or their surface concentration in the case of diffuse sources. Parallel to this process is an uncertainty quantification process 1216 which may provide an error estimation 1236 on both source identification and emission flux/surface concentration. The initial way to generate such error estimation is the estimated errors associated with the inversion matrix (through the intermediary of its condition number) and the upper bound of the measurement error (given by the sensor system accuracy and precision in both gas concentration and weather measurements). This error upper bound can be propagated to the result and used as a tolerance in the final result. For example, if the sensor system has a 1 ppm precision and accuracy, the surface concentration at the source is estimated at plus or minus 2 ppm at best. Furthermore, if the coupling is weak, say if a 10 ppm concentration at the source results in a 1 ppm concentration at the sensor for some particular transport conditions, the error at the source surface concentration is at best of plus or minus 20 ppm for the same sensor precision and accuracy. Similar error estimation may be given to propagate the transport model error on the end result.

Another strategy for uncertainty quantification 1216 is to use statistical or Bayesian inference throughout the process. That is, rather than solving the problem for a set of deterministic variables, probability distribution functions are used for these variables to indicate uncertainty; this results in a propagated uncertainty throughout the process which can then be used for error estimation. One advantage of this is that bottlenecks in the method may be identified through this approach such that they can be addressed either by improving the model or sensor system, or inversely by limiting computational or experimental efforts. For example, it may be unnecessary to simulate cases with wind direction at a resolution of 1 degree if the wind vane is only precise at 3 degrees. The uncertainty propagation can be tailored such that the uncertainty remains uniform across the solution space. Another advantage is that the probability of identifying a source may be extracted from that uncertainty quantification, and a percentage of source identification accuracy may be given.

Fundamentally, the method in FIGS. 13A-B is similar to the one given in FIG. 12. In particular, steps 1319, 1320, 1321 and 1322 as well as data 1335, 1349, 1350, 1351 and 1352 have similar description to steps 1213, 1214, 1215 and 1216 as well as data 1223, 1233, 1234, 1235 and 1236, respectively. The principal difference between the method of FIG. 12 and FIGS. 13A-B is that two distinct inverse methods are solved in the method of FIGS. 13A-B, namely that the weather conditions are first matched with an inverse problem and then the transport problem is solved, rather than a single inverse problem as in FIG. 12. This may be of interest when more complex weather conditions need to be simulated for accuracy purposes; for example, in a case where the wind is dynamic and not static during the sampling. In this case, it may be computationally intractable to simulate all the potential weather conditions, such that an inverse problem may be solved to identify the weather initial and boundary conditions that match the observed weather pattern during and preceding the air sample.

In the step 1310 a set of initial and boundary conditions is constructed from weather variables [Wk] 1331. These variables may be defined by first processing similarly to in FIG. 12, by using an interpolation of the average weather conditions at the sensor to derive the average weather condition at the boundary of the domain. This may provide a restricted domain to identify the dynamics of the weather condition around this average. The weather variables may be formed as a time basis over the duration of a particular sample. For example, the wind speed may be decomposed over time into a set of test functions that span the time domain such that wind speed variations during the sample may be accounted for. This may be done for all the weather variables and a set of initial conditions and boundary conditions is found 1341. This set is used, together with the digital twin 1340 to perform a direct flow simulation in step 1312.

These direct simulations may be dynamic simulations over the time preceding and during a sample such as the flow of all the air parcels contributing to the sample are represented. The result 1342 is given as a flow field over the domain, in particular at the location of the sensor. A direct relation matrix is then generated in step 1313 from this which relates the initial and boundary conditions of the domain and the observed flow and weather conditions at the sensor 1343. An inverse generation method 1314 may be used to form an inverse relation matrix 1344 which relates the weather measurements at the sensor with the initial and boundary conditions. A regularized identification method 1315, similar to the one described in step 1215, as well as an uncertainty quantification method 1316, similar to 1216 of FIG. 12, is then performed to identify the initial and boundary conditions that led to the weather measurement of the sample t 1345, as well as error estimation 1346 on the quality of that boundary identification.

A set of direct transport simulations 1318 can then be run for that sample t. Initial and boundary conditions of the sample t 1345 are used together with source initial and boundary condition 1347 for these simulations. Indeed, a set of emission variables [Ej] 1334 is formed to test all the potential sources, their emission flux and surface source concentrations that may contribute to the concentration of the target compound at the location of the virtual sensor in the model under flow conditions 1345. Sources and emissions are used to generate the initial conditions and boundary conditions associated with a certain source distribution in 1317. The emission initial and boundary conditions 1347 are then used in the transport model simulation in step 1318.

Step 1318 is repeated until all the simulations associated with each set of combinations of the emission variables are completed. This process (1313-1318) is repeated for each sample t of a certain period of interest. The sets of all transport results for all combinations of [Ej] for each estimated boundary conditions for obtaining the weather measurements at sample t in a set of interest [tx] is given in 1348. The process in steps 1319 to 1322 is then similar to steps 1213 to 1216 in FIG. 12, namely that the relationship between source, emissions, and sensor concentrations for that time period of interest is obtained (1319,1349), that relation matrix is then inverted (1320, 1350), and an identification method 1321 and uncertainty quantification 1322 are performed to identify sources, their emission flux or surface concentrations 1351 and their error bounds 1352. Note that the uncertainty quantification 1322 of FIGS. 13A-B have the specificity of being propagated from the error estimation 1346 evaluated for the specified boundary conditions.

Note that the methods described in FIG. 12 and FIGS. 13A-B may also be used in multiple target gas identification methods. In these cases, not only the source identification, their flux and or surface concentrations are sought, but as well their compositions with respect to the target gases. For instance, it may be possible to track both methane and propane at an oil and gas site, and different potential sources may emit different composition ratios, for example, the liquid tank emissions may contain a much larger fraction of propane than methane, when compared with a wellhead emission.

Figure 14A:
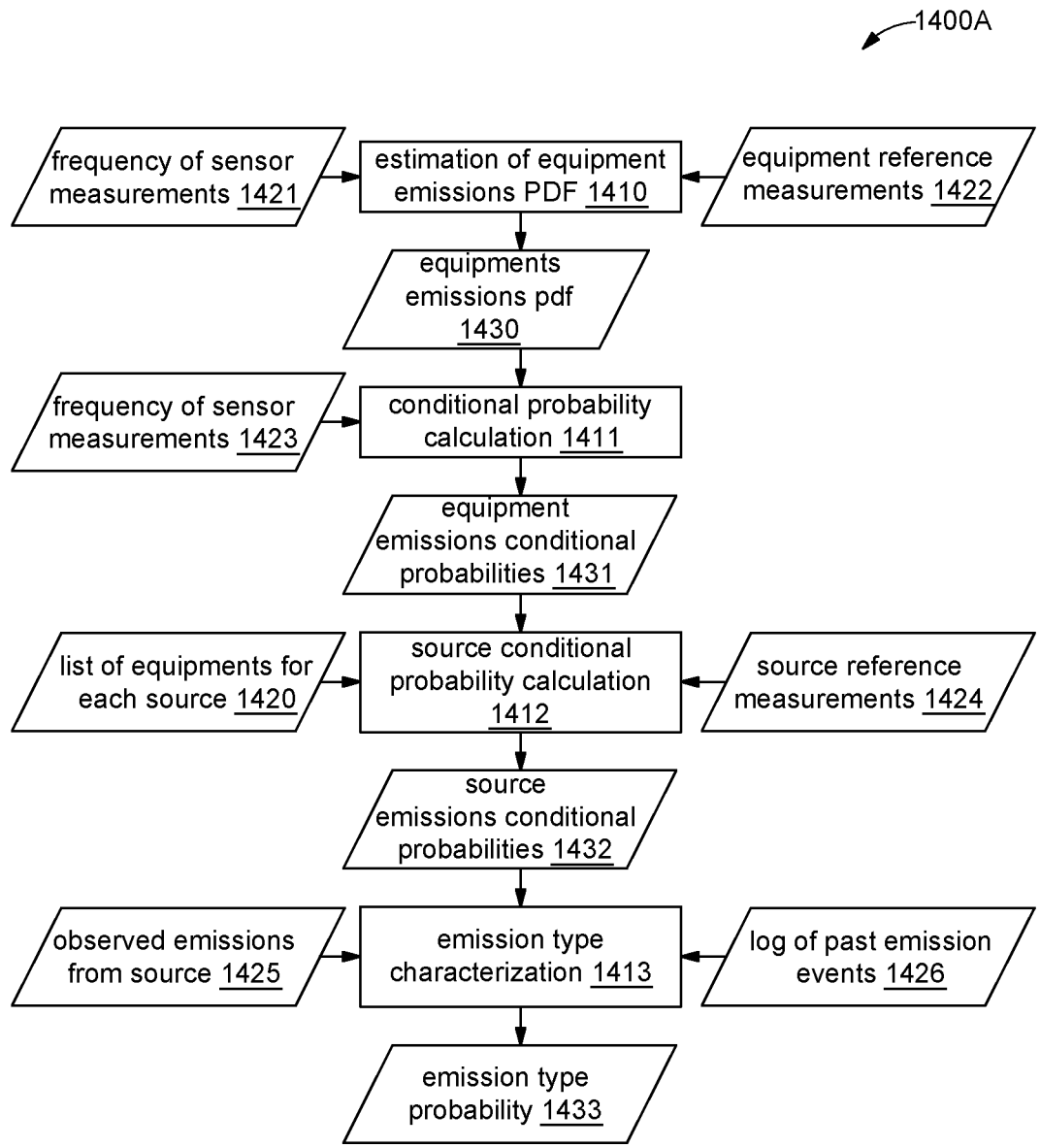
FIG. 14A illustrates an embodiment of an operational flowchart for the qualification of emission type using statistical inference, in accordance with an illustrative configuration of the present disclosure.

The methods presented in FIG. 12 and FIGS. 13A-B are possible embodiments to localize and quantify the emissions and their sources. Possible embodiments for the qualification of source with respect to their type is presented in FIGS. 14A and 14B. FIG. 14A presents a flowchart 1400A for construction of a statistical inference method where the emission type is distinguished from another by their characteristics in terms of composition, frequency or duration and intensity. This is particularly important to distinguish between allowed emissions and leaks since some equipment or activities may emit the target compounds as part of their normal operating process. One potential first step may be to create an estimation of the probability density functions of equipment emissions 1410. This can be done by collecting detailed descriptions of the equipment behavior currently deployed at a site 1421, which may include information or estimations about the emission frequency, intensity, and composition in normal operating conditions. This may be obtained from the site operator or from direct observation of the equipment type and using manufacturer- or industry-specific information to aggregate the emission frequency, composition, and intensity for the deployed equipment. Another source of information may be equipment reference measurements 1422, either for each type of equipment for a period of time or for the whole site to be observed, when the operations are supposed nominal (i.e., no leaks). This may be done, for instance, just after installing the monitoring equipment by first completing a full maintenance of the equipment for nominal operations and by observing the subsequent equipment reference behavior using the sensor system described herein in order to generate a set of reference measurements 1422. These measurements are then analyzed using appropriate statistical methods to extract the expected equipment emission frequency, intensity, and composition in normal operations. Similarly, specific failure modes resulting in fugitive emission may also be qualified if at all possible. For example, a stuck open valve may be voluntarily simulated to evaluate its emission profile if such an event did happen by accident. The result of this analysis is a set of statistical data characterized by probability density functions for the emission frequency, duration, intensity, and compositions 1430.

The characteristics of the sensor measurement 1423 are considered in step 1411 by the computation of conditional probabilities. Indeed, based on the sensor system placement, frequency of measurement of a certain equipment group, accuracy and precision of emission intensity, duration of sample and so on, the conditional probability of the observation of an emission given the characteristics and limitations of the sensor system is calculated from each equipment probability distribution function 1430. The conditional probabilities of equipment emissions 1431 may be used to generate composite conditional probabilities for each source in step 1412.

Figure 14B:
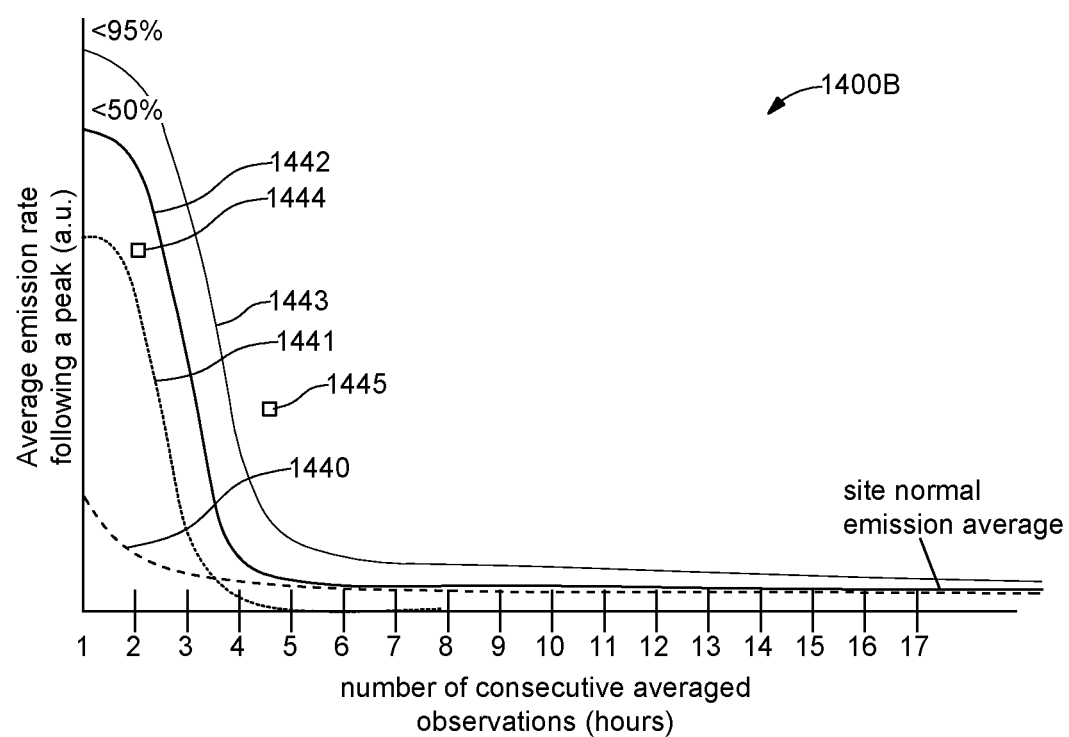
FIG. 14B illustrates a graph related to the number of observations and average emission rates, in accordance with an illustrative configuration of the present disclosure.

Indeed, a source may contain multiple equipment types. This may be generated as a composite of the equipment emissions conditional probabilities if a list of equipment for each source 1420 is obtained, or it can be constructed directly through the process 1410-1411 if source reference measurements as a whole 1424 are given. This leads to source emission conditional probabilities 1432 as observable by the sensor system. In step 1413, these probabilities may be used to qualify the emission types of various observed emissions from the source 1425, obtained by the sensor system. The conditional probability could be less adequate over time due to a plurality of factors such as weather conditions, seasonal changes, and operational changes at the well and shall be considered in a differential manner; that is, the record of past emissions events 1426 from that source may be used to continuously refine and update the initial conditional probabilities such that the number of false positives are minimized. In practice, the probability of an emission as observed by the source over a period of time is calculated from these conditional probabilities 1433. For example, in a natural gas upstream onshore site, a liquid unloading event may be identified when a high intensity, short duration and low frequency event involving mostly liquefiable hydrocarbons occurs; this may be distinguished from high frequency, short duration low intensity events such as methane puffs from pneumatic controllers. The probabilities obtained 1433 are analyzed and ranked based on likelihood. Emission events with high probabilities to be identified as a specific event or equipment type are sorted. Unsortable events which are unlikely to be normal equipment emissions may be identified as outliers. If such outliers have high intensities, these may be identified as fugitive leaks. An embodiment of a certain unqualified fugitive leak identification method through a graph 1400B is illustrated in FIG. 14B. In FIG. 14B, consecutive measurement averages as observed from a particular source are compared after a specific peak event is detected. The curve 1442 denotes the limit under which 50% of the nominal emissions are typically observed. Note that on small time intervals, the emission intensity average may be high, because it is dominated by normal high-intensity low-frequency events, noted by 1441, which may occur, such as liquid unloading. At long average periods, the curve 1442 tends toward the site long term nominal emission average. 1440 denotes the contributions from equipment that emits at low intensity but at high frequency, as exemplified by their large contribution to the site overall average over time. The curve 1443 denotes the limit at 95%, for which 95% of the observed normal emissions are under the curve. Thus, these curves may be used to identify the outliers. For instance, note that 1444 is under the 50th percentile and may likely be a normal emission. Furthermore, its high intensity makes it a likely contender for a high-intensity, low-frequency event of the type depicted by 1441. On the other hand, measurement average 1445 is outside the 95 percentile range, it may therefore be a fugitive emission, even if 1445 intensity average is lower than 1444. This method may be used to qualify the leaks. Note that the probability of some low-frequency event may collapse. For example, if only liquid unloadings are responsible for 1441, and if a liquid unloading occurred the week prior, the probability of a new liquid unloading this week is extremely low, which would make curve 1441 collapse and reduce the intensity of 1442 and 1443. In this case, 1444 may be considered to be a fugitive emission. It is therefore important to keep track of infrequent events in order to adapt the conditional probability to the specifics of a certain site's activity. Note that in general, leaks are either continuous or intermittent and can be generally identified in outlying deviations of the long term average, but early detection may be of interest as well. The embodiment of FIG. 14B may be supplemented with deviation estimates such as the calculation of a weighted integral of the evolution of observations averages over time and comparison of this metric to the 95% average.

Beside the detection, localization, quantification, and qualification of the emissions of a site for certain target compounds, specific metrics of interest may be considered such as total site emissions. A method of computation of such emissions is proposed herein.

Assume that detection, localization, quantification, and qualification of emission has been performed and that emissions are characterized for the site over contiguous time periods where both emission and weather have been measured and calculated.

In the case of point source and diffuse sources where the emission flux is known, this may take the form of average emission flux for all the emitting sources on the site over periods T, following each other. The average total emission of a site may simply be calculated as the sum of each emission flux for all point sources, which may be weighted by the estimated start time of each source emission, interpreted based on their probability of intermittency and smoothed over time. This process may provide a total emission estimation from one period to the next. Interpolation considering diurnal effects and seasonality may be used for padding the total flux estimate when measurements were unavailable, and total emission flux for periods of interest such as a week, a month, a quarter, a year or so on may be evaluated.

In the case of some diffuse sources, the emission flux may not be known directly, and surface concentrations may be known instead. This may be the case for sources at low pressure and high reservoir, where the emission flux actually depends on the transport rate. Assume that the surface concentration of a diffuse source across multiple sectors is known as an average for a certain time period and that weather conditions are known in its vicinity. A direct transport simulation of the digital twin of the site may be performed using part of the method described in FIG. 12 and FIGS. 13A-B. This simulation may be run with boundary conditions that match the weather conditions measured during the time period as well as the surface concentration as measured on the source surface. The direct simulation is then conducted for all the weather conditions as measured during the sample period and the outbound emission flux is calculated at virtual surfaces enclosing the source. Indeed, the flux may be calculated this way by measuring the concentration and area of all the virtual surfaces enclosing the source and multiplying it by the normal to the surface component of the local velocity field. This is equivalent to the mass conservation method employed for plume cross-sectional computation of flux but is conducted on the simulated digital twin. As a result, the flux of emissions may be known over time for a diffuse source from ground concentrations and wind measurements using a simulation model. Note that this method may be applied with measurements of the ground concentrations of the source, rather than calculated by an inverse method as in FIGS. 12 and 13. Indeed, this may be a practical methodology for landfill total emission estimation as landfill surface concentration measurements are routinely conducted to identify hot spots. The further use of wind measurement can then complement the measurement of surface concentrations, together with a digital twin, to provide a novel method for total landfill emission calculation.

One particularity associated with the use of a static sensor system for the detection of a particular emission is that the detection threshold of an emission may vary greatly based on external factors related to the transport of that emission from the source to the sensor. For example, a source hundreds of meters away from the sensor may be easily detected if a direct path and frequent weather pattern lead to the transport of the emission plume to the sensor, while a source of equivalent intensity, mere meters away, may never be detectable due to an impassable obstacle. Source interference may also be at play, for example when two sources are not separable from each other for being too close together or from presenting a similar angle of view from the perspective of the sensor, the closer source thereby partially occulting the more distant source. These considerations are schematically approached in FIGS. 15A-15D, representing in turn an idealized sensor 1520 and its detection limit 1521, the effect of local wind as exemplified by a wind rose 1523, the effect of topology as depicted by the isocline 1522 and the effect of occlusion by an undesirable source 1524, respectively.

Figure 15A:
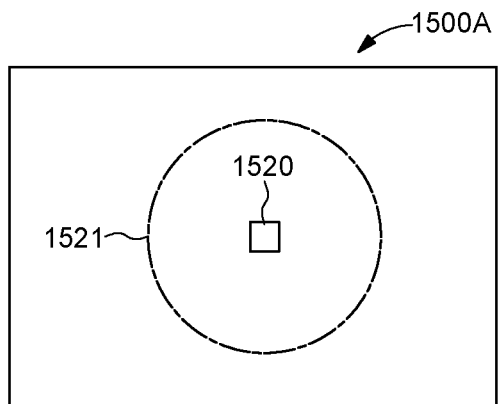
FIGS. 15A-15D illustrates a set of figures representing the effect of terrain, usual wind pattern and source separation on the detection area of a sensor deployed in the field, in accordance with an illustrative configuration of the present disclosure.

In FIG. 15A, a view of a schematic map of a sensor system 1520 is given. In this example, the topology is supposed to be flat, with no rheological effect from the ground. If the sensor detection limit is supposed constant and the weather uniform with wind direction equiprobable, the intersection of the detection limit of a source with a plan parallel to the ground is a circle. If the wind has no altitude term (normal to the ground), then the three dimensional view of that limit is akin to a cardioid centered on the sensor. In practice, the detection limit may take complex form due to external factors; some of them are presented in FIGS. 15A-15D.

Figure 15C:
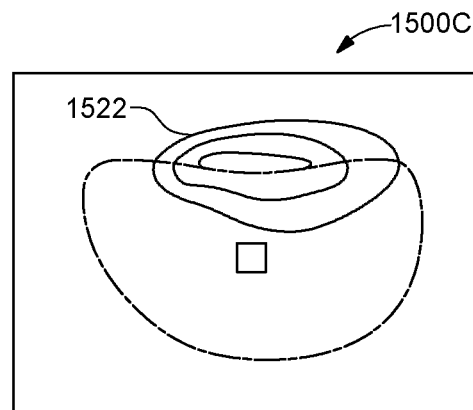
Figure 15B:
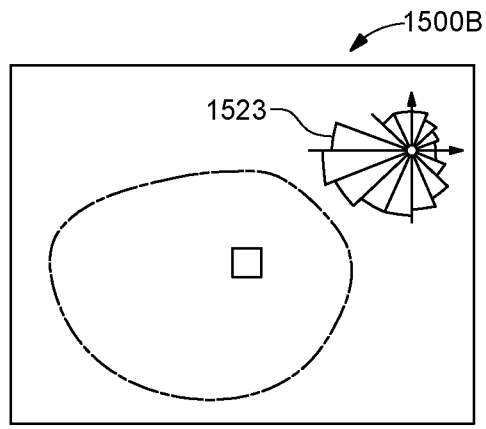

In FIG. 15B for instance, an average wind rose diagram 1523 related to wind speed for a period of interest is given. This deforms the detection threshold of the sensor system, allowing for detecting emission further away in the direction of faster and recurring wind. This is because of the relative weight of diffusion and advection on the transport of the emission, and faster wind increasing the distance at which a high concentration may be observed. Similarly, repeated observation in the same wind direction may reduce the effect of the noise of the sensing by averaging and decreasing the detection threshold of the system. The result is a non-uniform detection threshold curve.

Figure 15D:
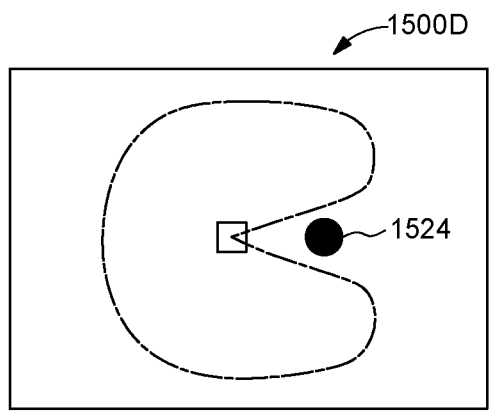

The effect of terrain and topography 1522 on transport is evaluated in FIG. 15C. As mentioned earlier in this disclosure, wind patterns may avoid obstacles which give rise to curved streamlines. If a topological feature 1522 lies in the detection area of a sensor system, this detection limit may follow the weather pattern topology and likewise shape itself following average streamlines. Further, in FIG. 15D, source 1524 may cause obstruction that limits the detection threshold in its vicinity. This can occur when one observed source blocks the detection of another source of interest in the same angular region, when two sources are not distinguishable because of being too close to each other, or when undesirable sources are interacting with the sensor. In FIG. 15D, an undesirable source 1524 is located within the detection area of the sensor. The detection area is then sharply reduced in the vicinity of that source because a source in the vicinity of source 1524 may be confused for source 1524.

Such consideration as presented in FIGS. 15A-15D may be taken into consideration when selecting placement of the sensor within a site and optimization of sensor networks which maximize detection while minimizing the overlap of sensor detection areas. Note that while one may use the concepts presented in FIGS. 15A-15D and other adjacent concepts to create ad hoc rules for sensor system positioning, this may only be performed in a qualitative manner. In order to effectively evaluate the practical detection area of a sensor, one may use an experimental or modeling approach. The experimental approach optimizes the positioning of the sensor by comparing expectations in detection to actual detection in the field, therefore effectively measuring the position of the detection threshold. This may be done using the potential sources themselves to generate data or by using a tracer correlation method. Another method relies on simulation to provide adequate information and estimation of the shape and size of the detection threshold. To employ such a method, one may use the direct transport model over a digital twin of the prospective site. The detection threshold may be found by testing the source-to-sensor coupling virtually by providing simulated test sources at various positions and distances from the sensor, therefore fully characterizing the detection area. Another simulation technique may only use the sources of interest and verifies that each potential source is located within the detection area of the sensor by simulating virtual leaks from each source at the wanted flux or surface concentration threshold. This may also be conducted at the network level, that is for large sites which may require more than one sensor.

Using this strategy, the detection area of a sensor may be described and fully utilized to the limit of the sensor system, thereby reducing the number of sensor systems to be deployed and maximizing coverage. In some embodiments, detection speed is also of interest, in which case redundancy of coverage from multiple sensors may be used to maximize the speed of detection. Indeed, wind direction may shift during observation and every detection that should occur faster than the characteristic time necessary for the wind to cover most directions may require more than one sensor in order to be detected in time. This requirement may be added to an optimizing network algorithm running the direct transport simulation. The positioning of the sensor may be adjusted in this simulation to provide maximized coverage at the necessary detection threshold and detection speed. This optimization may be performed by a random search (e.g., Monte Carlo method) of the space of positions for the sensor in which a minimum is sought that reduces the number of sensors and increases coverage. Other directed algorithms may be used, such as genetic algorithms or gradient-based algorithms to identify configurational minima. Machine learning, neural networks and other AI-based approaches may be used to provide adequate initial guesses to accelerate this optimization. Human experience may also be used for an initial guess.

The objective function that governs this optimization may be defined in success/failure metrics or by progressive scores such as measurement over detection thresholds and detection speed over desired detection speed. Measurement over detection threshold ratio may be optimized to be superior to 1 and detection speed over desired detection speed may be optimized to be inferior to 1. A minimum-maximum optimization is then performed to maximize the realization of the objective function while minimizing the number of sensor systems used.

The number of sensors and their position can then be chosen for the site by selecting the best optimization result with a sufficient margin of safety to guarantee operation over time.

Figure 16A:
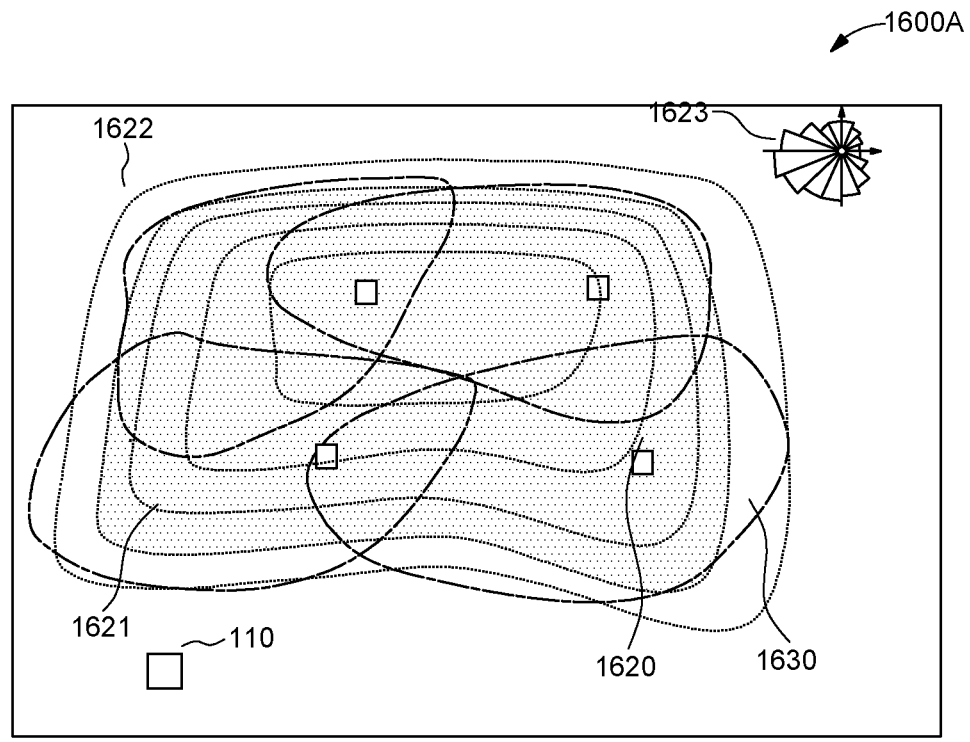
FIGS. 16A-16B show two symbolic maps of sensor network deployments for a diffuse source area and for point sources, respectively, in accordance with an illustrative configuration of the present disclosure.
Figure 16B:
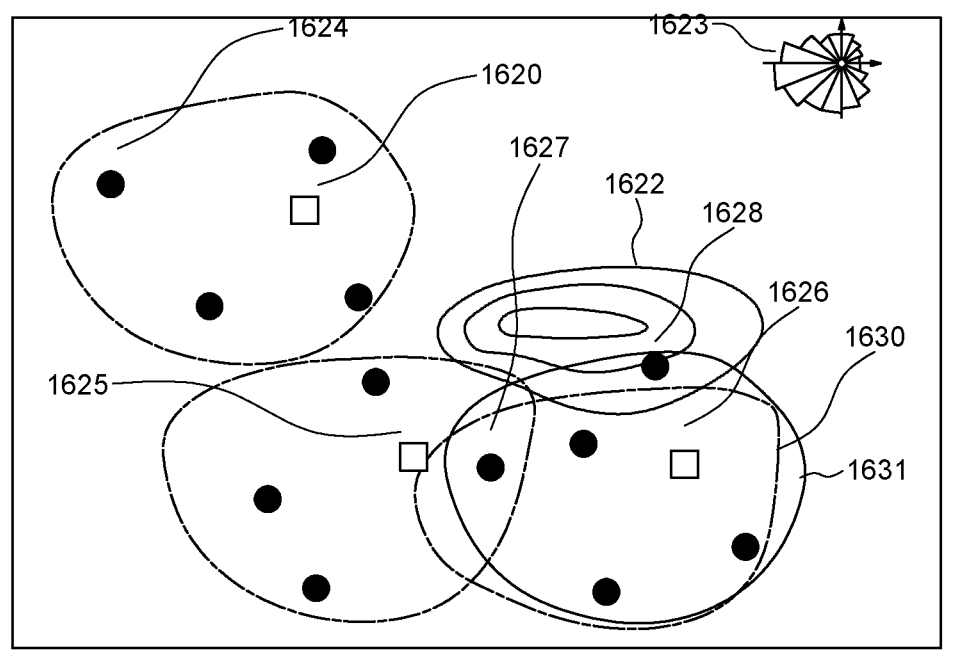

FIGS. 16A-16B illustrate symbolic maps 1600A and 1600B of sensor network deployments for a diffuse source area and for point sources, respectively. The symbolic map 1600A of FIG. 16A is constituted of two sensor networks, for a large diffuse source akin to a landfill. The symbolic map 1600B of FIG. 16B is for a site with multiple point sources, akin to an onshore natural gas field with multiple well pads. In both cases the wind speed and direction distribution are given by the wind speed rose 1623.

FIG. 16A shows four sensors 1620 deployed on a mound that is akin to a landfill. The isoclines 1622 denote the altitude change and the greyed area 1621 the diffuse sources. The dotted line 1630 indicates the detection threshold of the sensor 1620. It should be noted that a quasi-total coverage of the diffuse source is realized by the sensor placement choice and that the area of detection of each sensor is influenced by both the wind pattern and the topography of the land. Such a complex detection area may not be easy to define without a digital twin simulation without redundant coverage necessitating more sensor systems to be deployed. The diffuse source may further be divided into sectors that have equivalent emission contribution to each sensor and consider sensor area detection overlap.

FIG. 16B illustrates the deployment of sensors in a field with many sources (indicated by solid black circles) 1624 and three sensors (indicated by white hollow squares) 1620, 1625, 1626. Sensor 1620 detection area (dash-dot line surrounding 1620) is mainly influenced by the wind pattern, while sensors 1625 and 1626 are also influenced by the topology noted by the isocline 1622. The grey line 1631 denotes the hypothetical detection area of the sensor 1626 if the topology was not considered. Note that the source 1628 is not actually contained in the detection area of any sensor even though 1626 could hypothetically detect source 1628 were topology 1622 not present. Similarly, source 1627 may be detected by either of the two sensors; in practice, 1627 may be partially occulted by another source from the point of view of sensor system 1626. The coverage of the source 1627 by the sensor system 1625 provides distinguishable coverage of 1627.

The examples of FIGS. 16A and 16B exemplify the need for optimization in the deployment of a sensor network and the need for a fine understanding of the effect of external variables on the behavior of emission transport. The methods presented herein cover both conceptual, experimental and simulation approaches to optimize a network of deployed sensors that monitor emissions in real time. In some embodiments, the systems can include an air quality monitoring system and/or other systems or components disclosed herein. FIG. 16A illustrates the system including the air quality monitoring system 110 discussed in connection with FIG. 1 and can be programmed to receive output from the sensors 1620, 1625, 1626 via wireless, wired, and/or optical connections.

One embodiment of the disclosure concerns a method to generate emission predictions, preventative maintenance predictions, and targeted equipment and process replacement from existing data streams that may be interpreted to quantify, qualify, localize, and reduce emissions. Another embodiment of the technology can be a hybrid inspection method that may involve additional sensing modalities beyond static, real-time sensors, namely, fence-line monitoring, operator-based, drone-based, plane-based, or satellite-based systems that may or may not be used in conjunction with stationary sensing.

Another embodiment of the technology is a method for the monetization of emission reduction by taking advantage of financial markets. The systems can be programmed to identify emissions, track emissions (e.g., track for emissions credits/compliance), and manage emissions by controlling equipment, generating schedules (e.g., operation schedules), etc. For example, the system of FIG. 16 can be programmed to monetize emission reductions based on one or more monetization algorithms. The calibrations and source determination techniques of FIGS. 3-5 can be used to calibrate the system. Sensor deployment techniques discussed in connection with FIG. 7C can be used to select the number of sensors, sensor position, etc.

For the first method, existing data records regarding site operations, external or internal reporting, raw inspection data and other data sources can be used to inform emission quantification, qualification, localization, and reduction.

Existing data streams may come from existing processes and infrastructures that are related to the normal operation of the site. For example, an oil and gas-producing site may collect operational data related to product quality, operating pressures, volumes, temperature and other product characteristics, actuation of actuators, and so on. In another example, the landfill industry may record waste volume, compaction of landfill layers, landfill gas composition, landfill gas collection system pressure, and so on.

External or internal reporting may also generate data sources such as a record of past emissions, current equipment inventory, maintenance reports, or other reports, as needed or appropriate. For example, if a federal environmental agency mandates new oil and gas sites to report the equipment types present on the site, the system can estimate the normal emissions and leaks observed during inspections.

Raw inspection data taken from mandatory or voluntary inspections may also be mined for emissions data. Indeed, mandatory, and voluntary inspections may generate raw data that can create value beyond their current usage for inspection purposes. For example, in both the oil and gas and landfill industries, only concentrations higher than a certain threshold are reported to environmental agencies even though technicians collect raw data continuously throughout the site, regardless of whether it is above or below a threshold.

Additional external data sources may be used, such as the EPA emissions inventory which lists the average emission volume of target compounds like methane for each equipment type.

The data stream from these various data sources may be organized and analyzed.

First, the data may be organized into databases that describe each site and list the site equipment inventory, regulatory declaration of normal emission for a period of interest, regulatory declaration of emissions due to leaks, number and volume of leaks identified during inspections, and so on. An analysis may be performed to rank sites based on their emissions. Many sites may be compared, and outliers may be identified by comparing recent regulatory declarations of emissions compared to site emissions inventories, which may lead to identifying sites with higher emissions.

Second, timelines may be created for each site that may include the time-dependent operational data from each site, such as production volume, pressure, other measured product characteristics, external actuation settings and so on, as well as other data streams related to maintenance and reporting such as operator reports, part replacement, schedules for product unloading, repair due to leaks identified outside mandated inspection, site visits and so on. Each of the variables associated with an event may be quantified numerically and added to the timeline. Derived variables or events may be constructed by identifying the patterns in each variable timeline. For example, the event "transient overpressure" may be associated with an elevated pressure in the pressure measurement of a process.

The timelines generated for each site may then be analyzed to identify correlations between events emanating from different data streams. For instance, a statistical analysis may be performed by generating a cross-correlation matrix to identify correlations between events. For example, a large leak repair identified in the maintenance report may be correlated with a loss of product pressure from the operational variables.

The timelines of each site may be analyzed across sites. For instance, statistical trends may be established by comparing the cross-correlations of events happening at many sites. The results of this analysis may be the identification of repeat failure for certain types of equipment and the prediction of failure by the observation of correlation between failure and atypical operational measurements such as production volume, composition, pressure, temperature and so on. The analysis may further correlate elevated operational emissions with operational practices, such as excessive venting due to uncontrolled pressure in a controller PID. Such analysis may be performed using statistical tools or using artificial intelligence algorithms such as classification algorithms to create separate event categories and machine learning to identify correlations. The machine learning algorithm may be trained on validated data by operators that understand the causal relationship between process variables and emission behavior. Centralized computing units and databases (e.g., centralized computing unit 727) can store algorithms, models, lookup tables, and other data.

Third, raw inspection data may be analyzed. This may include the analysis proposed with the static sensor from one illustrative configuration described or other sensing strategies. Some sensors used in the inspection may produce concentration measurements or emission flux measurements in the vicinity of various equipment. Some also log the gps coordinates of the measurement or the equipment that was measured. This concentration or emission flux list, together with weather data—from the weather agency at the location of the site at the date of the inspection, or from local weather measurement—may be used to plot a concentration map or emission flux map of the site. The concentration or emission flux map may be formed by localizing each measurement on the site and interpolating the measurements at positions where no measurement was made. Depending on the nature of the site, the concentration or emission flux map may be only defined on the sources or in the direct vicinity of the sources. This concentration information may be used to run a simulation of the forward transport of the species concentration by specifying boundary and initial conditions that match the weather conditions of the day of the measurement. The transport simulation result is further interpreted to evaluate an estimation of the total emission rate of the site on the day of the measurement. This may be further extrapolated in time, by assuming constant emission and by varying the weather conditions to match later dates. The emissions may be inconsistent, and the sources may be adjusted using various data sources, in particular, the operational and maintenance data timelines presented herein, as well as subsequent inspection or other sources of measurement. Indeed, the method presented herein proposes a continuously updated digital twin of the site's emissions using data streams from various sources to intermittently reassess the emissions profile. Such processes may lead to improving the total emissions estimate of a site in the absence of high-frequency or real-time measurements.

This approach is for instance very fruitful for the case of landfills where the mandated inspection measures surface concentrations on the entirety of the site. The mandated inspection only mandates the report of concentrations higher than an allowable threshold, above which maintenance of the landfill cover is necessitated. However, the raw inspection data may contain concentrations for all measurement points. Using this data together with wind data from the landfill is a novel method for the prediction of total landfill emissions.

Sites may be compared and the datastream analysis methods proposed herein for reporting data, operational data, and inspection data may be used concurrently to (1) Evaluate total emissions, (2) Identify higher-emission sites, (3) Identify systematically failing components or equipment types, (4) Identify operational practices or equipment leading to higher emission, (5) Predict failures from operational measurements, (6) Identify mismatch between reported emissions and predicted emissions, (7) Identify best practices and equipment types limiting emissions, (8) Identify lower emission sites, and/or (9) Identify low-maintenance components or equipment types. The systems and methods disclosed herein can be configured to provide one or more of (1)-(9) discussed above.

This information may be used to provide actionable insight to the operators. In particular, the evaluation of total emissions may be used to improve the accuracy of reporting. Higher-emission sites may be selected for higher-frequency inspection and maintenance. Systematically failing components may be phased out to limit maintenance cost. Operational practices and equipment with higher emissions may be replaced for reduction of emissions. The prediction of failure may be used to trigger preventative maintenance to avoid downtime and reduce emissions. Emissions reports may be revised if reports are related to a regulatory risk where reporting accuracy is later judged by inspections. Best practices and equipment type reducing emissions may be extended in their scope to reduce emissions and maintenance cost. Lower-emissions sites may be inspected less frequently, thus reducing inspection budget. Low-maintenance components may have an extended use to limit maintenance across the sites.

The quality of the information obtained by existing datastream analysis may be enhanced by increased inspection frequency such as through the static monitoring device described herein and may justify the usage of static monitoring for some sites. However, real-time monitoring may not be the most cost-effective method for inspection for all the sites or at all times. A method for dynamically selecting the most effective inspection method based on the datastream described above is presented herein. Other inspection methods such as operator-based, drone-based, plane-based, satellite-based or fence line monitoring may be used together with continuous monitoring from static sensors to provide a holistic approach to monitoring. Indeed, some sites may have topological, environmental, technical and/or economic criteria that would make a particular embodiment of a compound monitoring system more worthwhile from an emission reduction perspective at a certain time. For example, densely packed oil and gas production sites that produce large volumes, as well as compressor stations, tank batteries or other concentrated sites with a large number of potentially emitting sources, may be ideal for continuous or close to continuous monitoring; while remote, sparsely located, low production volume sites may gain from being monitored less frequently by aerial inspection. Similarly, the emission risk over the life of the equipment may change significantly and as a result the optimal inspection strategy may change over time. Finally, the overlay of different inspection methodologies may change the inspection requirements of a site based on the availability of information about emission at a certain time and the rapidity with which a particular inspection embodiment can be deployed.

The technology can dynamically blend different data-sensing methodologies to provide a hybrid method which may utilize more of the advantages of multiple embodiments of disparate systems for the measurement, quantification, localization, qualification of emission of certain compounds as well as for the reduction of such emissions, all while optimizing for capital utilization. Different types of sensors can be used on a site. The number of sensors, sensor functionalities, and/or sensor configurations can be selected based on the sensor locations.

In particular, the analysis from the existing datastream informs about which sites are large emitters and which sites are emitting less. If an operator has many sites, such as in the upstream oil and gas industry, having different approaches for different sites may be a cost-effective emissions reduction strategy. For example, in the oil and gas upstream market, approximately 20% of sites may be responsible for 80% of the leaks by volume. This would suggest that the budget dedicated for monitoring, as well as the frequency of monitoring, should be highest in this 20% of sites. These sites may be identified through the data streams presented herein. Prevalence of failure points also influences the necessity of monitoring. An oil and gas site, for instance, with numerous wells and other systems such as separation units, tanks, injection pumps and so on will have more emissions and more leaks than a site with lower equipment counts. The average number of failures or leaks per equipment type may be predicted from a maintenance report, and the combined number of failures or leaks per year for a site may be calculated from these equipment failures or leaks or extracted from the maintenance or leaks report data streams. In particular, frequency of monitoring may be set in relation to the frequency of failure or leaks of a certain site. In some cases, the frequency of monitoring may be predicted as lower than the mandated inspection frequency, in which case no additional monitoring may be required. In other cases, the frequency of monitoring needed may be higher than the mandated inspection frequency in which case additional monitoring may be prescribed. The schedule of that additional monitoring may be selected to minimize the uncertainty associated with the state of the equipment from the site. For instance, for a site mandated to be monitored once a year, it may be necessary to add the additional monitoring step at the six-month mark such that monitoring inspections are equally spaced in time. This scheduling may be influenced by other factors such as seasonality, operational state of the site, density of neighboring site or other factors. For instance, monitoring for butane gas leaks in Alberta during wintertime may not be sensible because butane does not vaporize at low temperatures. Another factor of interest is the intensity of the leaks. Scientific literature suggests that the emission of typical airborne compounds of interest (e.g., methane or other compound) can generally follow the rule, meaning that 20% of the largest leaks emit 80% of the compound. This means that this larger type of leak, while less common, emits more than an average-sized leak. Other rules can be determined and used. Identifying the sites or equipment with the highest probability of large leaks can inform the order or priority of inspection, maintenance, etc. A third factor of interest is the intermittency of leaks. Some leaks are intermittent at a certain frequency, and this informs the frequency at which the measurement needs to be performed. A fourth factor is the response time of the operator. Indeed, certain sites are inaccessible, and the operator may not be able to respond rapidly to a leak, in which case the rapidity of measurement may matter less than the certainty of it. A fifth factor is the possibility of overlapping inspection methodologies. For example, one may use satellites at the field level to inform of leaks sufficiently large to be detectable from space, which may dynamically trigger inspection visits to target sites, reducing the cost of monitoring a large area. A sixth factor is the proximity of various sites. Indeed, sites sufficiently close together may be inspected by a single static monitor, therefore amortizing the instrument cost over multiple sites.

Leaks are not the only type of emission that may be observed, identified, and/or analyzed at a site. A large fraction of emissions can result primarily from the activity or from the operation of the equipment. If the total emission is of importance from an inspection standpoint, real-time (continued or periodic) or frequent inspection methods may be of interest.

Externalities such as weather and remoteness of the site may influence the best method to be used. High cloud cover can for instance block observation from space and harsh weather conditions and low communication infrastructure can influence the cost of deployed sensors.

The return on investment for a certain inspection method may reduce with frequency: once initial leaks are repaired, a long period of time may elapse before new leaks occur, meaning that the probability of leaks is dependent on the history of the site and may widely vary. Thus, the use of datastream and statistical inference of the conditional probabilities of leaks is tremendous for the prediction of potential leaks and appropriate inspection schedules and methods. The proposed method weights these various factors to select the most appropriate inspection embodiment.

The advantage of each inspection method is described herein. Static monitoring through a single sensor or through a network of sensors may provide high-frequency measurements, with tailored detection thresholds based on the distance of the sensor to the potential source, and address at least equipment identification, as presented in the disclosure. Because the sensor is static, the cost of the inspection is determined by the number of potential leak points observable in the detection area, site size, and the cost of ownership of the sensor system, which may be higher than a mobile solution on a per-year basis. The advantage of a mobile solution could be the possibility of amortizing the measurement price on a larger number of potential sources to the cost of lower frequency and/or lower detection limit. For instance, drones may be used once per quarter and have a low detection limit, while satellites may have a 24-days frequency and cover large swaths of land but only detect the largest leaks. Monitoring by plane falls in between the satellite and the drone, and thus could offer a balance of price, inspection frequency, and detection limit. Manual site inspections or operator-based inspections are driven by the cost of labor and a variable measurement quality depending on operator competency, but these inspections can generally pinpoint the leak location and partially assess their size. Similarly, a larger firm could amortize labor costs across many sites, whereas smaller firms may pay more in labor costs per site.

In certain embodiments, methods can identify the best method or methods for site inspection at a given time by calculating the advantages and disadvantages as a function of the expected site emissions volume and frequency and the externalities associated with the measurements in order to maximize a measured emission volume while minimizing the cost. The higher volume of measured emission may then be used to provide a higher volume of reduced emissions.

One embodiment of the technology involves using monitoring information and data streams to enhance product recovery and emission reduction and to generate income by emissions reduction credits, such as carbon credits or added value at the sale of the product via product labeling or certification. For example, this technology could be employed to certify low-emission natural gas or biogas, or some other certification or labeling of interest, in the case that the measured compound is a greenhouse gas, valuable gas, or commoditized product.

Indeed, the detection of greenhouse gases emitted during operations may be used as a quantification of carbon-equivalent intensity. In general, carbon credits in a cap and trade market may be allocated based on the carbon emission offset compared to competitors for a certain product intensity. For example, a certain number of carbon allocations may be provided for a certain number of MMBtu produced in a gas field. An operator that emits fewer greenhouse gases and can demonstrate that fact through emissions quantification may demonstrate emitting less per MMBtu produced, and thereby earning carbon credits which may be sold on the carbon market for a profit. In another embodiment, in the case of an open carbon market, the measurement of carbon equivalent emissions through the use of the method proposed herein may be presented as a carbon offset method directly by quantifying the amount of carbon equivalent reduced through the application of the method and may be sold as such. For instance, the use of a static sensor may lead to the reduction of methane emissions that if related to the cost of operation of the sensor, may lead to a significantly lower cost per carbon ton equivalent than the spot price. The reduction of the carbon footprint may be evaluated, and the difference may be sold as a carbon offset on the carbon market.

The other path to revenue that commoditizes emission monitoring and reduction resides in the certification of the product being produced by the monitored equipment. Indeed, the environmental impact of the condition in which the product is produced may impact the certification of the product to certain standards, which in turn can be sold at a higher price than a product that does not meet the standard. For example, the emissions due to the production of natural gas may reach levels that make the greenhouse gas impact of natural gas on par with burning coal, negating its value proposition of being a more environmentally friendly fuel. Some certified natural gas products attain a price that is up to 1% to 10% higher than the non-certified commodity. The monitoring of emissions and reduction of emission disclosed herein can help producers meet the strict rules and burden of proof associated with certification.

In all or some embodiments, the method can include the quantification of emissions and emission offsets obtained by a hybrid/dynamic inspection, preventative maintenance, and operational optimization for the generation of low emission certified products, carbon offsets, or the reduction of carbon credit consumption through emissions reductions and total emission reporting.

The construction and arrangement of the elements of the systems and methods as shown in the embodiments are illustrative only. Although a number of embodiments of the present disclosure have been described in detail, those skilled in the art who review this disclosure will readily appreciate that many modifications are possible (e.g., variations in number of sensors, sensor position, removal and addition of sensors, weather detection elements, etc.) without materially departing from the novel teachings and advantages of the subject matter recited. For example, elements shown as integrally formed may be constructed of multiple parts or elements. Any embodiment or design described herein is not necessarily to be construed as beneficial or advantageous over other embodiments or designs. Accordingly, all such modifications are intended to be included within the scope of the present disclosure. The order or sequence of any process or method steps, including the steps discussed in connection with the algorithms discussed herein may be varied or re-sequenced according to alternative embodiments. Other substitutions, modifications, changes, and omissions may be made in the design, operating conditions, and arrangement of the embodiments without departing from scope of the present disclosure or from the spirit of the appended claims. For example, the techniques disclosed herein can be used to monitor other locations, including inside factories, warehouses, shipping centers, homes, apartments, or the like.

The present disclosure contemplates systems and methods which may be implemented or controlled by one or more controllers to perform the actions as described in the disclosure. For example, in some embodiments, the controller, whether part of a sensor, computing device, etc., may be configured to process data from sensors, users, or operators and model, calculate, and perform one or more simulations within different data sets, tables or maps described, perform any or all described algorithms and any others similarly suitable, and control operation of any disclosed parts or components in a manner necessary or appropriate for proper function, operation, and/or performance of any disclosed systems or methods.

1—Gaussian Plume Model: An aspect of the system may use a reduced order model rather than a full dispersion advection transport model for the simulation of transport of the trace gas of interest. In particular, Gaussian Plume modeling may be used. The Gaussian plume model uses a gaussian approximation of the plume geometry to approximate dispersion. This model assumes a flat terrain and a well-mixed dispersion process. The gaussian Plume is a reduction of a steady state solution of the flow equations in this simple geometry of the terrain. Therefore, only a few parameters are sufficient to describe the model, such as: the source to sensor distance and direction, the wind direction, the height of the source and the height of the sensor. Internal parameters include the dispersion width in the horizontal and vertical directions through the intermediary of the standard deviation of the gaussian shape. A simple reduction consists in taking an identical standard deviation for both vertical and horizontal terms. Some approximation of the dispersion width can be obtained using Pasquill curves which may depend on the atmospheric stability class at the time of transport and distance between source and sensor. One configuration of the present disclosure is directly estimating the stability class and or the dispersion standard deviation using the measured standard deviation of the wind at the sensor location on a time scale that is corresponding to the time of transport from the sensor to the source. This standard deviation is calculated over many samples using the wind direction change during a period of interest, for example using 1 sample per second over a period of a minute to calculate the wind standard deviation. It is then possible to use the horizontal wind standard deviation to calculate the stability class and then use this to calculate the dispersion standard deviation. Alternatively, the standard deviation of horizontal wind can be used to directly approximate the plume dispersion width.

When the internal dispersion terms are obtained, the other inputs such as concentration at the sensor, position of source and sensor and average direction of wind during the observation period can be used to solve the gaussian plume equation. Note that the direct gaussian plume equation relates flux at the source to a concentration at a selected point. The inverse gaussian plume equation permits to relate the concentration at a point to the flux at the evaluated source. Because the position of source and measurements at the site setup can be determined, and wind speed, wind direction and concentration may have been measured continuously, the flux of a source by using the inverse gaussian equation may be estimated.

The gaussian plume model and its inverse model can be used in the methods described in FIGS. 12 and 13 as an alternative to the more complete dispersion advection transport model as a lower computational cost alternative. This is to the cost of ignoring the effects of topology and obstacles that are considered in the dispersion advection transport model.

Quantification Algorithm: A quantification algorithm may be used to quantify and detect leaks from the use of continuously monitored concentration and wind data. There are four major steps in the road map of this algorithm: localization, event detection, background calculation, and atmospheric stability. The localization uses the location of the sources and detectors to calculate the probability of a detector seeing an event or leak from each sensor. Emission plumes, for example methane plumes of equivalent size are compared along with the peak events at each sensor. The most probable source will be identified, and the source will collapse if there is no event identified. The probabilities from each detector then provide a weighted average of the flux rate at each source.

During event detection, the methane plumes "seen" by the detectors are individually isolated, so that each event can be identified. The background calculation involves estimating the background concentration for each detector when no event is detected. The background concentration is used as a baseline to determine the significance of an event when there is a spike in methane readings. In the last step, the atmospheric stability is predicted from wind speed and direction to account for spreading of the plume.

Localization and Atmospheric Stability: The Gaussian plume model is the foundation of the quantification algorithm and attributable to some of the major assumptions during modeling, e.g., multivariate normal distribution of concentration and radial basis coordinate system. The effects of wind speed and direction, mixing, and atmospheric stability are accounted for in the Gaussian plume model.

Figure 17:
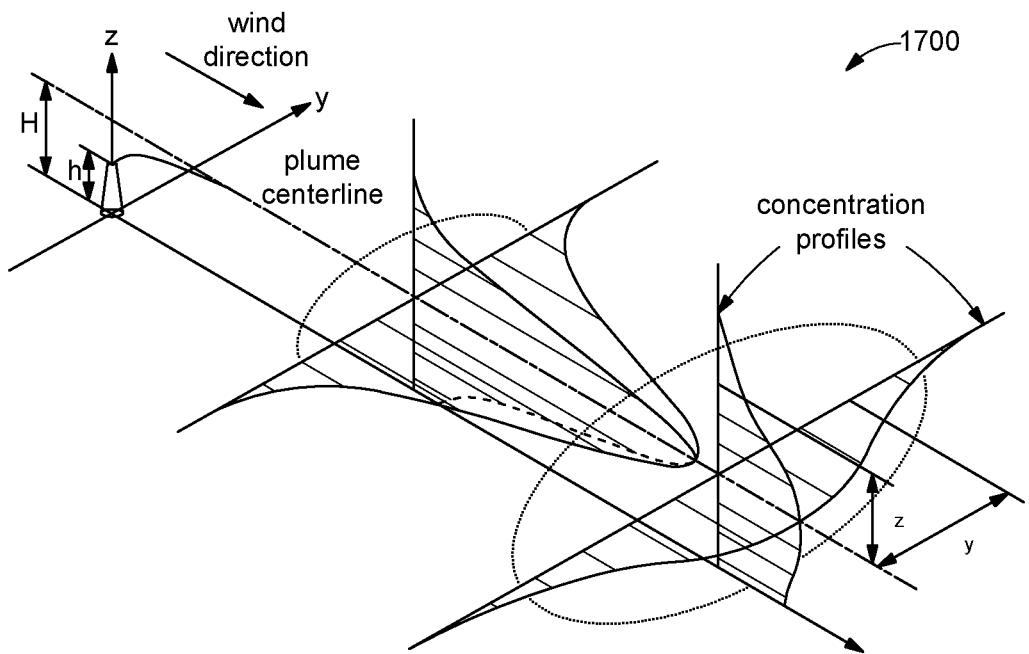
FIG. 17 illustrates an example Gaussian plume model that includes a plume modeled as radially extending with horizontal and vertical spreading, in accordance with an illustrative configuration of the present disclosure.

With reference to FIG. 17, a representation 1700 of a Gaussian plume model (adapted from J.M. Stockie (2011)) is illustrated. As shown in the FIG. 17, a plume (for example, of methane gas) is modeled as radially extending with horizontal and vertical spreading. For an emission rate Q g/s and wind velocity of u m/s, the concentration distribution profile is known as the Gaussian plume solution for some sensor height of z meters and source height of H meters, as provided in the below equations:

$$C(r, y, z) = \frac{Q}{4\pi u r}\exp\left(-\frac{y^2}{4r}\right)\left(\exp\left(-\frac{(z-H)^2}{4r}\right) + \exp\left(-\frac{(z+H)^2}{4r}\right)\right) \quad (2.1)$$

$$r = \frac{1}{2}\sigma^2(x) \quad (2.2)$$

$$\sigma^2(x) = ax^b \quad (2.3)$$

$$x = R\cos(\theta - \theta_0), \quad y = R\sin(\theta - \theta_0) \quad (2.4)$$

In the equation (2.1), the first term $Q/4\pi u r$ is the initial condition or initial flux; and the second term $\exp(-y^2/4r)$ is the spreading of the plume off the y-axis. The third and fourth terms $\exp-(z-H)^2 + \exp-(z+H)^2/4r4r$ are the change in the plume as a function of height. The parameter a is the standard deviation of the concentration distribution and r represents its variability; y, z are the Cartesian coordinates; a, b are the diffusion parameters related to the atmospheric stability class. Depending on the hour of the day, a relationship between the time of day, Pasquill-Gifford stability class, and the diffusion parameters can be determined. In the equation (2.1), the concentration distribution profile is projected to radial basis coordinates.

A function T dependent on wind direction may be defined using equation below:

$$T_1 = \frac{1}{2\pi u (aR^b)^2}, \quad (2.5)$$

$$T_2 = \exp\left(-\frac{R^2\sin^2\left(\frac{\pi(\theta-\theta_0)}{180}\right)}{2(aR^b)^2}\right), \quad (2.6)$$

$$T_3 = \exp\left(-\frac{(z-H)^2}{2(aR^b)^2}\right), \quad (2.7)$$

$$T_4 = \exp\left(-\frac{(z+H)^2}{2(aR^b)^2}\right) \quad (2.8)$$

Figure 18:
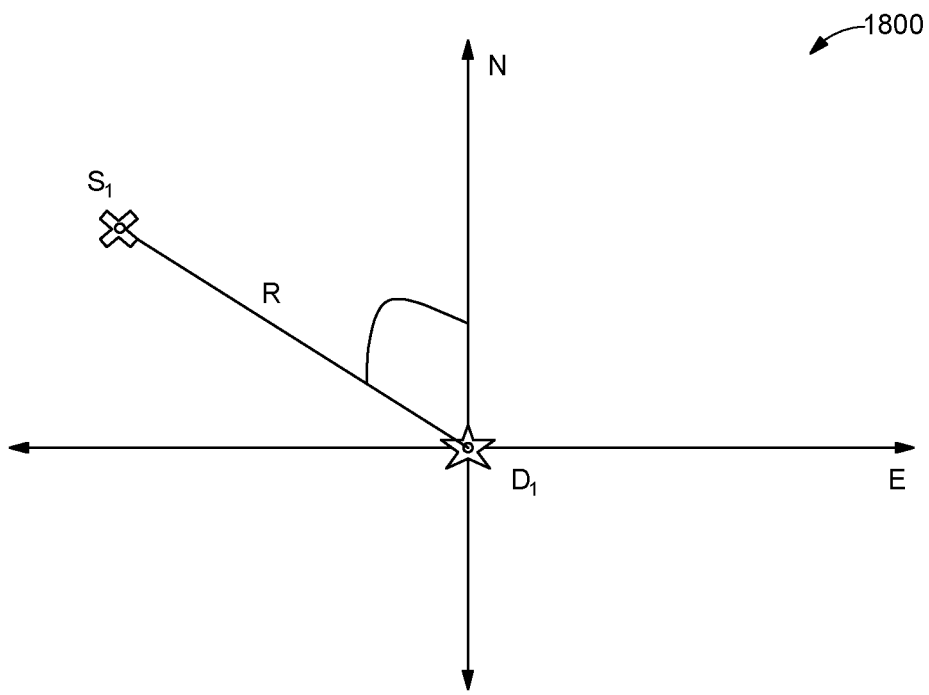
FIG. 18 illustrates a graphical representation illustrating radial distance and angle between a source and a detector, in accordance with an illustrative configuration of the present disclosure.

During localization, there is a probability pn,m that a detector n=1, 2, ..., N can "see" a source m=1, 2, ... M at a given time as a function of wind speed and direction. The angle $\theta_0$ and radial distance R between the source and detector is first measured and then the flux from source m is computed using concentration data from detector n. FIG. 18 is a graphical representation 1800 illustrating radial distance and angle between source S1 and detector D1. The conditional probability is then given by (2.9)

$$P(S_m|D_n, t_k) = pn, m, n=1, 2, \ldots, N, m=1, 2, \ldots M, k=1, 2, \ldots J, \quad (2.9)$$

The probability P(Sm|Dn,tk) in (2.9) is the probability source m emits given readings from detector n. Essentially, it is the probability of seeing a leak at the source. The probability curves are given for all possible paths of the Gaussian plume in radial coordinates. The input parameter $\theta_0^{n,m}$ is the angle between the specific source m and detector n. The function T is dependent on wind direction, such that $$T(\theta_j^{n,m}) = \frac{T_1 \times T_2(\theta_j^{n,m}) \times (T_3 + T_4)}{\rho_{gas}}, j = 1, 2, \ldots, J, \quad (2.10)$$

$$\theta^{n,m} = (-89 + \theta_0^{n,m}, 89 + \theta_0^{n,m}), m = 1, 2 \ldots, M, n = 1, 2, \ldots, N, \quad (2.11)$$

In addition, the condition is set that if $\theta_j^{n,m} > 360$, j=1, 2, ..., J, then $\theta_j^{n,m} \rightarrow 360 - \theta_j^{n,m}$. The constant $6.56 \times 10^{-4}$ is for the conversion of units between parts per million volume and g/m³.

The next step is to normalize (2.10) at time $t_k$, k=1, 2, ..., J given some wind direction $\theta_k^{n,m}$ and wind speed $u_k$. The sum of probabilities for the sources $S_m$ and the residual probability or background B is 1, where, $$P(S_m|D_n, t_k) = \left(\hat{T}(\theta_1^{n,m}), \ldots, \hat{T}(\theta_J^{n,m})\right), \text{ at time } t_k \text{ for } k = 1, \quad (2.12)$$
$$2, \ldots, J; m = 1, 2, \ldots, M, n = 1, 2, \ldots, N,$$

$$P(B|D_n, t_k) = 1 - \sum_{m=1}^{M} P(S_m|D_n, t_k), \quad (2.13)$$

$$\hat{T}(\theta_i^{n,m}) = \frac{T(\theta_i^{n,m})}{\sum_{j=1}^{J} T(\theta_j^{n,m})}, i = 1, 2, \ldots, J. \quad (2.14)$$

Figure 19:
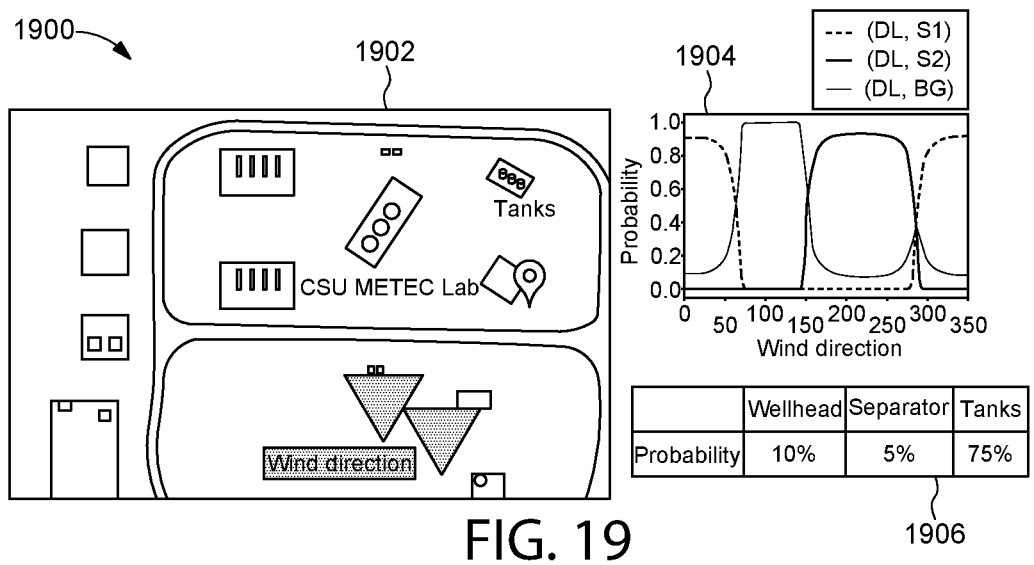
FIG. 19 illustrates an example of analysis performing localization of a site (e.g., Colorado State University's METEC Lab experimental site) with the probability curves given as a function of wind direction, in accordance with an illustrative configuration of the present disclosure.

FIG. 19 shows a schematic representation 1900 an example of analysis performing localization of a site 1902 (e.g., Colorado State University's METEC Lab experimental site) with the probability curves 1904 given as a function of wind direction and graph 1906.

The associated functions for localization and atmospheric stability may be the following: radial gaussian, flux, return BNL dispersion coefficients, compute geometry, site probability.

The next phase of the quantification algorithm is to detect events from each set of concentration data corresponding to its respective detector. A preliminary analysis was developed to look at 3-minute intervals of 1-minute data to see if there is a peak in concentration during this period of time. The peak in concentration is analyzed by using the difference formula to approximate the gradient or slope of the concentration curve. If it exceeds a threshold of 0.75, then the time period is classified as an "event" with a nonzero flux rate; otherwise, it is classified as "no event" with a negligible flux rate. The start and end time of the event must also be specified. The event is said to start if the change in concentration is greater than some δt, and the event ends when it is less than −δt. In this way, the event is assumed to be like a symmetric curve with about the same slope for the start and ending of the event.

Figure 20A:
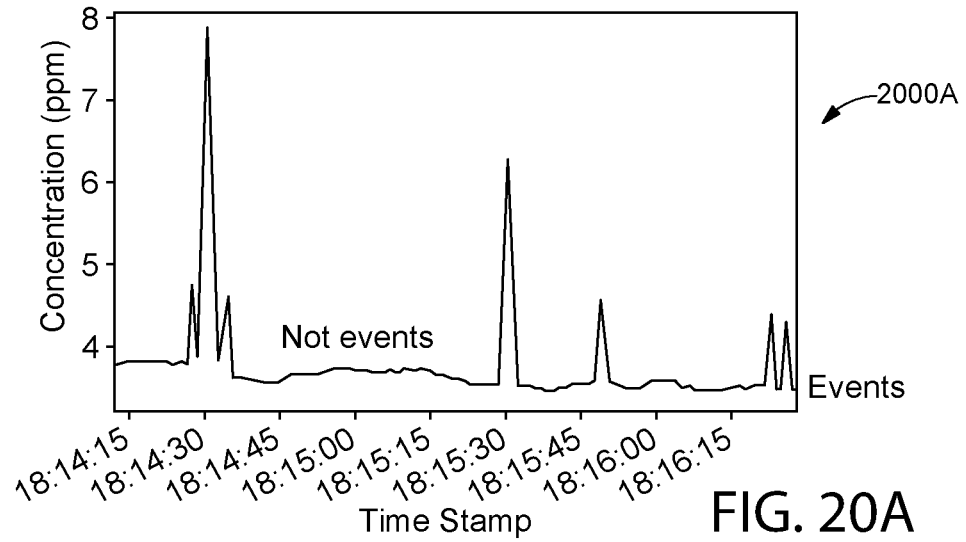
FIGS. 20A-20B illustrate graphical representations illustrating example of five events detected along with background concentration, in accordance with an illustrative configuration of the present disclosure.
Figure 20B:
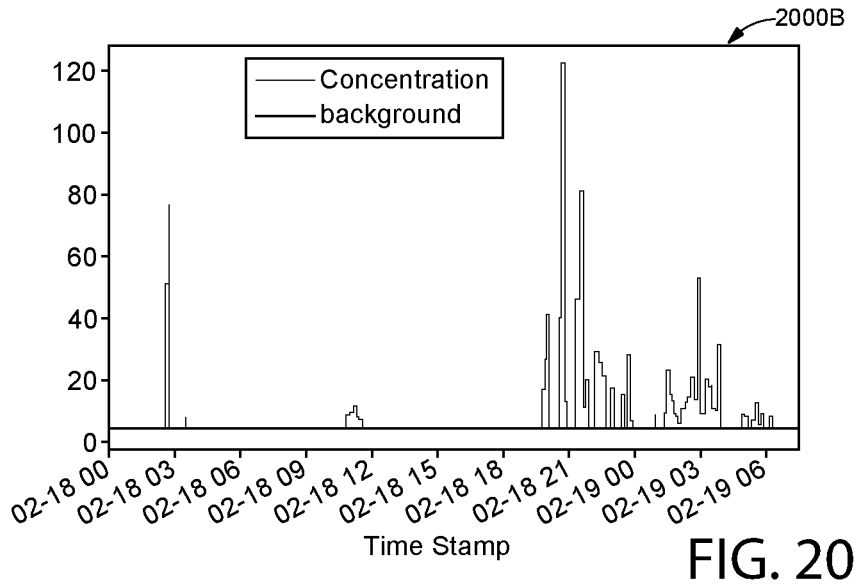

The baseline concentration must first be specified as a continuous line. To do so, the background concentration is calculated using the data corresponding to wind direction between ±25 degrees from θ0. Outside of the events, the data is removed 15 minutes before and after an event from the background concentration. Then, a continuous 5-minute rolling average is taken over designated background concentration. If there is no concentration data moving forward, the backward fill is applied to populate missing values forward in time; and the forward fill is applied to propagate the last observation forward. Then, the wind speed was filtered, so that it cannot drop below 0.5 m/s and exceed 10 m/s. FIGS. 20A and 20B highlights an example of five events detected along with the background concentration.

With reference to FIGS. 20A and 20B, graphical representations 2000A, 2000B of results from (a) event detection and (b) background concentration are depicted. The associated functions for event detection and background calculation may be the following: quantify_and_detect_leaks, and quantify.

In some configurations, total hourly flow rate may be determined using either (i) maximum probability based method or the (ii) total weighted average method. For method (i) in (4.1), the total hourly flow rate is displayed as the average of hourly sensor based flow rate for the most probable source. This average is restricted to sensors with conditional probabilities higher than 75% or attributable to the sensor with the highest probability reading sensor if no other sensors have a probability reading higher than 75%. This method works best if only one source is active and the rest are inactive with negligible or no emissions. The maximum and minimum flow rates at each sensor are provided if it has a specific flow rate over 75%. For method (ii) in (4.2), the flow rate of each source is the weighted average as the average of all partial flow rates of the sensors weighted by the hourly conditional probabilities for each sensor with probabilities higher than 100/M (100 per million). The flow rate for all sources is then summed to form a total flow rate for sources that have a total probability of leak over 100/M. This method is more efficient at accounting for multiple sources but less so for a single emitting source.

$$\text{Method}(i): \hat{Q}_m = Q_m(P_{>0.75}(S_m|t_{60})), m = 1, 2, \ldots, M, \quad (4.1)$$

$$\text{Method}(ii): \hat{Q} = \sum_{m=1}^{M} P_{>\frac{100}{M}}(S_m|t_{60}) Q_m, \quad (4.2)$$

$$P(S_m|t_{60}) = \frac{\sum_{n=1}^{N} C(D_n, T) P(S_m|D_n, T)}{\sum_{n=1}^{N} C(D_n, T)} \quad (4.3)$$

In one alternative configuration, an air quality measurement system may include computer-enabled instructions outlined as followed:
1. Connect to Amazon Web Services API using your designated username and password
2. Connect to a Dashboard and pull site data for a given period of time and site ID
   (a) Detector locations and resampling for 1-minute data
   (b) Equipment/source geometry
3. Compute the methane concentration curve for a source S in radial coordinates centered at S over the vector of wind directions $\theta \in (-89+\theta0, 89+\theta0)$
4. Define the diffusion parameters a, b
   (a) Create a dictionary with values of the diffusion parameters a, b from the Gaussian plume model given the Pasquill-Gifford (PG) atmospheric stability class
   (b) Associate the PG class to the time of day and then go into dictionary to select appropriate values of a, b
5. Create polygon geometry around sensors and detectors
   (a) Create polygon objects in a polygon dictionary from the equipment geometry
   (b) Calculate the centroids and (backward and forward) azimuth angles of the polygon equipment and sensors
   (c) Then, calculate the distance between the centroids of the polygon equipment and sensors
   (d) Calculate the average background angle
6. Create the normalized probability curves that one detector sees a source
7. Quantify and detect leaks by isolating plumes seen by detectors in time series concentration data
   (a) Isolate detector concentration and look at fixed intervals to see if an event occurs during this period of time
   (b) Classify whether there is an "event"
   (c) Find baseline concentration from background 8. Run all of the functions in the final function that calls them all in quantify The instructions provided immediately above for an illustrative air quality monitor may be configured to provide functions as follows: Import site data over a specified time period: pull site data(siteId,startDate,endDate)
Inputs:
  siteId—identification number associated with site;
  startDate, endDate—time frame over which to import site data
Outputs:
  site df, i.e, data frame of detector and equipment locations, detector time series data; and
Compute the methane probability curve for a source S in radial coordinates centered at S over the wind directions $\theta \in (-89+\theta_0, 89+\theta_0)$ using Equation (2.1): radial gaussian (u,R,theta_$\theta$,z,H,a,b)
Inputs:
  u—wind speed in units of m/s
  R—radial distance between detector and sensor in units of meters
  Theta_0—angle between detector and sensor
  z—height of detector(s) in units of meters
  H—height of source(s) in units of meters
  a,b—diffusion parameters dependent on atmospheric stability
Outputs:
  returned vector, i.e., concentration distribution curve
Convert from concentration to flux: flux(c ppm,background,windspeed,sigma y,z,H)
Inputs:
  c ppm—concentration of methane in units of ppm
    background—background methane concentration in units of ppm
    windspeed—wind speed in units of m/s
    sigma y—horizontal dispersion coefficient in m
    z—height of detector(s) in units of meters
    H—height of source(s) in units of meters
Outputs:
  flux gs, i.e., methane flux rate in units of g/m$^3$
Finding the appropriate values of the diffusion parameters a, b from the Gaussian plume model given the time of day and Pasquill-Gifford (PG) atmospheric stability class: return_BNL_dispersion coefficients(hours)
Inputs:
  hours—vector of hours over which data is being recorded and read-in
Outputs:
  a arr, b arr, i.e., vector of diffusion parameters over time period of measured data Creating a dictionary with values of the diffusion parameters a, b given the PG class: BNL dict
Store polygon objects from the equipment geometry and sensors in a polygon dictionary; calculate the centroids of the polygon equipment and sensors, and then calculate the distance between the centroids of the polygon equipment and sensors R and azimuth angle $\theta_0$ (for background too): compute geometry(equipment geometry,sensor locations)
Inputs:
  equipment geometry—contains the location and information about the sources/equipment
  sensor locations—contains the locations and information about the sensors
Outputs:
  geom dict, e.g., R, $\theta_0$
Compute the normalized probability curves that one detector sees a source: site probability(geom dict,detectors,sources)
Inputs:
  geom dict—output from the function compute geometry; it is a dictionary containing the azimuth angles, radial distance, centroids, etc. of the sources and detectors
  detectors—contains the locations and information about the sensors
  sources—contains the location and information about the sources/equipment
Outputs:
  probability df, i.e., probability concentration curve of seeing an event or no event at detector
    See the upper right-hand corner of FIG. 18 for an example output.
Quantify and detect leaks by isolating plumes seen by detectors in time series concentration data: quantify_and_detect_leaks(detectors,sources,site df,geom dict, probability df)
Inputs:
  detectors—contains the locations and information about the sensors
  sources—contains the location and information about the sources/equipment
  site df—output from pull site data; data frame of iterables: methane, wind speed, and wind direction
  geom dict—output from the function compute geometry; it is a dictionary containing the azimuth angles, radial distance, centroids, etc. of the sources and detectors
Outputs:
  events metadata, i.e., whether there was an event; flux df, i.e., data frame of probability of concentration and flux rate
Run all of the preceding codes in one function called quantify(siteId,startDate,endDate)
Inputs:
  siteId—identification number associated with site
  startDate, endDate—time frame over which to import site data METEC Round 2 Testing and Validation Findings and Results of MVP1 Quantification Model: In a field-testing campaign in real world environment at a site (for example, Methane Emissions Technology Evaluation Center (METEC) at Colorado State University), illustrative results from developing, testing, and implementing methods for quantification of methane emissions from oil and gas facilities using sensor nodes and analytics platform are presented. This platform integrates detector data, meteorological conditions, and cloud analytics to detect and quantify methane emissions for remote locations. This first minimum viable product for quantification (MVP1) has, or will be, updated by subsequent tests.

An illustrative installation of the present disclosure performed three days of around the clock live methane emissions tests including daytime, nighttime and in between to investigate the diurnal effect on quantification methods. The design of experiment included a total of forty four test conditions (experiments) where programmed methane releases were introduced from actual natural gas site structure including gas processing units, well heads, and storage tank batteries. A total of eight sensor nodes forming a larger sensor network were deployed at the fence line of the 200 ft×280 ft site with a detector to source distance ranging from 69 to 230 ft. The duration of each test was 60 minutes followed by 15 minutes of no methane release to establish baseline for the next new test and so on. Each test was repeated three times to examine various quantification models for reproducibility of consistent results. Methane release rates ranged from low, 0.05 to high, 0.84 g/s which is a wide range that represents average well pad emissions.

Figure 21:
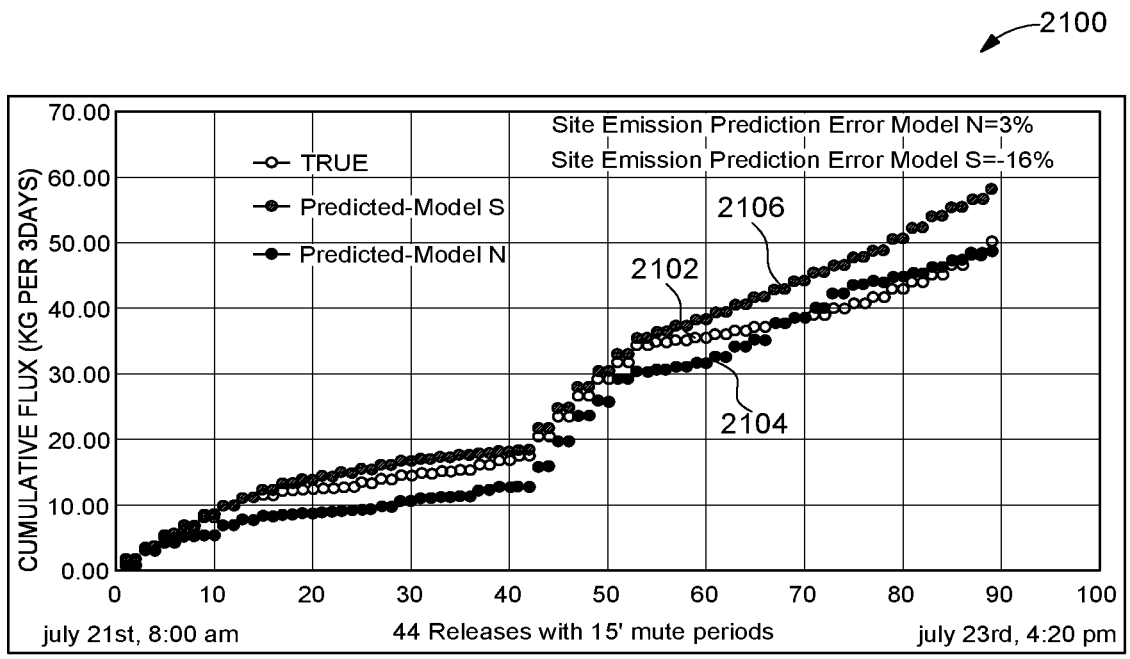
FIG. 21 illustrates a graphical representation of cumulative predictive emissions for a site (METEC Site Emissions) over the course of three days as compared to true emissions, in accordance with an illustrative configuration of the present disclosure.

As part of quantification MVP1, two models (Model N and Model S) for quantification were developed. These models were thoroughly investigated to determine presence of any problem(s) and to employ the best evaluation methods for additional development(s). The quantification methods have demonstrated that it can detect methane leaks in the range of 0.05 g/s up to 0.85 g/s with a total site emission prediction error ranging from −16% to 3% at an average wind speed ranging from 0.5 m/s to 6 m/s at the site footprint and sensor configuration mentioned earlier. Total predicted site emission is the cumulative predicted emission rates of each experiment over the total test period of three days. The True total site emission (cumulative over the full 3-day test period) was 50.22 kg of methane whereas the predicted values were 58.1 kg and 48.74 kg of methane using Model S and Model N respectively. FIG. 21 shows a graphical representation 2100 of the cumulative predictive emissions for the site (METEC site) over the course of three days as compared to true emissions. Further, FIG. 21 shows the METEC R2 comparison of true total site emissions (curve 2102) with predicted total site emissions from model N (curve 2104) and model S (curve 2106) (Cumulative Period of 3 Days—July 21st to Jul. 23, 2021)

Both models were able to predict reasonably well except for few cases where unfavorable wind transport of emissions occurred. Since this continuous monitoring technology relies on wind to advect air borne methane molecules to detector, unfavorable wind conditions could occasionally result in placing the detector upwind of a given emission source, creating a weak signal to noise inhibiting the detector from receiving the right information on emission source concentration. This would impact plume dispersion model ability to predict accurately. Nevertheless, this scenario is not typical for real life deployment as models may be able to use the wealth of wind diversity over time, which was not the case in a limited three-day testing in METEC facility.

Both model N and model S are based on the Gaussian Plume Model (GPM) principles with few different assumptions including smart sampling, weighted average, bootstrapping, radial GPM, cartesian GPM, dispersion coefficients based on Pasquill-Gifford, BNL.

For example, in the site 1902 shown in FIG. 19, detectors and methane release system may be deployed. For example, eight sensor nodes (It should be noted that the term "sensor node" may have been used interchangeably with the term "sensor", or the term "detector", or the term "air quality monitor" or the term "sensing system" in this disclosure) may be set up around the test site (200 ft×280 ft) with a detector to source distance ranging from 69 to 230 ft. This is to reasonably ensure the detectors will activate and capture the gas plume regardless of wind direction, enabling the system to operate autonomously. Wind speed and direction may be measured using ultrasonic wind sensors installed in some of the sensor nodes. The testing may include a release of a controlled methane volume located at three main sources, wellhead, separator, and storage tanks at different release rates ranging from low, 0.05 to high, 0.84 g/s which is a wide range that represents average well pad emissions. The site may have provisions to accurately regulate and measure flow rate using orifice meters, solenoid, and PLC.

Figure 22:
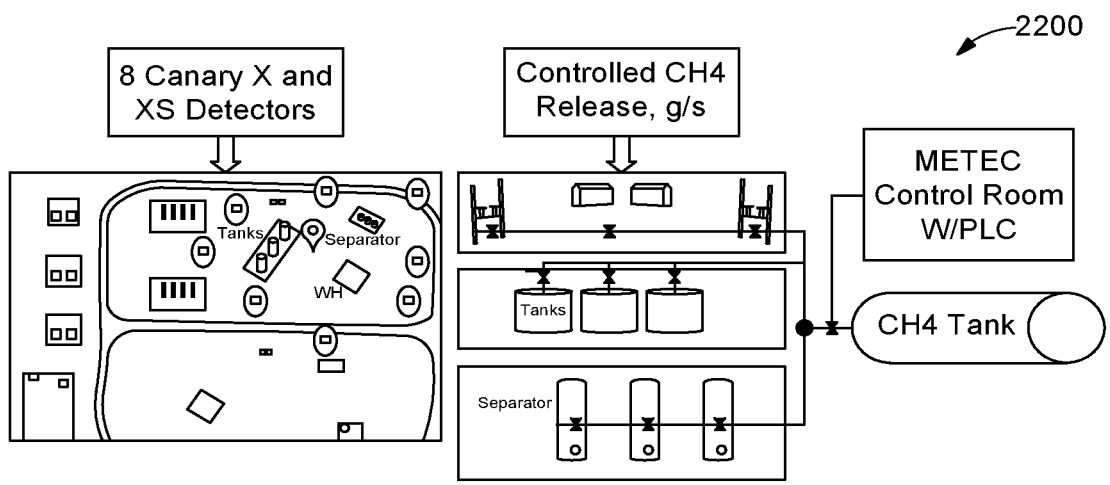
FIG. 22 illustrates a workflow diagram showing a framework of quantification, in accordance with an illustrative configuration of the present disclosure.

FIG. 22 illustrates a workflow diagram 2200 depicting a framework of quantification. As shown in, the quantification workflow diagram of FIG. 22, as field testing progresses, time series data from individual detectors are streamed to Amazon Web Servers (AWS) in real time. The data is comprised of signals from the sensing element as it responds to local methane concentrations, at the location of the detector in addition to wind speed in m/s and wind direction measurements (0o to 360o). Detector data are pushed to AWS for pre-processing before being passed on to the developed model for emission rate and source location prediction. When the data is downloaded into local servers, it is passed on to an extraction, transformation, and loading (ETL) computational pipeline before being ready for the prediction algorithm. The concentration data (ppm) is augmented by GPS coordinates of the individual sensors and a single file encompassing the experimental time of a given test (typically one hour) before being ingested by the model.

Figure 23:
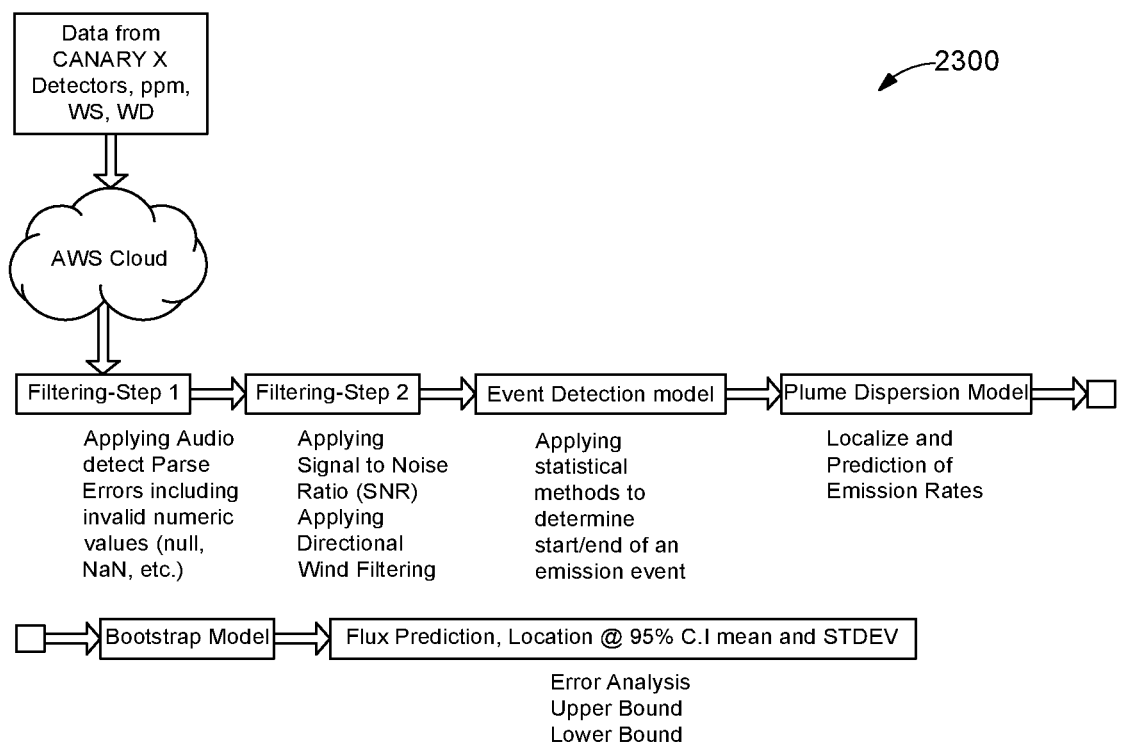
FIG. 23 illustrates a graphical representation depicting a configuration of a dashboard—time-series concentration, in accordance with an illustrative configuration of the present disclosure.
Figure 24:
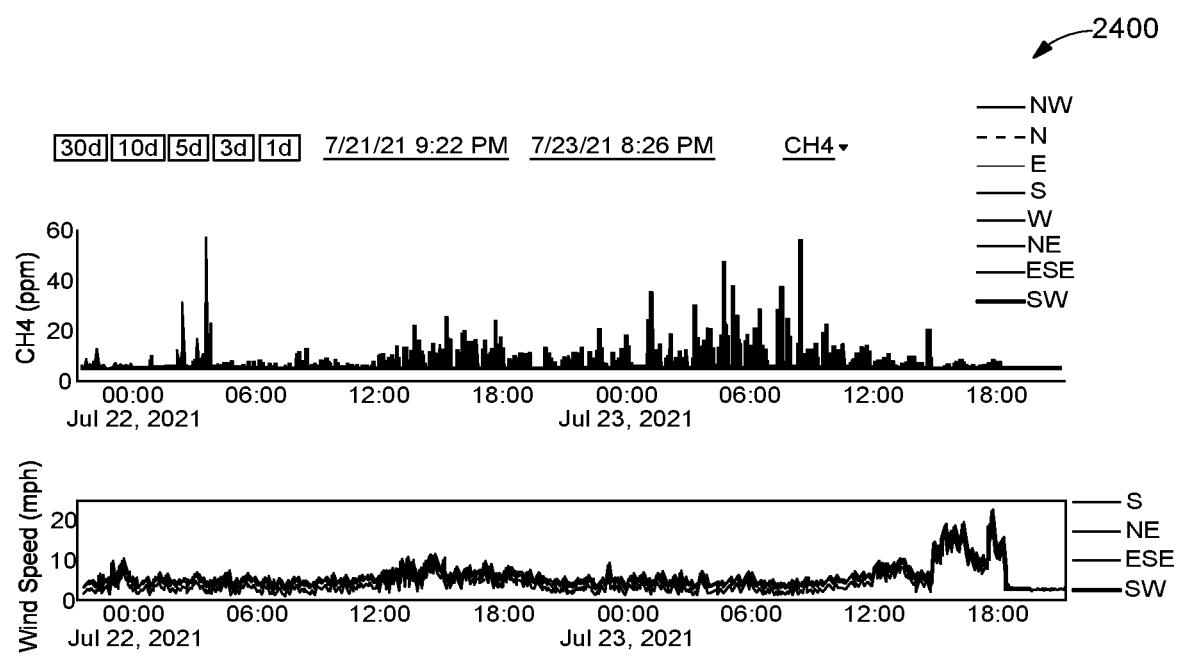
FIG. 24 illustrates an example wind rose diagram defined by a weather data for a site (e.g., METEC site), in accordance with an illustrative configuration of the present disclosure.
Figure 25:
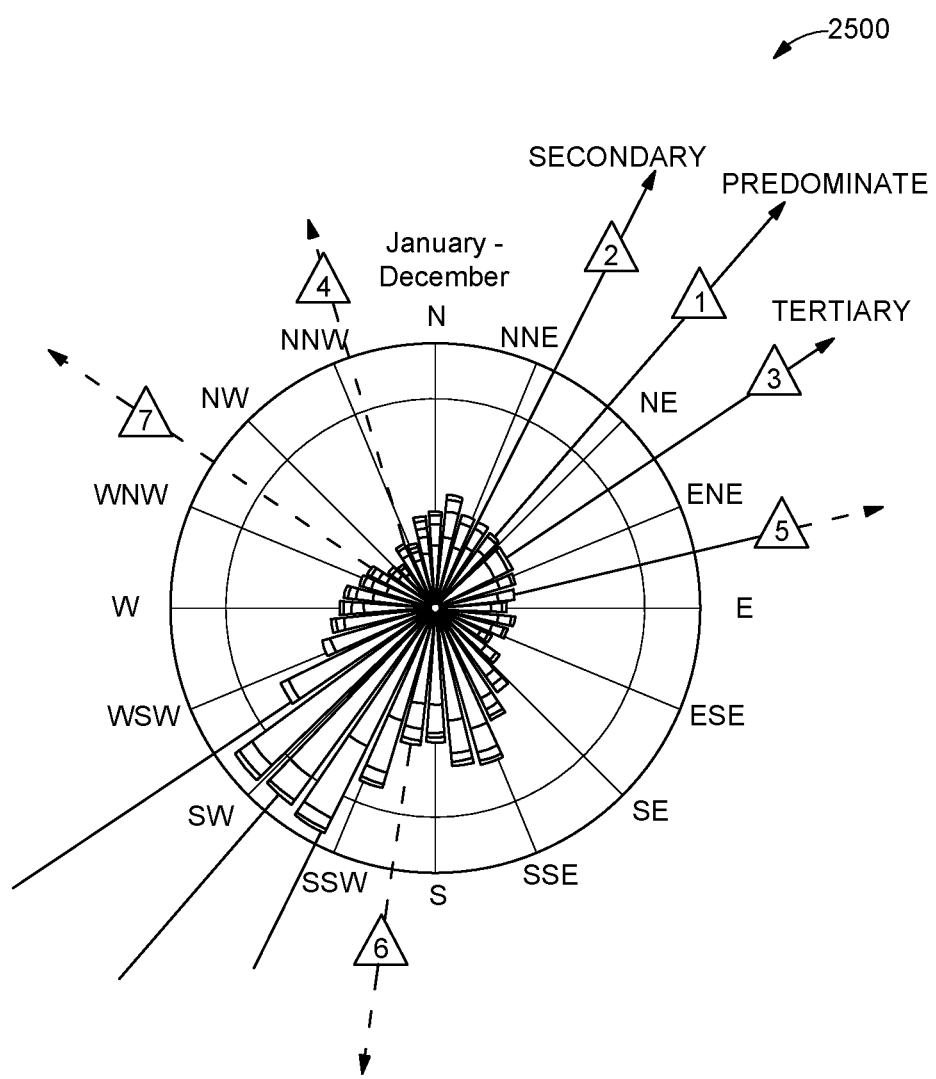
FIG. 25 illustrates another example wind rose diagram including a predominate wind direction, a secondary wind direction, and a tertiary wind direction over a period of time (e.g., a year), in accordance with an illustrative configuration of the present disclosure.
Figures 26A, 26B, 26C:
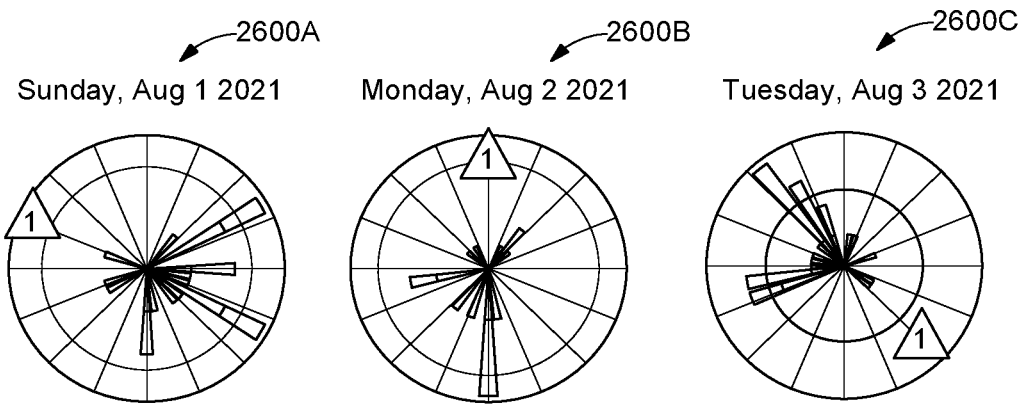
FIGS. 26A-26G illustrate a wind rose diagram for each of a week including a predominate wind direction (shown as "1") during that day, in accordance with an illustrative configuration of the present disclosure.
Figures 26D, 26E, 26F:
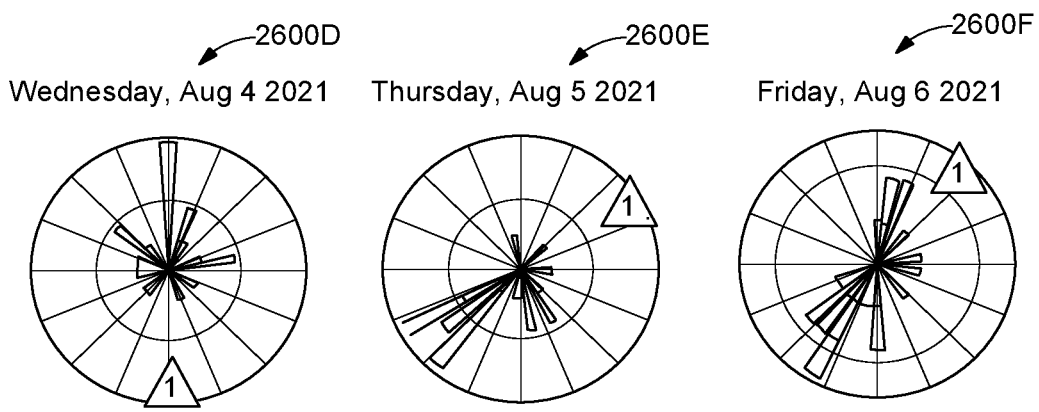
Figure 26G:
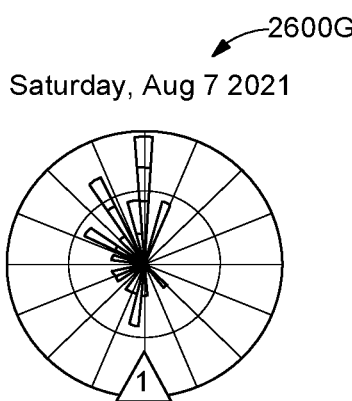

Detector placement is initially decided prior to the testing campaign by studying multiple wind rose diagrams from historical weather stations data and identifying the most likely dominant wind directions around the location of the testing. Visualization of time series and hourly aggregated statistics of concentration, wind speed, and wind direction from all detectors and weather sensors enable the user to assess node engagement and to adjust the experimental setup, if necessary, to maximize alignment of sensors with the dominant methane dispersion directions by the prevailing wind as shown in FIG. 23. FIG. 23 illustrates a graphical representation 2300 of configuration of a dashboard showing time-series concentration. FIG. 24 illustrates an example wind rose diagram 2400 defined by a weather data for a site (e.g. the METEC site). As will be appreciated, wind rose diagrams are graphical charts that characterize the speed and direction of winds at a location. FIG. 25 illustrates another wind rose diagram 2500 including a predominate wind direction (shown as "1"), a secondary wind direction (shown as "2"), and a tertiary wind direction (shown as "3") over a period of time (e.g. a year). FIGS. 26A-26G illustrates a wind rose diagram for each of a week, respectively including a predominate wind direction (shown as "1") during that day. In other words, a wind rose diagram 2600A for Sunday (Aug. 1, 2021), a wind rose diagram 2600B for Monday (Aug. 2, 2021), a wind rose diagram 2600C for Tuesday (Aug. 3, 2021), a wind rose diagram 2600D for Wednesday (Aug. 4, 2021), a wind rose diagram 2600E for Thursday (Aug. 5, 2021), a wind rose diagram 2600F for Friday (Aug. 6, 2021), and a wind rose diagram 2600G for Saturday (Aug. 7, 2021).

Data Pre-Processing: Signal-to-Noise Ratio (SNR): Data pre-processing may be performed on data obtained by detectors running the atmospheric dispersion model. The goal of data pre-processing is to filter out any noisy data before running the atmospheric dispersion model. One data pre-processing method may include analyzing Signal-to-Noise Ratio (SNR).

The idea behind SNR is to see if there is a significant peak in the concentration profile that would indicate that the detector is picking up an unknown or a known leak. The formula for SNR is relatively simple since it involves taking the difference between the highest concentration ($x_{peak}$) and lowest concentration ($x_{base}$) and scaling it by $\frac{1}{\sqrt{x_{peak}}}$.

$$SNR = \frac{x_{peak} - x_{base}}{\sqrt{x_{peak}}}$$

Figure 27:
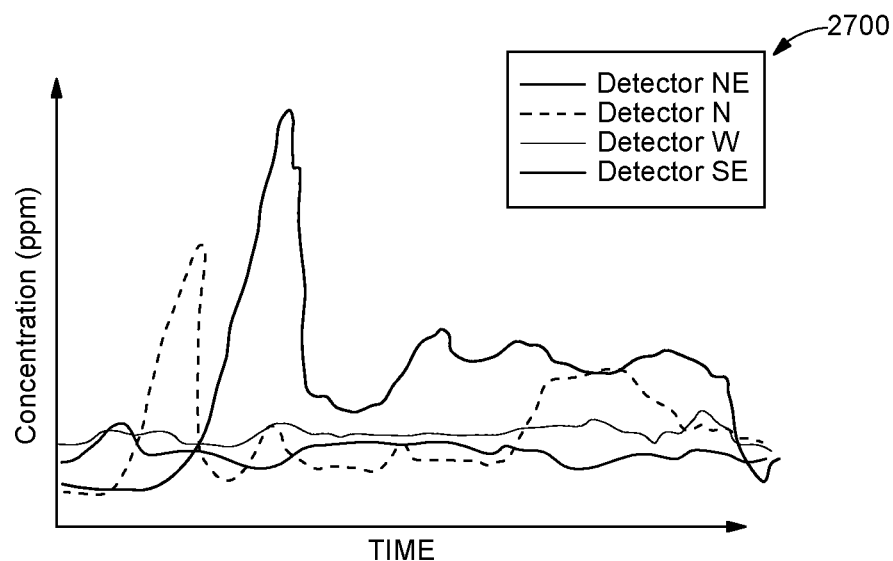
FIG. 27 illustrates a graphical representation of example Signal-To-Noise (SNR) associated with different detectors before elimination of detectors, in accordance with an illustrative configuration of the present disclosure.
Figure 28:
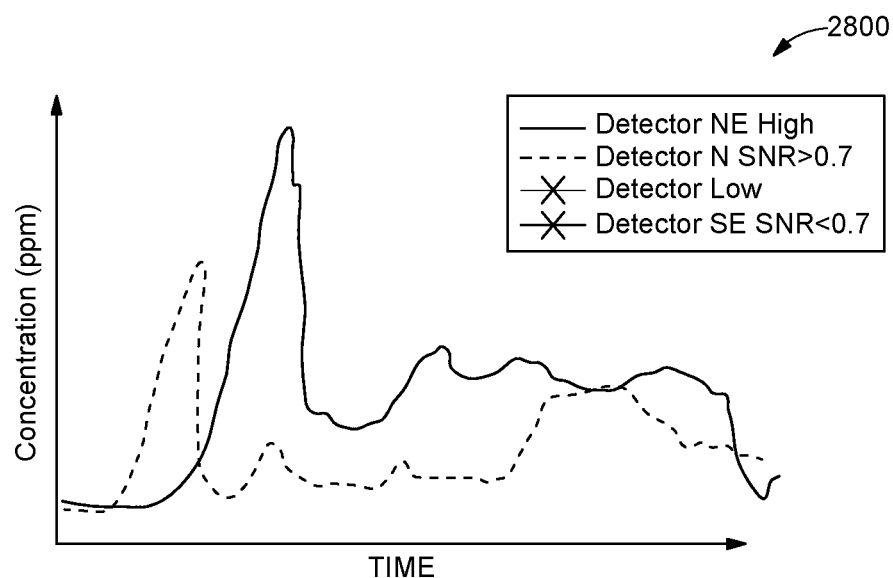
FIG. 28 illustrates a graphical representation of example SNR associated with different detectors after elimination of detectors, in accordance with an illustrative configuration of the present disclosure.

The SNR is performed over each hour, e.g., 8:00 AM-8:59 AM, 9:00-9:59 AM, etc., for each detector. If the SNR ratio is less than 0.7 from 8:00 AM-8:59 AM, the data from this detector is turned off during that hour. Otherwise, the concentration data from the detector is deemed useful to the model, and it is used in the flux calculations of the GPM. Following the example in FIG. 5b, only two of the four detectors are retained while Detectors W and SE are turned off since they have SNR<0.7. In the GPM, the concentration data from Detectors NE and N are the only ones used in the flux calculations. FIG. 27 shows a graphical representation 2700 of an example of SNR associated with different detectors before eliminating two detectors W, SE with SNR<0.7. FIG. 28 shows a graphical representation 2800 of an example of SNR after eliminating the two sensors W, SE.

Figure 29:
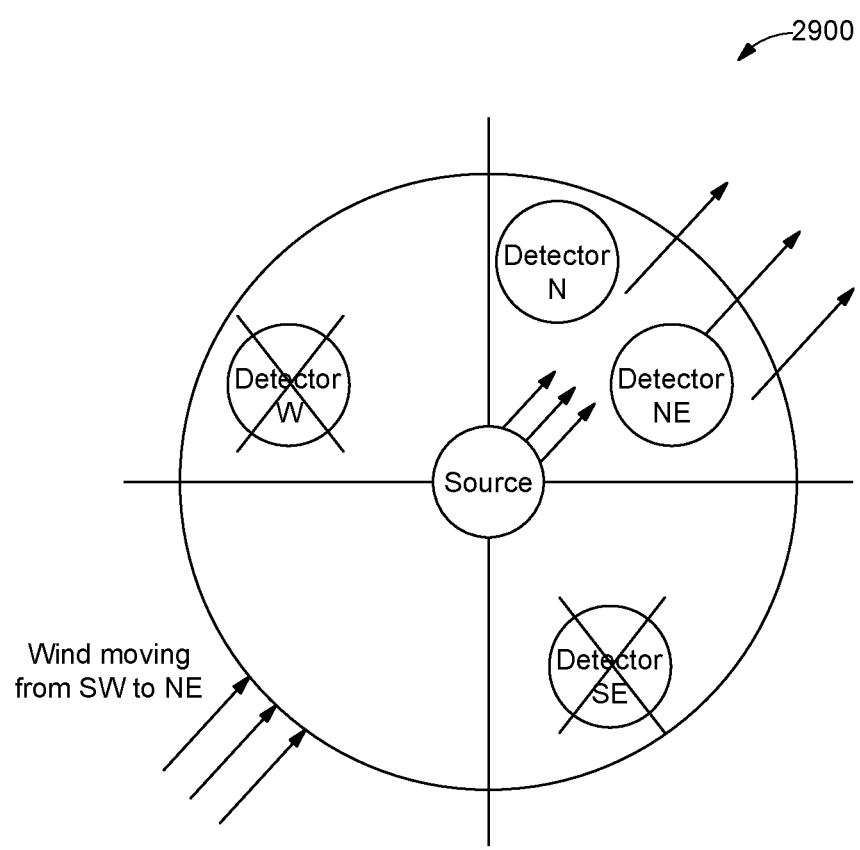
FIG. 29 illustrates a representation of a process wind directional filtering of detectors which are not in the appropriate position of the wind with moderate dispersion, in accordance with an illustrative configuration of the present disclosure.

Wind Directional Filtering: Another method of data pre-processing may be wind directional filtering which may be performed in addition to SNR. Wind filtering is the process of turning off detectors that are outside of the wind direction and focusing on detectors downstream of the emitting source. When detectors are within direction of the wind, they will pick up an emitting source that is carrying a methane plume downstream. If the detectors are not in the appropriate position of the wind with moderate dispersion, then these detectors should be able to pick up the methane plume. Hence, they are turned off. The wind filtering algorithm will turn off detectors that fall out of bounds of the wind direction with the stability class to account for spreading or dispersion of the methane plume from its centerline. FIG. 29 is a graphical representation of an example of wind directional filtering process. As illustrated in the FIG. 29, detectors (i.e., detectors W, SE) which are not in the appropriate position of the wind with moderate dispersion are turned off (i.e., filtered out).

In alternate embodiments, after transmitting the actual emissions measurement to the cloud server, a population of the actual emissions measurement may be filtered, for example, to identify cyclical emissions. The cyclical emissions may be the periodic emissions from the site that may take place as part of the operations at the site, and therefore may not amount to inadvertent leakage. As such, the scope of the disclosure may be restricted to identifying the inadvertent emissions occurring due to leakage, or an accident. It may be noted that the cyclical emissions may be dependent on at least one of the following: a time of day, a day of month, a month of year, temperature, and wind direction.

Plume Dispersion Model for Quantification of Methane Emissions: In a real environment, an industrial plume may propagate and diffuse from the moment an emission is released from a point source as shown in FIG. 17. This transport process is the combination of diffusion (due to turbulent eddy motion) and advection (due to the wind) that defines the term, dispersion (Stockie 2011). The concentration of a contaminant release will be transported through the air in an axisymmetric pattern (idealized case). A method used in modeling this phenomenon may be derived from the advection-diffusion equation and results in decaying Gaussian distribution profiles with distance. A dispersion model is essentially a computational procedure for predicting concentrations downwind of a pollutant source, based on knowledge of the emissions characteristics (stack exit velocity, plume temperature, stack diameter, etc.), terrain (surface roughness, local topography, nearby buildings), and state of the atmosphere (wind speed, stability, mixing height, etc.) (MacDonald 2003).

The complexity of the plume source inversion arises from the need to recover information about the source emission rate(s) and location using concentration signatures from a few detectors. These emissions are related through a highly nonlinear and high-dimensional turbulent dynamic that pervades the near surface atmosphere. A number of analytical and approximate solutions for atmospheric dispersion may be derived under a wide range of assumptions, boundary conditions, and parameter dependencies. One of these solutions is the Gaussian plume solution, which is an approximate solution for single point-source emissions:

$$C(x, y, z) = \frac{Q}{2\pi U \sigma_y \sigma_z} * \exp\left(-\frac{y^2}{2\sigma_y^2}\right) * \left[\exp\left(-\frac{(z-H)^2}{2\sigma_z^2}\right) + \exp\left(-\frac{(z+H)^2}{2\sigma_z^2}\right)\right]$$

Where:
$\sigma_y$=S.D. of horizontal distribution of plume concentration=axb (m)
$\sigma_z$=S.D. of vertical distribution of plume concentration=cxd (m)
C=Concentration at the detector (kg/m3)
H=Effective height of emission source (m)
U=Wind speed along x-axis, assuming invariable with height (m/s)
Z=Detector height above ground (m)

It should be mentioned that as part of this MVP1 two Models (Model N and Model S) based on the GPM principles with few different assumptions. Both the models may be converged to a common algorithm.

Data Post-Processing: The plume model outputs may include predicted release rates (or instantaneous fluxes) at each detector. The predicted release rates from each detector may be grouped together to form a big sample of flux data called the population. After obtaining a full timeseries flux for each detector, bootstrap resampling may be performed to quantify the random errors and provide a confidence range for the statistics reported. The mean flux for each detector may be calculated and added to the population. Further, summary statistics and estimated the precision of the reported statistics may be reported using bootstrap resampling described immediately below.

As it will be appreciated by those skilled in the art, bootstrapping is a statistical procedure involving the generation of random samples with replacement allowing us to quantify the random sampling errors and provide a confidence interval along with all statistics reported. Confidence intervals are estimated computationally.

For example, in a collection of pennies, dimes, and quarters in one bag may be called 'the population' A form of sampling called bootstrapping may be utilized to collect samples from this population to generate basic statistics (e.g., mean, standard deviation, confidence intervals, etc.). For example, an unbiased and a random sample of 5 coins may be collected from the bag of 50 coins. This process is repeated multiple times to determine how much money someone is likely to pull out of the bag with 5 coins on average. There might be a case when someone pulls out $1.25 from 5 quarters and another case when someone pulls out $0.05 from 5 pennies. Extreme cases are identified by repeatedly sampling 5 coins, say 50 times. Sometimes, high, or low amounts are sampled from the bag (e.g., $1.25, and $0.05). They will be accounted for in the confidence intervals as the lower and upper bounds of money collected. The confidence intervals provide us with a form of error statistics, which will be used to assess the variability in the population's distribution.

As will be understood, a confidence interval of [0.05 g/s, 0.10 g/s] for flux is much narrower compared to a confidence interval of [0.05 g/s, 0.35 g/s]. When the confidence interval is narrower, the actual leak rate most likely falls between 0.05-0.10 g/s with less variability in what its actual value. However, when the confidence interval for flux is [0.05 g/s, 0.35 g/s], there is more variability and uncertainty in the actual leak rate. It can fall anywhere between 0.05-0.35 g/s and possibly even outside of these bounds. These confidence intervals, hence, provide us with uncertainty. The formula for the confidence interval is given as follows:

$$95\% \; CI = \mu \pm 1.96 \frac{\sigma}{\sqrt{n}},$$

where μ is the mean flux or release rate, σ is the standard deviation of the population of fluxes, and n is the total number of samples in the population.

Therefore, bootstrapping may be used for summarizing the predicted release rates from each detector and for determining an average release rate that is an unbiased representation of the true leak rate. As such, after transmitting the actual emissions measurement to the cloud server, bootstrapping of the plurality of actual emissions measurement (obtained by the plurality of air quality monitors) may be performed. The average release rate does not depend on any detector with bootstrapping. If one detector overestimates the true leak rate while another detector underestimates the true leak rate, bootstrapping will average over these two cases. The key characteristic of bootstrapping is utilized because the following are unknown: (1) which detector is closest to the source; and (2) which detector is closely estimating the actual leak rate.

Figure 30:
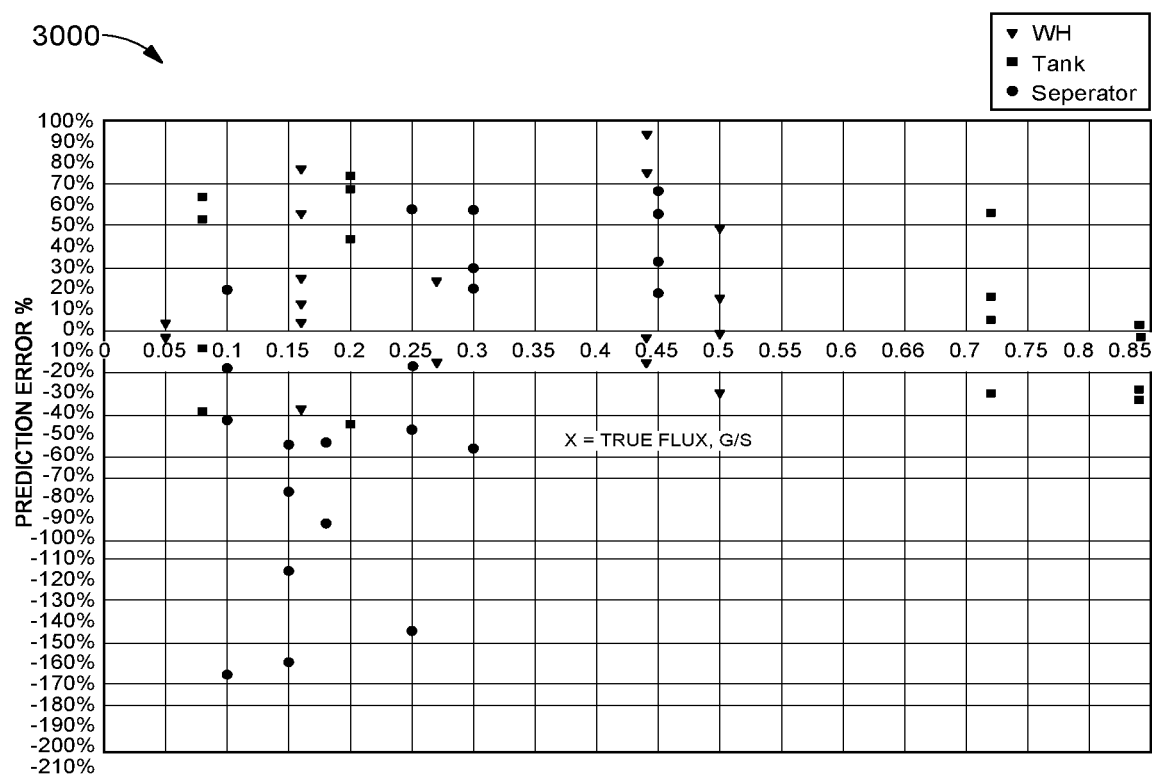
FIG. 30 illustrates a graphical representation of flux predictions for all emission sources based on predictive algorithm for the experiments conducted at a site (e.g., METEC test site) over a cumulative period of three days, in accordance with an illustrative configuration of the present disclosure.
Figure 31:
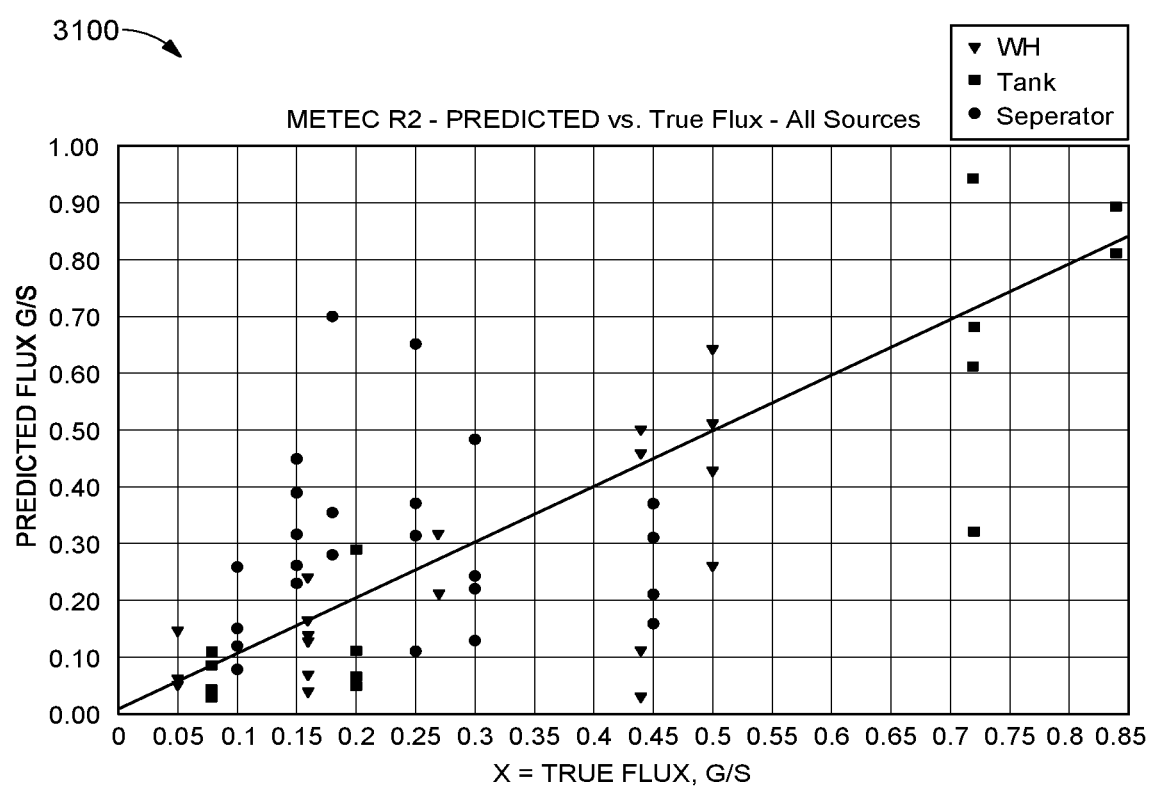
FIG. 31 illustrates a graphical representation of flux prediction error for all emission sources based on predictive algorithm for the experiments conducted at a site (e.g., METEC test site) over a cumulative period of three days, in accordance with an illustrative configuration of the present disclosure.

As mentioned earlier, as part of quantification MVP1, two models (Model N and Model S) may be developed for quantification, investigate the problem, and employ the best evaluation method for next development, MVP2. FIGS. 30 and 31 summarize the preliminary performance of the predictive algorithm for the forty four experiments conducted at METEC test site (Cumulative Period of 3 Days—July 21st to July 23rd/2021). In particular, FIG. 30 is a graphical representation 3000 of flux predictions for all emission sources based on predictive algorithm for the experiments conducted at a site (e.g., METEC test site) over a cumulative period of three days. FIG. 31 is a graphical representation 3100 of flux prediction error for all emission sources based on predictive algorithm for the experiments conducted at the site over the cumulative period of three days. Both model predictions may correlate well with the true emission rate as indicated by the proximity of the predictions to the forty-five-degree line.

As such, the quantification methods may be able to detect methane leaks in the range of g/s up to 0.85 g/s with a total site emission prediction error ranging from −16% to 3% at an average wind speed ranging from 0.5 m/s to 6 m/s at the site footprint and sensor configuration mentioned earlier. Total predicted site emission is the cumulative predicted emission rates of each experiment over the total test period of three days. For example, it was observed that the true total site emission was 50.22 kg of methane whereas the predicted values were 58.1 kg of methane using Model S, and 48.74 kg of methane using Model N. Referring once again to FIG. 21, the graphical representation 2100 shows the cumulative predictive emissions for METEC Site Emissions over the course of three days as compared to true emissions.

Additional testing planned on September at METEC may allow for further estimation of the error distribution as well as the prediction interval width and the overall emission rate prediction trend. As mentioned above, FIG. 30 illustrates flux predictions for all emission sources, and FIG. 31 illustrates flux prediction error for all emission sources. A comparison of true flux predictions (total site emissions) and the predicted flux predictions—with reference to model N and model-S is shown in FIG. 21.

A breakdown of total site emissions quantification methods per source against the true emitted quantities of methane may be recorded. It may be noted that both models (model N and model S) may be able to predict reasonably well except for few cases where unfavorable wind transport of emissions occur. Since this continuous monitoring technology relies on wind to advect air borne methane molecules to detector, unfavorable wind conditions could occasionally result in placing the detector upwind of a given emission source, creating a weak signal to noise inhibiting the detector from receiving the right information on emission source concentration. This would impact plume dispersion model ability to predict accurately.

Figure 32:
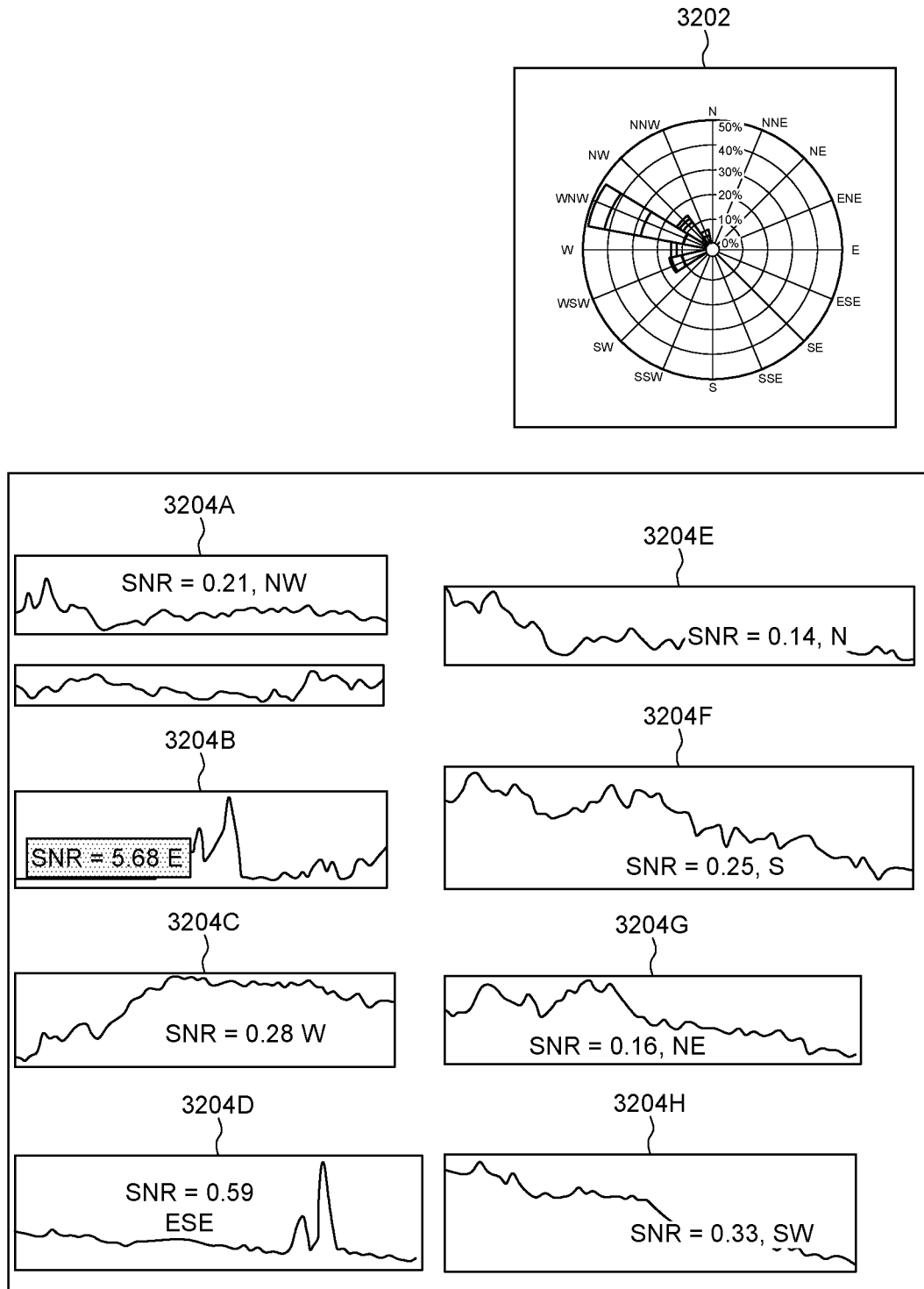
FIG. 32 illustrates a schematic representation of time-series concentration and wind speed for an example experiment study, in accordance with an illustrative configuration of the present disclosure.

FIG. 32 illustrates a schematic representation 3200 of time-series concentration and wind speed for an example experiment study. A wind rose diagram 3202 shows that the prevailing wind during this experiment was from WNW to ESE. Further, SNR graphs 3204 (i.e., graphs 3204A, 3204B, 3204C, 3204D, 3204E, 3204F, 3204G, 3204H) corresponding to eight sensors are shown along with determined SNR values. As a result of analysis of the SNR, resulting in seven out of eight sensors becoming upwind during this experiment which lasted for one hour. The SNR values confirmed this finding are indicated in the corresponding graphs 3024 for each of the sensors. As shown, SNR<0.7 (i.e., graphs 3204A, 3204C, 3204D, 3204E, 3204F, 3204G, 3204H) where detectors were not picking strong methane signal, and SNR>0.7 (3204B) where the detector is directly engaged in measuring the methane concentration.

In one configuration, in the current experiment study, only one methane detector is in the downwind measuring concentration. The quantification model is able to predict better excels with large amount of quality data.

Figure 33:
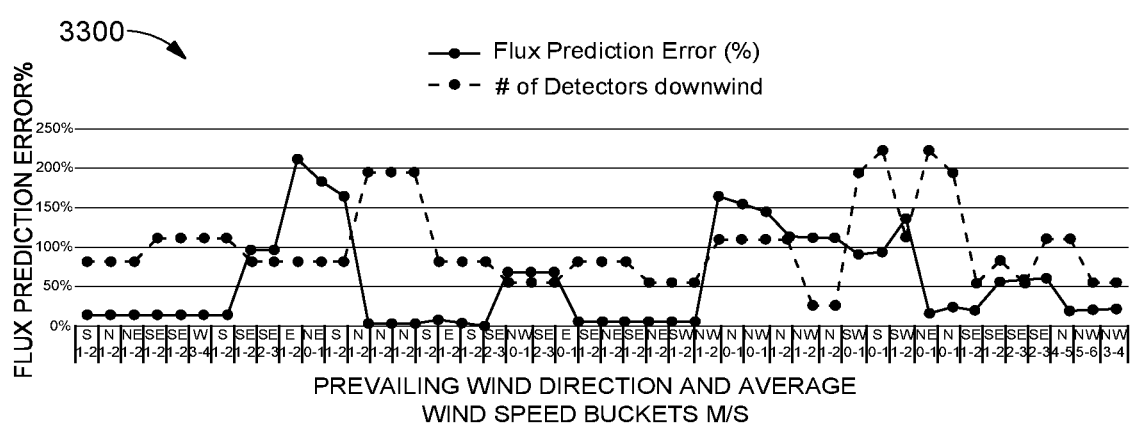
FIG. 33 illustrates a graphical representation of flux prediction error (%) as a function of wind speed (WS), wind direction (WD), upwind detectors, downwind detectors during a test period at a site, in accordance with an illustrative configuration of the present disclosure.

To evaluate the wind impact on model prediction error, a matrix of different parameters may be created, including number of active sensors downwind, number of inactive sensors upwind, prevailing wind direction, and average wind speed for each of the forty four experiments (hourly basis, 56 hours), as shown in FIG. 33. It may be noted that the number of detectors in the downwind may be inversely proportional to the prediction error due to feeding the model with more useful information that allows for better predictions as explained earlier. However, since this is a multivariant problem, therefore, the number of detectors may not be the only determinant as wind direction and speed have some role to play as well. During real deployment in oil field where representative detectors are permanently installed for continuous monitoring the above scenario of unfavorable wind will not be likely as wind direction and speed likely change during the day. FIG. 33 illustrates a graphical representation 3300 of flux prediction error (%) as a Function of wind speed (WS), wind direction (WD), upwind detectors, downwind detectors during the 51 hour test period at the site (i.e., METEC site).

The experimental errors can be divided into three categories, namely measurement error, bias error, and random sampling error. The measurement error is the inherent error involved in using a specific sensor that relies in its operation on some physical effect representing the response of the sensor to the quantity being measured. This error is often sizable in magnitude and could be quantified using calibration against a known reference. For sensor nodes experiments were conducted to estimate concentration errors at various reference concentrations. The bias error results from sampling specific regions of the underlying probability distribution, thus favoring certain times or operating conditions for the components under investigation. The only way to ensure sampling all potential values for emission concentrations may be to measure emissions for long enough to ensure quasi-stationary probability density functions (pdf) of the emission from a given equipment. Some models estimated that in most cases the equivalent of three-hour worth of data (i.e., every minute) is reasonable to ensure quasi-stationary pdf. This is not a general rule of thumb, it is just true for a representative dataset obtained from METEC site data. The random sampling error may occur when measuring a sample of a given quantity rather than the full population. In different realizations of the samples estimates may be different. In practice this is typically the smallest of all above three types of errors. It can be easily quantified using the bootstrapping techniques described above.

The performance of model S with data pre-processing and post-processing may be tested against a second round of experiments (forty four experiments) at the METEC site for three days (for example, from July 21st to Jul. 23, 2021). The results from the model S may be compared against the Gaussian Plume Model (GPM), which is essentially the model S without SNR and bootstrapping. The predicted release rates from the GPM may be the average flux from all detectors. Each experiment may be repeated three times, i.e., there are fifteen sets of three similar experiments.

Model S and GPM may be run over the fifteen sets of experiments to test the efficacy of data pre-processing and post-processing. A 95% confidence interval in the predicted release rates for GPM and Model S are shown in the y-axis of FIG. 34A-34B, where the center is the predicted (or average) release rate. Uncertainty in the data or true flux rate itself is then shown along the x-axis. There is an improvement in the predicting release rate, which can be seen as the short vertical error bounds of Model S.

Figure 34A:
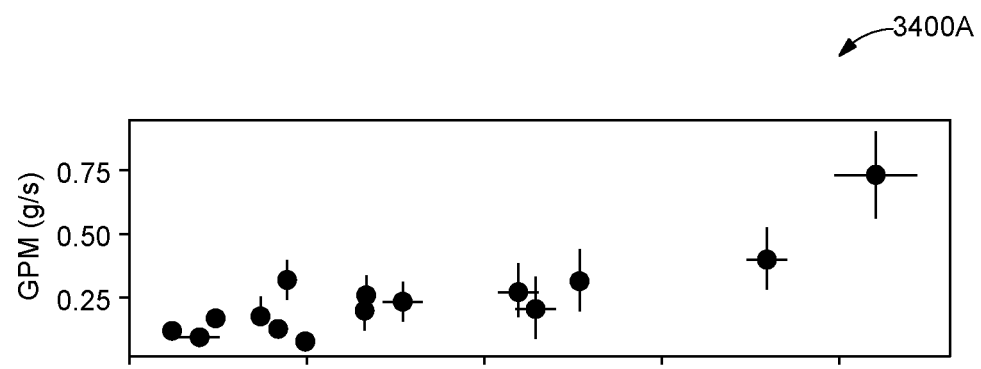
FIGS. 34A-34B illustrate graphical plotting of error bounds in a Gaussian Plume Model and a Model S, respectively, in accordance with an illustrative configuration of the present disclosure.
Figure 34B:
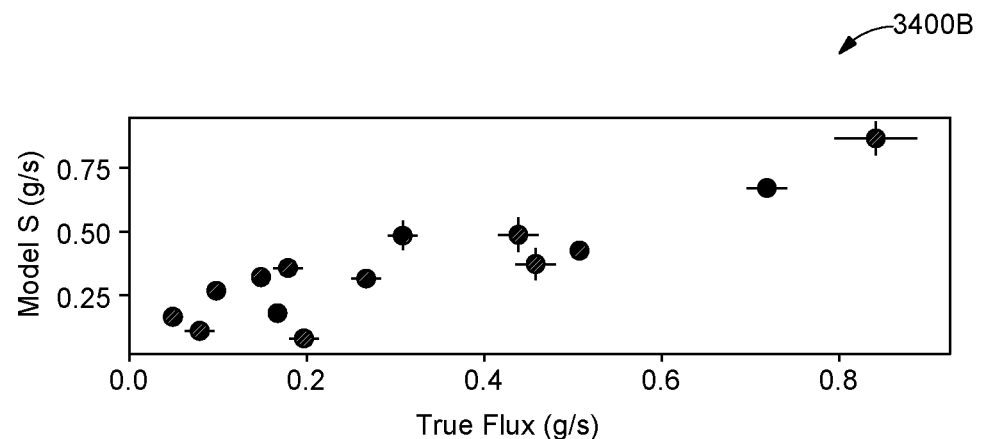

In some configurations, error bounds of Model N may be added for enabling comparison against GPM and Model S and highlight the differences. FIG. 34A illustrates a graphical plotting 3400A of error bounds in the GPM, and FIG. 34B illustrates a graphical plotting 3400B of error bounds in the Model S.

The above sensing and analytics platform (which was tested in a real-world environment at METEC site of Colorado State University as a practical test site during the said period) integrates detector data and cloud analytics to offer a complete IoT solution for remote locations where power availability and communications to the cloud may be challenging.

As part of quantification roadmap, the quantification methods are able to detect methane leaks in the range of 0.05 g/s up to 0.85 g/s with a total site emission prediction error ranging from −16% to 3% at an average wind speed ranging from 0.5 m/s to 6 m/s at the 200 ft×280 ft site and a detector to source distance ranging from 69 to 230 ft. Total predicted site emission is the cumulative predicted emission rates of each experiment over the total test period (of three days).

It may be noted that wind speed and direction variability as well as test duration and sensor placement may lead to some variability amongst replicates for the same flow rate.

As already explained in conjunction with FIGS. 11A-11E, the plume flux of the plume of emissions at the site may be determined by receiving a predetermined number of samples of the plume at a plurality of angles of the plume by the plurality of air quality monitors (i.e., sensors systems 1120) installed at the site. Further, an associated concentration point may be registered based on the plurality of angles. A fit of a point cloud may be obtained. When the measurements occur in idealized conditions of the site parameters, the plume flux may be calculated using a mass conservation equation by multiplying an area concentration of the plume cross section by its normal speed and by estimating the plume concentration in the height direction. The site parameters may include wind speed, wind direction, temperature, and other parameters associated with the site.

Figure 35:
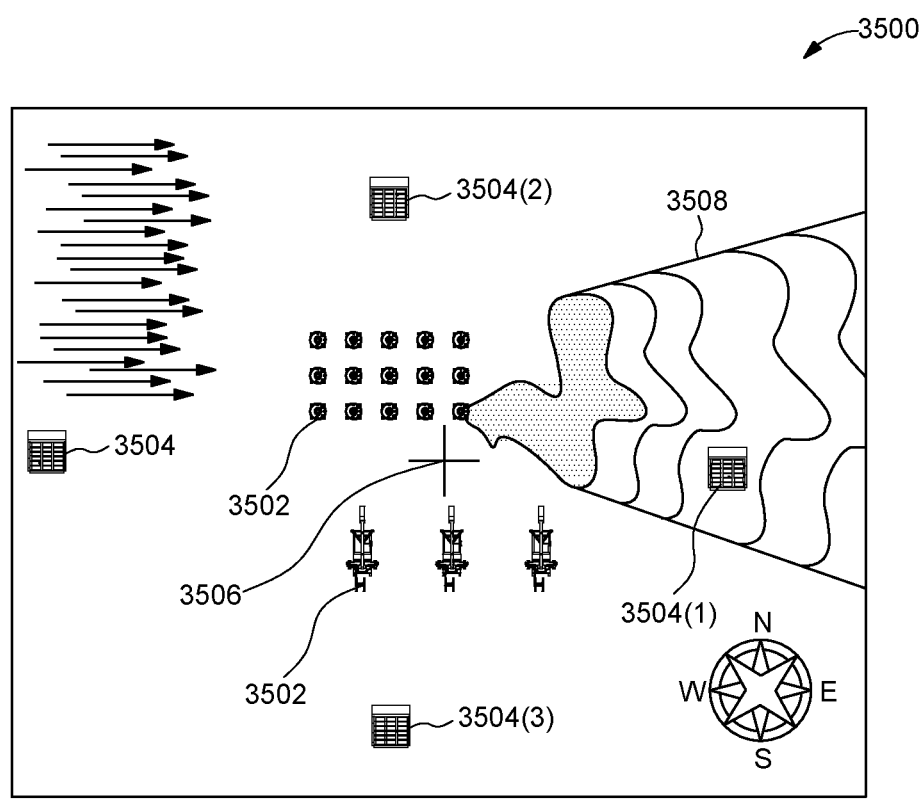
FIG. 35 illustrates a plan of an example site under monitoring, in accordance with an illustrative configuration of the present disclosure.

Referring now to FIG. 35, a plan 3500 of an example site under monitoring is illustrated. The site may include equipment 3502, and a plurality of air quality monitors 3504 (as mentioned before, air quality monitors may also be referred to as sensors, sensors systems, sensing system, detectors in this disclosure). Further, a method of installing an air quality monitor system at the site may be performed. The method may include surveying the site by procuring: an equipment log of a plurality of leak-prone equipment 3502 at the site, a centroid 3506 of the leak-prone equipment, and a wind-rose diagram representative of wind at the site. Surveying the site may further include procuring a 3D point cloud of topography of the site and procuring a 3D point cloud of the leak-prone equipment 3502 of the site. Upon surveying, the wind-rose diagram may attached be to the site.

The wind rose diagram is already illustrated in the FIG. 25. As shown in the FIG. 25, the wind-rose diagram may include the predominate downwind direction ("1"), the secondary downwind direction ("2") angularly offset from the predominate downwind direction ("1"), and a tertiary downwind direction ("3") angularly offset from the predominate downwind direction ("1") and oppositely disposed from the secondary downwind direction ("2").

A predominate air quality monitor 3504(1) may be installed at the site in the predominate downwind direction ("1") from the centroid 3506 at a location where the predominate air quality monitor 3504(1) has a maximal angular separation between the leak-prone equipment 3502. Before installing the predominate air quality monitor 3504(1), a site operator may be instructed to install a first vertical object (for example, a post, a pole, or any vertically aligned shaft) where the predominate air quality monitor 3504(1) will be installed. The predominate air quality monitor 3504(1) may be installed to the first vertical object. Further, a secondary air quality monitor 3504(2) may be installed in the secondary downwind direction ("2") from the centroid 3506 where the secondary air quality monitor 3504(2) has minimal observational overlap with the predominate air quality monitor 3504(1). Before installing the secondary air quality monitor 3504(2), the site operator may be instructed to install a second vertical object where the secondary air quality monitor 3504(2) will be installed. The secondary air quality monitor 3504(2) may be attached to the second vertical object. Furthermore, a tertiary air quality monitor 3504(3) may be installed in the tertiary downwind direction ("3") from the centroid 3506 where the tertiary air quality monitor 3504(3) has minimal observational overlap with the predominate air quality monitor 3504(1) and with the secondary air quality monitor 3504(2). Before installing the tertiary air quality monitor 3504(3), the site operator may be instructed to install a third vertical object where the tertiary air quality monitor 3504(3) will be installed. The tertiary air quality monitor 3504(3) may be attached to the third vertical object.

The predominate air quality monitor 3504(1), the secondary air quality monitor 3504(2), and the tertiary air quality monitor 3504(3) may be configured to obtain the first weather reading of local weather from a weather station and modify transmission of an emission data according to the weather reading obtained from the weather station. This is already explained in conjunction with FIG. 7A. As mentioned before, the sensor system (or, the air quality monitor) may include a weather sensor system 711 (also referred to as weather station 711). The weather sensor system 711 may include sensing elements to measure wind speed and direction. The wind speed and direction may be measured by a combination of a wind vane and an anemometer, or by an anemometer alone such as in the case of using an ultrasonic anemometer.

Further, a predominate connector may be communicatively coupled to the predominate air quality monitor 3504(1). Further, a predominate weather station may be communicatively coupled to the predominate air quality monitor 3504(1) at the predominate connector. Similarly, a secondary connector may be communicatively coupled to the secondary air quality monitor 3504(2). Further, a secondary weather station may be communicatively coupled to the secondary air quality monitor 3504(2) at the secondary connector. In the same way, a tertiary connector may be communicatively coupled to the tertiary air quality monitor 3504(3), and a tertiary weather station may be communicatively coupled to the tertiary air quality monitor 3504(3) at the tertiary connector.

The weather data from each of the predominate weather station, the secondary weather station, and the tertiary weather station may be transmitted to a cloud computing device (for example, "Amazon Web Services" or simply "AWS"). This weather data may be analyzed to determine redundant or non-contributing weather data. Further, at least one of the predominate weather station, the secondary weather station, and tertiary weather station may be removed. As will be appreciated, all the weather stations (i.e., the predominate weather station, the secondary weather station, and the tertiary weather station) may not contribute to the analysis, and therefore, the non-contributing weather station may be discarded.

In some embodiments, a ground temperature probe may be communicatively coupled to at least one of the predominate air quality monitor 3504(1), the secondary air quality monitor 3504(2), and the tertiary air quality monitor 3504(3). This ground temperature probe may provide a ground temperature. One of the predominate air quality monitor 3504(1), the secondary air quality monitor 3504(2), and the tertiary air quality monitor 3504(3) may transmit the ground temperature (for example to the "AWS"). Based on the ground temperature, a diffusion-area of emissions may be estimated. It may be noted the ground temperature, or the diffusion-area of emissions may be fed to the plume model for analysis.

In an illustrative configuration of the system, the environmental sensors are not collocated to the target gas sampling point. As explained in this disclosure, the collocation of environmental sensors such as the anemometer with the gas analysis sensor intake may improve the interpretation of the data because of the effect of topology and obstacles on the transport of the target gas. To this end, as mentioned above, the weather station may include the anemometer which may further include a due-North indicia. The weather station may be communicatively coupled to the predominate air quality monitor 3504(1) at the connector. The due-North indicia of the anemometer may be aligned to North of the Earth. A first weather reading of local weather may be transmitted from the weather station. The weather reading of local weather may include a wind speed and a wind direction.

In some embodiments, multiple sensors, for example three sensors (i.e., the predominate air quality monitor 3504(1), the secondary air quality monitor 3504(2), and the tertiary air quality monitor 3504(3)) may be deployed at the site, for example a gas pad. If the topology and obstacles configuration allows the environmental variables such as wind direction and wind speed are only marginally variable from the perspective of the different sensors deployed at the site. It may then be possible to reduce the number of environmental sensors, such as anemometers, by only positioning a single environmental sensor for multiple gas sensors. For example, on the site with three gas sensors, only one anemometer may be collocated with one of the three gas sensors, while no anemometer is used with the remaining two gas sensors. This allows for a reduction of the cost of deployment with only a marginal reduction of the efficacy of localizing, quantifying or qualifying emissions.

One illustrative configuration of the disclosure concerns the deployment of sensor to a site and the collection of site metadata. As mentioned above, once a site is selected for continuous monitoring, information about the site (i.e., surveying) is first collected in order to identify the best deployment locations. First site boundary and topologies are obtained. This may be offered by the site owner, or by consulting a satellite map databank. For example, in the case of a natural gas pad, the edge of the 50×75 m pad may be identified, and the terrain may be obtained using lidar maps from google earth. Then, the emplacement of equipment groups that are to be observed are identified. This may be done by inspection of the site, LIDAR mapping or by satellite image analysis. The equipment groups type, geometries and location are collected to establish the geometry and location of sources in the predictive simulations. For example, a trained operator may identify the equipment group and their size from satellite image and add then to the site topology of the digital twin. Additional local topology information about the terrain surrounding the site may also be added to the digital twin to improve simulations, for example by adding obstacles like trees and buildings, following a process similar to the identification of equipment groups. The next step or concurrent step is to identify local weather patterns. Historical wind conditions of the site may be extrapolated from the wind conditions at a proximate weather station, in particular the identification of the primary and secondary wind directions. For example, the cli-MATE tool from the Midwestern Regional Climate Center database may be used to construct historical wind rose from reference weather stations in the proximity of the site. Once the historical weather data is obtained, the position of the sensors may be decided. The sensors may follow deployment rules that are site dependent. In general, the objective is to maximize separate observations of the observed equipment groups or areas of interest. This means that the angular separation of the centroid of each equipment group from the perspective of the sensor should be maximized to enhance plume differentiation. Second, the sensor may only be deployed in an allowed area of the site. In the case of oil and gas pads, the site boundary is generally allowable as it is part of the site and far enough away from the hazard zone around the equipment groups. Third, the position of the sensor shall maximize the number of plume observations, this means that sensor shall be placed downwind of the observed equipment groups. With a limited number of sensors, this means that sensors shall be placed with regard to the principal (i.e., predominate) and secondary wind directions extracted from the historical weather data. If additional sensors are allowed, these shall be placed to maximize angular coverage of the equipment groups.

The first sensor (or predominate air quality monitor) is therefore placed close to the downwind direction of the principal (or, predominate) historical wind direction from the centroid of the equipment groups in a position that maximizes angular separation of the equipment groups. Assuming a secondary wind direction exists, a second sensor (or secondary air quality monitor) shall be placed downwind of the secondary historical wind direction in front the centroid of the equipment groups in a position that maximizes separation of the equipment groups and minimizes observational overlap with the first sensor. Subsequent sensors shall follow equivalent rules if additional secondary wind direction exists or maximize angular coverage of the site. For example, in a three sensor deployment on an oil and gas site, the first sensor position may be selected north of the site because of the south principal wind direction. The second sensor may be positioned southwest because of the secondary northeast wind direction and the third sensor (or tertiary air quality monitor) location may be set east of the site to maximize coverage. The exact position of the sensor may be shifted by few degrees based on local conditions and angular coverage. In the precedent example. The third sensor location may be shifted to southeast because this would give it a better angular position for observing all the equipment groups.

Once the prospective sensor position is established, the map of potential sensor location is shared with the operator of the site for approval and for site preparation. The operator may move or object to certain locations due to risk, need of access or future development project. The position may then either be corrected to accommodate this or the alternate location provided by the operator accepted. The operator may then proceed to the site preparation. For anchored sensors, this means the position of an anchor (e.g., a T-post) for the fastening of the sensor. Once the site preparation are over, the sensor systems may be deployed at the specified location of the site.

Optionally, the position of the sensor may further be shifted. This may happen if the operators plan require the sensor to be removed (e.g., the site may be modified) or if the observation data from the continuous monitoring of the site is suboptimal (e.g., the historical wind data from a proximate weather station was not applicable to the site). A new plan from the data acquired by the deployed sensors may then be conceived to relocate the sensor to more favorable locations.

As explained in conjunction with FIGS. 12 and 13, methods for the reduction of real time simulation cost by simulating many representative conditions in advance and using inverse methods for identifying matching conditions and predicting flux and source localization are provided. One alternative embodiment is the simulation in real time of the transport problem using real time experimental data, such as weather conditions, stability class and so on. While this may result in additional computational cost, this would reduce some of the modeling error by having more accurate specification of the boundary conditions. In some instances where dynamics is of importance, i.e., when the wind conditions are shifting during transport, this may yield more accurate results. It should be noted that for direct real time simulations, one may use a fully resolved advection diffusion transport model with appropriate closure of the turbulence flow (i.e., LES, RAS, etc) or use a reduced order model such as the gaussian plume model.

An optional computational cost saving approach may be adopted to sub-select periods of interest to simulate, rather than simulate the entire time sequence. For example, in a 24 hour period, only smaller periods within that 24 h period may be simulated, rather than the entire period, say 1 hour. The selection of the appropriate period may be derived directly from the data. For example, emissions may only be detected by the sensor systems when the wind direction is appropriate. In that case, only when the wind direction is within a certain range would the simulation be run. Another discriminant may be the concentration intensity detected by the sensor systems. In this case, only when an outlying concentration enhancement is detected that the simulation be run. An outlying concentration even would be indicative of an emission plume being detected.

An additional computational cost saving approach may lay in the choice of model. A reduced order model, such as the Gaussian Plume Model may first be run in real time for all selected periods of interest. This may allow for a first pass at quantification, localization, and qualification of emission. Then in a second step, a fully resolved advection diffusion transport model may be run to confirm or reduce the uncertainty of quantification, localization, and quantification on selected time periods of interest where the uncertainty of the reduced order model is higher than the uncertainty of the fully resolved model.

Referring back once again to FIG. 13B, the flowchart related to the execution of a real time model is illustrated. Fundamentally, the method in FIG. 13B is similar to the one given in FIG. 12 and FIG. 13A. In particular, the intermediary result of a relational matrix relating emission flux to emission concentration is shared by all method, which then requires an inverse method to solve. The initial problem to be simulated is slightly different, however. While the digital twin model and parameters are similar, and the search space for emission sources and flux amount is the same, the simulation uses weather measurements for the generation of initial and boundary conditions. In particular, temperature, pressure, hygrometry, and wind information may be used. Derived variables such as stability class, updraft, turbulent energy, standard deviation of wind and other input parameters may also be measured and calculated. In particular, the measurement of wind direction and speed at different points of the digital twin may be used to generate boundary conditions that mimic the boundary conditions of the real site during a period of interest. A direct simulation may then be conducted to identify the transport of the target compound by assuming variable sources and flux rates (together emission variables) [Ej]. This can be done using multiple simulations using different emission variables, or by simulating the transport from multiple sources and or multiple target gas in a single simulation over the period of interest. Many models may be used for the direct simulation, for example a full field advection diffusion transport model using an LES closure, or reduced order models such as the gaussian plume model. From the results of the direct simulation(s), the concentration of the target analytes at various time stamps of the simulated periods can be evaluated at the positions of the deployed sensor systems within the digital twin simulation. It is then possible to form the relational matrix that relates emission variables to concentrations of analytes. The inverse relation can then be obtained with an inversion method as presented in FIG. 12 and FIGS. 13A-B.

Figure 36:
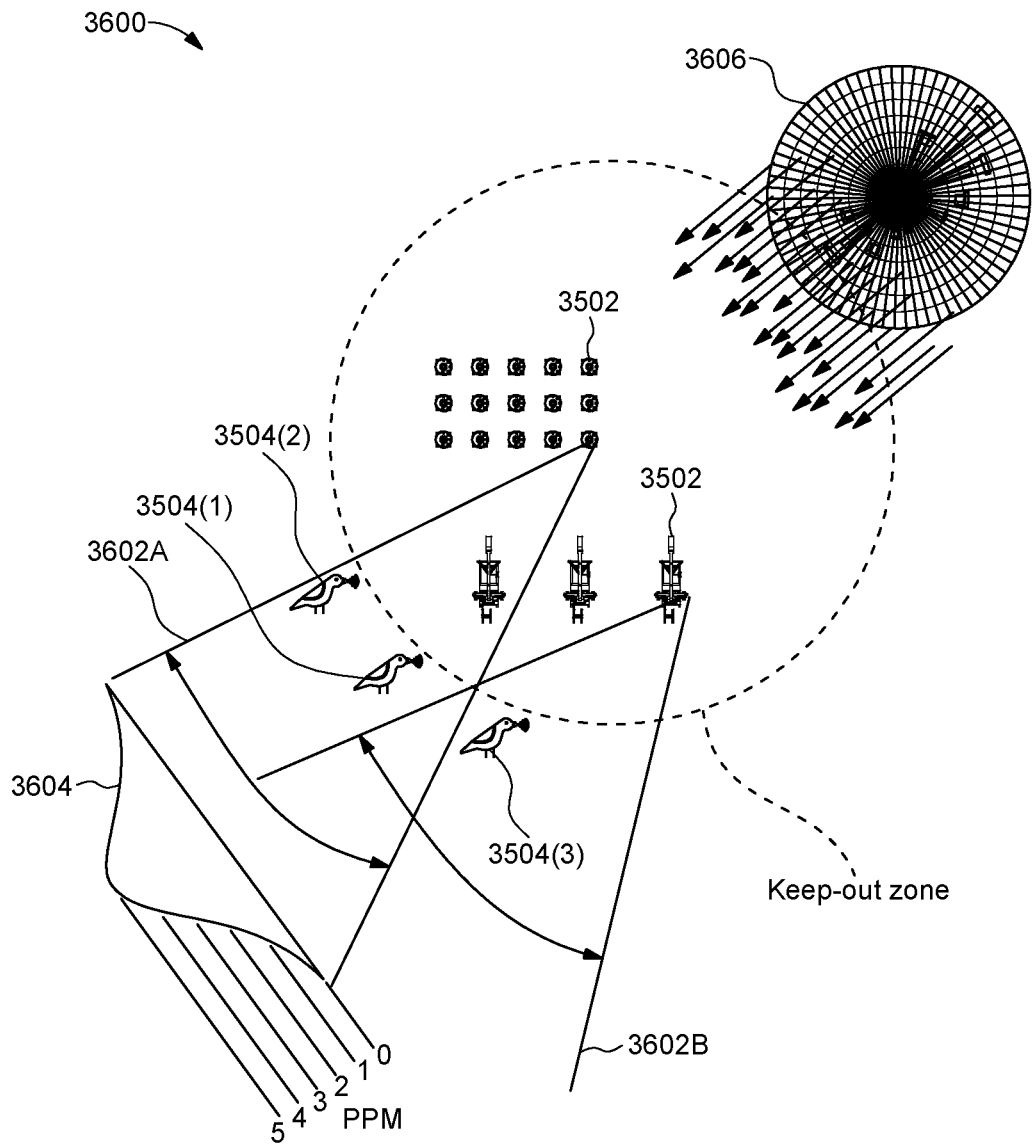
FIG. 36 illustrates another plan of an example site under monitoring, in accordance with an illustrative configuration of the present disclosure.

In particular, in order to identify a source of a target chemical at a site, a computer-implemented method may be performed. Referring now to FIG. 36, a plan 3600 of an example site under monitoring is illustrated. The site may include equipment 3502, the plurality of air quality monitors 3504 (as mentioned before, air quality monitors may also be referred to as sensors, sensors systems, detectors in this disclosure). According to the method, the predominate air quality monitor 3504(1) may be provided which may include a first sensor responsive to the target chemical and a first location information at which the predominate air quality monitor 3504(1) is located at the site. Further, a first concentration of the target chemical at the predominate air quality monitor 3504(1) may be measured as a function of a wind speed and a wind direction. It may be noted that other factors (for, example air temperature, air pressure, etc.) other than the wind speed and the wind direction may be taken into consideration as well. The wind speed and the wind direction may be measured using a wind sensor (e.g., an anemometer) which may be provided at the air quality monitor (as shown in FIG. 7C). The wind sensor may be located at the first location at the predominate air quality monitor 3504(1) or the second location at the secondary air quality monitor 3504(2). In case of an emission, a plume 3508 of the emission (i.e., the target chemical) may occur at the site. Further, the wind speed and the wind direction may be obtained from a wind rose diagram 3606.

In some configurations, the predominate air quality monitor 3504(1) may include a second sensor responsive to a second chemical that is different than the target chemical. Further, the method may include creating a containment table defined as a composition of liquid contained at each of the plurality of sources. The composition may include at least the target chemical or the second chemical. A second concentration of the second chemical at the predominate air quality monitor 3504(1) may be measured, and the measurements of each of the target chemical and the second chemical to the containment table may be compared. The source of the target chemical or the second chemical may be determined according to the containment table, and the identified source may be outputted to a computer device (for example, the mobile device 152).

As mentioned earlier, the air quality monitors (i.e., the predominate air quality monitor 3504(1), the secondary air quality monitor 3504(2), etc.) may obtain measurements of the concentration of air samples at regular intervals (i.e., a predetermined frequency/cadence). Further, under some conditions, the frequency/cadence of obtaining the measurements may be automatically increased or decreased for more accurate emission detection. To this end, in some configurations, a wind-speed-threshold algorithm indicative of improved confidence of sensor readings by the predominate air quality monitor 3504(1) and the secondary air quality monitor 3504(2) may be predetermined. As such, the wind speed may be monitored, and the wind speed may be compared to the wind-speed-threshold. At the wind-speed-threshold, cadence of the measuring of the first concentration may be increased.

In some configurations, a population of the actual emissions measurements may be transmitted to the cloud server (e.g., "AWS"). As mentioned above, some measurements may have noise, and therefore, may not be suitable for performing the plume analysis and may be discarded. To this end, a highest first concentration of the population of emissions measurements may be identified. Further, a lowest first concentration of the population of emissions measurements may be identified. Furthermore, an SNR threshold may be determined. For example, an SNR ratio may be determined by dividing the first concentration by a difference between the highest first concentration and the lowest first concentration. The individual readings of the first concentration that have an SNR ratio below the SNR threshold may be discarded.

Figure 37:
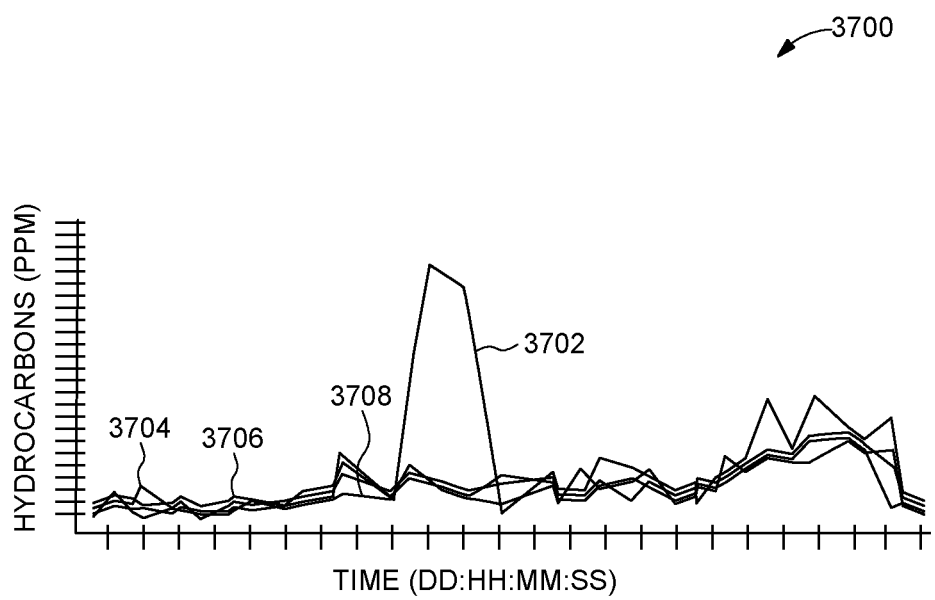
FIG. 37 illustrates a graphical representation of example SNRs associated with different sensors deployed at a site, in accordance with an illustrative configuration of the present disclosure.

FIG. 37 illustrates a graphical representation 3700 of example SNRs associated with different sensors (air quality monitors 3504). For example, an SNR for the predominate air quality monitor 3504(1) may be depicted by a curve 3702, an SNR for the secondary air quality monitor 3504(2) may be depicted by a curve 3704, an SNR for the tertiary air quality monitor 3504(3) may be depicted by a curve 3706, and an SNR for another air quality monitor 3504 may be depicted by a curve 3708. Further, a threshold SNR of 0.7 may be selected. Based on this SNR, the air quality monitors with SNR<0.7 may be discarded. This is already explained in conjunction with FIGS. 27-29.

According to the method, a horizontal distribution deviation defined as a standard deviation of a horizontal distribution of a plume concentration may be obtained. Similarly, a vertical distribution deviation defined as a standard deviation of a vertical distribution of the plume concentration may be obtained. Further, according to the method, at least one simulation model may be created for the site based on simulation parameters. As mentioned above, the simulation parameters may include at least two of a wind directions, a wind speed, an air pressure, an air temperature, a number of potential emission sources, a location of each of the potential emission source, a source flux associated with each of the potential emission sources, a surface concentration, a weather condition, a hygrometry data, an altitude, etc.

For example, as shown in the FIG. 36, a first plume model 3602A and a second plume model 3602B may be generated corresponding to two different potential emission sources, based on the various simulation parameters including wind direction and wind speed (as provided by the wind rose diagram 3606). Further, for example, the plume model 3602A may have a configuration 3604 (along y-plane).

An emission rate of the target chemical at the source may be identified using the simulation model functionally which may be operated by the standard deviation of horizontal distribution, the standard deviation of vertical distribution, the first concentration at the predominate air quality monitor 3504(1), and the wind speed. The identified source may be outputted to a computer device and displayed for a user.

Additionally, in some configurations, the secondary air quality monitor 3504(2) may be provided that may include a second sensor responsive to the target chemical, and a second location information at which the secondary air quality monitor 3504(2) is located. A second concentration of the target chemical at the secondary air quality monitor 3504(2) may be measured as a function of the wind speed and the wind direction. According to the method, a first bearing of the source relative to the predominate air quality monitor 3504(1) may be identified using the simulation model. Further, a second bearing of the source relative to the secondary air quality monitor 3504(2) may be identified using the simulation model. Thereafter, in some configurations, coordinates of the location of source of the target chemical may be identified using the first bearing and the second bearing. Further, the source may be identified from a plurality of possible sources of the target chemical by correlating the identified coordinates of the source with the emission rate. The coordinates and the emission rate of the identified source may be outputted to the computing device.

According to the method, a concentration profile may be built according to a plurality of inputs. The plurality of inputs may include concentration of emission and the wind direction. Further, a wind speed dependent variable may be created according to the concentration profile sourced as the wind speed fluctuates. The location of the emission source may be determined according to the plurality of concentration profiles effected by the wind speed.

Further, in some configurations, a maximum of the first concentration of the target chemical at the predominant air quality monitor along with the wind direction may be logged. Further, a plume centerline may be established as the wind direction less 180 degrees from the location of the predominant air quality monitor, to thereby identify a direction of the source of the target chemical from the predominant air quality monitor.

In one embodiment, the composition of the emission may be an indicator for refining the localization of emission. Emissions may contain different compounds based on their origin in the site. Indeed, the product may be separated or transformed at the site. If multiple target compounds are monitored, the ratio of these may indicate different processes.

For example, in natural gas extraction, natural gas from the well may contain various compounds such as methane, heavier hydrocarbons such as ethane, propane and butane, trace VOC such as H2S, Toluene, additives such as methanol (for preventing hydrate formation) and additional gas and liquids such as CO2 and water. This multiphase flow is then separated in the separator, and liquids are stored in tanks. As a result, emission prior to separation, during separation, after separation and from the tanks may have different ratios and composition of these compounds. If the sensor system can detect more than one compound, or group of compounds, refinement can be obtained in process step identification. For example, a VOC sensor may be used in conjunction with a methane sensor to differentiate emission within the process. Methane emissions with less VOC may come from post separation methane gas while emission with more VOC may come from the tanks.

In one configuration, virtual emissions and/or simulation models created by a mathematical model may be utilized. One illustrative mathematical model is the Navier-Stokes function in fluid mechanics that describes the flow of fluids (such as, for example, the flow of air). The Navier-Stokes function may be derived from an equation devised by Swiss mathematician Leonhard Euler to describe the flow of incompressible and frictionless fluids. Other physicists and mathematicians (e.g., Sir George Gabriel Stokes) have evolved the model to improve both two-degree and three-degree models. Complex vortices and turbulence, often referred to as chaos, that occur in three-dimensional fluid (including gas) flows as velocities increase have proven intractable to any but approximate numerical analysis methods. Examples of methods include Euler's original equation, Guglielmo Marconi wireless communications models, Laplace's equation, Gaussian Plume Model (GPM), Large Eddy Simulation (LES), and the like. Navier-Stokes equations may be found and incorporated, such as those—for example—found at https://en.wikipedia.org/wiki/Navier%E2%80%93Stokes_equations which is specifically incorporated by reference for all that is disclosed and taught therein.

In one example, the present disclosure may include a sensor system configured to monitor compounds in air and collocate weather measurements with self-powering, sample conditioning, edge processing, and/or communication capability.

In another example, the present disclosure may include a method including: analyzing spectra for at least one of denoising, debiasing, peak alignment, speciation, or unknown compound and residual bias and noise compensation.

In another example, the present disclosure may include a method including detecting, localizing, and/or quantifying a site emission using a single static point sensor sensitive to at least one target compound and providing collocated measurement of weather.

Furthermore, the method may include the measurement of weather includes at least wind speed and wind direction determined based on atmospheric simulations and inverse methods.

In another example, the present disclosure may include a method including: qualifying of emission type using statistical inference, which at least distinguishes a normal emission from a leak.

In another example, the present disclosure may include a method including detecting at least one emission; and determining whether at least one emission is from one or more leaks.

In another example, the present disclosure may include a method for the calculation of total site emissions.

In another example, the present disclosure may include a method for the estimation of total flux emission of landfills using one or more of surface concentrations and/or local weather measurements together with a transport simulation.

In another example, the present disclosure may include a method for the estimation of the detection area of a sensor system using transport simulation.

In another example, the present disclosure may include a method for optimizing a formation of sensor system networks relying on detection threshold and detection speed requirements together with a large scale transport simulation.

In another example, the present disclosure may include a method to triage and report emission flags for maintenance based on their location, quantification, and qualification.

In another example, the present disclosure may include an actionability engine for the tracking and suggestion of practices, equipment, and manpower for proper leak maintenance.

In another example, the present disclosure may include a n actionability engine for the identification of repeat-offending components and component types.

In another example, the present disclosure may include a n actionability engine for tracking of emission reduction goals.

In another example, the present disclosure may include a system including a computing device including one or more processors and memory storing instructions that, when executed by the one or more processors, cause the system to perform one of the methods described.

In another example, the present disclosure may include a system of claim 15, further including one or more sensors in communication with the computing device and configured to detect one or more emissions, wherein the computing device is configured to identify a leak based on the detected one or more emissions.

The system may further include using one or more weather simulations and the detected one or more emissions to identify the leak.

In another example, the present disclosure may include a method including determining one or more characteristics of one or more site emissions using a single static point sensor sensitive to at least one target compound and providing collocated measurement of weather. In another example, the present disclosure may further include quantifying the one or more site emissions by measuring a plume cross section across varying wind. And, the method may further include quantifying the one or more site emissions by estimating of an emission flux from concentration and weather measurements using an inverse transport simulation of a digital twin.

In another example, the present disclosure may include a deriving localized site emissions concentration and weather measurements using an inverse transport simulation of a digital twin.

In another example, the present disclosure may include a method including localizing site emissions by distinguishing between emission sources at a zone, equipment group, and/or component level emissions.

In another example, the present disclosure may include a method including: qualifying of emission type using statistical inference, which at least distinguishes a normal emission from a leak by categorizing emission events based on their intensity, frequency and/or composition.

In another example, the present disclosure may include a method for the estimation of emission localization, quantification and localization using operational data streams, maintenance and inspection reports and raw inspection data.

In another example, the present disclosure may include a method for the commoditization of emission estimation and measurement through certification, carbon credit and carbon offsets.

In another example, the present disclosure may include a method for preventative maintenance scheduling based on emission estimation and measurements.

In another example, the present disclosure may include a method for calculating and optimizing emission reduction costs for different operational strategies based on sensor measurements, geography, production data, equipment, maintenance data, labor costs, and/or other available data. In another example, the present disclosure may further include a method including the sensor measurements include weather and chemical concentration measurements.

In another example, the present disclosure may include a method for generating an atmospheric digital twin using site metadata for simulating atmospheric transport.

In another example, the present disclosure may include a method for quantifying error in localization and quantification of emissions of a site, using uncertainty quantification and prior probability of weather measurement precision and accuracy, modeling uncertainty and compound sensing accuracy and precision.

Specific details are given in the above description to provide a thorough understanding of the embodiments. However, it is understood that the embodiments may be practiced without these specific details. For example, circuits may be shown in block diagrams in order not to obscure the embodiments in unnecessary detail. In other instances, well-known circuits, processes, algorithms, structures, and techniques may be shown without unnecessary detail in order to avoid obscuring the embodiments.

Also, it is noted that the embodiments may be described as a process which is depicted as a flowchart, a flow diagram, a swim diagram, a data flow diagram, a structure diagram, or a block diagram. Although a depiction may describe the operations as a sequential process, many of the operations can be performed in parallel or concurrently. In addition, the order of the operations may be re-arranged. A process is terminated when its operations are completed, but could have additional steps not included in the figure. A process may correspond to a method, a function, a procedure, a subroutine, a subprogram, etc. When a process corresponds to a function, its termination corresponds to a return of the function to the calling function or the main function.

For a firmware and/or software implementation, the methodologies may be implemented with modules (e.g., procedures, functions, and so on) that perform the functions described herein. Any machine-readable medium tangibly embodying instructions may be used in implementing the methodologies described herein. For example, software codes may be stored in a memory. Memory may be implemented within the processor or external to the processor. As used herein the term "memory" refers to any type of long term, short term, volatile, nonvolatile, or other storage medium and is not to be limited to any particular type of memory or number of memories, or type of media upon which memory is stored.

The controllers, computing devices, server devices, and other components of systems can include machine-readable media and one or more processors, Programmable Logic Controllers, Distributed Control Systems, secure processors, memory, and the like. Secure storage may also be implemented as a secure flash memory, secure serial EEPROM, secure field programmable gate array, or secure application-specific integrated circuit. Processors can be standard central processing units or secure processors. Secure processors can be special-purpose processors that can withstand sophisticated attacks that attempt to extract data or programming logic. A secure processor may not have debugging pins that enable an external debugger to monitor the secure processor's execution or registers. In other embodiments, the system may employ a secure field programmable gate array, a smartcard, or other secure devices. Other types of computing devices can also be used.

Memory can include standard memory, secure memory, or a combination of both memory types. By employing a secure processor and/or secure memory, the system can ensure that both data and instructions are highly secure. Memory can be incorporated into the other components of the controller system and can store computer-executable or processor-executable instructions, including routines executed by a programmable computing device. In some embodiments, the memory can store programs for preset configurations. Stored programs (e.g., simulation programs, calibration programs, graphic mapping programs, etc.) can be modified by a subject, operator, or remote manager to provide flexibility.

The present disclosure contemplates methods, systems, and program products on any machine-readable media for accomplishing various operations. The embodiments of the present disclosure may be implemented using existing computer processors, or by a special-purpose computer processor for an appropriate system, incorporated for this or another purpose, or by a hardwired system. Embodiments within the scope of the present disclosure include program products comprising machine-readable media for carrying or having machine-executable instructions or data structures stored thereon. Such machine-readable media can be any available media that can be accessed by a general purpose or special purpose computer or other machine with a processor. By way of example, such machine-readable media can comprise RAM, ROM, EPROM, EEPROM, CD-ROM or other optical disk storage, magnetic disk storage or other magnetic storage devices, or any other medium which can be used to carry or store desired program code in the form of machine-executable instructions or data structures, and which can be accessed by a general purpose or special purpose computer or other machine with a processor. When information is transferred or provided over a network or another communications connection (either hardwired, wireless, or a combination of hardwired or wireless) to a machine, the machine properly views the connection as a machine-readable medium. Thus, any such connection is properly termed a machine-readable medium. Combinations of the above are also included within the scope of machine-readable media. Machine-executable instructions include, for example, instructions and data which cause a general purpose computer, special purpose computer, or special purpose processing machines to perform a certain function or group of functions. The machine-readable media can be part of sensors, computing devices, or other components disclosed herein.

Unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. The term "comprising" is used throughout to mean including at least the recited feature(s) such that any greater number of the same feature and/or additional types of other features are not precluded. It will also be appreciated that specific embodiments have been described herein for purposes of illustration, but that various modifications may be made without deviating from the technology. Further, while advantages associated with certain embodiments of the technology have been described in the context of those embodiments, other embodiments may also exhibit such advantages, and not all embodiments necessarily need to exhibit such advantages to fall within the scope of the technology. Accordingly, the disclosure and associated technology can encompass other embodiments not expressly shown or described herein. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

Implementation of the techniques, blocks, steps, and means described above may be done in various ways. For example, these techniques, blocks, steps, and means may be implemented in hardware, software, or a combination thereof. For a digital hardware implementation, the processing units may be implemented within one or more application specific integrated circuits (ASICs), digital signal processors (DSPs), digital signal processing devices (DSPDs), programmable logic devices (PLDs), field programmable gate arrays (FPGAs), processors, controllers, micro-controllers, microprocessors, other electronic units designed to perform the functions described above, and/or a combination thereof. For analog circuits, they can be implemented with discreet components or using monolithic microwave integrated circuit (MMIC), radio frequency integrated circuit (RFIC), and/or micro electro-mechanical systems (MEMS) technologies.

Furthermore, embodiments may be implemented by hardware, software, scripting languages, firmware, middleware, microcode, hardware description languages, and/or any combination thereof. When implemented in software, firmware, middleware, scripting language, and/or microcode, the program code or code segments to perform the necessary tasks may be stored in a machine readable medium such as a storage medium. A code segment or machine-executable instruction may represent a procedure, a function, a subprogram, a program, a routine, a subroutine, a module, a software package, a script, a class, or any combination of instructions, data structures, and/or program statements. A code segment may be coupled to another code segment or a hardware circuit by passing and/or receiving information, data, arguments, parameters, and/or memory contents. Information, arguments, parameters, data, etc. may be passed, forwarded, or transmitted via any suitable means including memory sharing, message passing, token passing, network transmission, etc.

The methods, systems, devices, graphs, and/or tables discussed herein are examples. Various configurations may omit, substitute, or add various procedures or components as appropriate. For instance, in alternative configurations, the methods may be performed in an order different from that described, and/or various stages may be added, omitted, and/or combined. Also, features described with respect to certain configurations may be combined in various other configurations. Different aspects and elements of the configurations may be combined in a similar manner. Also, technology evolves and, thus, many of the elements are examples and do not limit the scope of the disclosure or claims. Additionally, the techniques discussed herein may provide differing results with different types of context awareness classifiers.

Unless defined otherwise, all technical and scientific terms used herein have the same meaning as commonly or conventionally understood. As used herein, the articles "a" and "an" refer to one or to more than one (i.e., to at least one) of the grammatical object of the article. By way of example, "an element" means one element or more than one element. "About" and/or "approximately" as used herein when referring to a measurable value such as an amount, a temporal duration, and the like, encompasses variations of ±20% or ±10%, ±5%, or +0.1% from the specified value, as such variations are appropriate to in the context of the systems, devices, circuits, methods, and other implementations described herein. "Substantially" as used herein when referring to a measurable value such as an amount, a temporal duration, a physical attribute (such as frequency), and the like, also encompasses variations of ±20% or ±10%, ±5%, or +0.1% from the specified value, as such variations are appropriate to in the context of the systems, devices, circuits, methods, and other implementations described herein.

As used herein, including in the claims, "and" as used in a list of items prefaced by "at least one of" or "one or more of" indicates that any combination of the listed items may be used. For example, a list of "at least one of A, B, and C" includes any of the combinations A or B or C or AB or AC or BC and/or ABC (i.e., A and B and C). Furthermore, to the extent more than one occurrence or use of the items A, B, or C is possible, multiple uses of A, B, and/or C may form part of the contemplated combinations. For example, a list of "at least one of A, B, and C" may also include AA, AAB, AAA, BB, etc.

While illustrative and presently preferred embodiments of the disclosed systems, methods, and/or machine-readable media have been described in detail herein, it is to be understood that the inventive concepts may be otherwise variously embodied and employed, and that the appended claims are intended to be construed to include such variations, except as limited by the prior art. While the principles of the disclosure have been described above in connection with specific apparatuses and methods, it is to be clearly understood that this description is made only by way of example and not as limitation on the scope of the disclosure.

What is claimed is:

1. An identification method for identifying a target chemical at a site, the identification method comprising:
providing a sampling inlet to:
capture a sample of air from an atmosphere surrounding the site;
providing a compound sensor, comprising:
a sample cell to receive the sample of air from the sampling inlet;
a light source adjoined to the sample cell to emit a beam of light,
wherein the beam of light passes through the sample cell; and
a spectrophotometer adjoined to the sample cell;
generating a first transmission spectrum of the beam of light with the spectrophotometer;
transmitting a sample of air for interacting with the beam of light in the sample cell;
generating a second transmission spectrum of the beam of light in response to interacting the sample of air with the beam of light with the spectrophotometer;
processing the second transmission spectrum by:
denoising and de-biasing the second transmission spectrum to generate a processed second transmission spectrum;
generating an absorption spectrum of the beam of light by calculating absorbance of the beam of light by the sample of air based on:
comparing the first transmission spectrum to the processed second transmission spectrum; and
identifying the target chemical by decomposing the absorption spectrum to extract an absorption spectra related to the target chemical.

2. The identification method of claim 1, wherein providing the sampling inlet further comprises:
providing a pump to transfer the sample of air to the sample cell; and
providing a filter for removing particulate matter and water present in the sample of air.

3. The identification method of claim 1 and further comprising:
storing the absorption spectra of the target chemical in a database.

4. The identification method of claim 1 and further comprising:
providing an entry point and an exit point for the sample of air on the sample cell; and
naturally feeding the sample of air into the sample cell through the entry point and the exit point.

5. The identification method of claim 1 and further comprising:
adjoining an optical element to the sample cell,
wherein the optical element is configured to collimate and focus the beam of light into the spectrophotometer.

6. The identification method of claim 1 and further comprising:
plotting a transmittance wavelength graph for the processed second transmission spectrum of the beam of light;
identifying an absorption peak in the transmittance wavelength graph for the processed second transmission spectrum; and analyzing a shape, width, and position of the absorption peak to indicate a signature profile of the target chemical.

7. The identification method of claim 6, wherein the shape, width, and position of the absorption peak is dependent on:
an instrument transfer function of the spectrophotometer; and
a temperature, a pressure and concentration of the target chemical in the sample of air.

8. An identification system to identify a target chemical at a site, the identification system comprising:
a sampling inlet to:
capture a sample of air from an atmosphere surrounding the site;
a compound sensor, comprising:
a sample cell to receive the sample of air from the sampling inlet;
a light source adjoined to the sample cell to emit a beam of light,
wherein the beam of light passes through the sample cell and interacts with the sample of air; and
a spectrophotometer adjoined to the sample cell to:
generate a first transmission spectrum of the light; and
generate a second transmission spectrum of the light in response to the beam of light interacting with the sample of air; and
a logic control system connected to the compound sensor, configured to:
process the second transmission spectrum by:
denoising and debiasing the second transmission spectrum to generate a processed second transmission spectrum;
generate an absorption spectrum by calculating absorbance, wherein the absorbance is calculated by comparing the first transmission spectrum to the processed second transmission spectrum; and
identify the target chemical by decomposing the absorption spectrum to extract an absorption spectra related to the target chemical.

9. The identification system of claim 8 wherein the sampling inlet further comprises:
a pump to transfer the sample of air to the sample cell; and
a filter for removing particulate matter and water present in the sample of air.

10. The identification system of claim 8 and further comprising:
a database configured to store the absorption spectra of the target chemical.

11. The identification system of claim 8, wherein:
the sample cell comprises an entry point and an exit point for the sample of air, wherein the sample of air is naturally fed in to the sample cell through the entry point and the exit point.

12. The identification system of claim 8 and further comprising:
an optical element adjoined to the sample cell, wherein the optical element is configured to collimate and focus the beam of light into the spectrophotometer.

13. The identification system of claim 8, wherein the logic control system is configured to:
plot a transmittance wavelength graph for the processed second transmission spectrum of the beam of light;
identify an absorption peak in the transmittance wavelength graph for the processed second transmission spectrum; and analyze a shape, width, and position of the absorption peak to indicate a signature profile of the target chemical.

14. The identification system of claim 13, wherein the shape, width, and position of the absorption peak is dependent on:
- an instrument transfer function of the spectrophotometer; and
- a temperature, a pressure and concentration of the target chemical in the sample of air.

* * * * *